(12) United States Patent
Rothschild et al.

(10) Patent No.: US 12,116,420 B1
(45) Date of Patent: Oct. 15, 2024

(54) FUNCTIONALIZING BIOLOGICAL SUBSTRATES WITH BIOENGINEERED PEPTIDES TO BIND TARGETED MOLECULES

(71) Applicant: United States of America as Represented by the Administrator of NASA, Washington, DC (US)

(72) Inventors: Lynn Justine Rothschild, Woodside, CA (US); Jesica Urbina, El Paso, TX (US); Advait Avinash Patil, San Jose, CA (US)

(73) Assignee: United States of America as represented by the Administrator of NASA and the Secretary of the Interior, Washington, DC (US)

( * ) Notice: Subject to any disclaimer, the term of this patent is extended or adjusted under 35 U.S.C. 154(b) by 497 days.

(21) Appl. No.: 17/073,226

(22) Filed: Oct. 16, 2020

Related U.S. Application Data

(60) Provisional application No. 62/916,179, filed on Oct. 16, 2019.

(51) Int. Cl.
  *C07K 17/10* (2006.01)
  *B01J 20/26* (2006.01)
  (Continued)

(52) U.S. Cl.
  CPC ............. *C07K 17/10* (2013.01); *B01J 20/265* (2013.01); *C02F 1/288* (2013.01); *C07K 14/001* (2013.01);
  (Continued)

(58) Field of Classification Search
  None
  See application file for complete search history.

(56) References Cited

U.S. PATENT DOCUMENTS

| 5,514,779 A | 5/1996 | Broekaert et al. |
| 6,408,208 B1 | 6/2002 | Chen et al. |

(Continued)

OTHER PUBLICATIONS

A. Patil, "Part:BBa_K2868015" https://parts.igem.org/Part:BBa_K2868015, dated Oct. 8, 2018, downloaded Oct. 21, 2023 (Year: 2018).*

(Continued)

*Primary Examiner* — Chester T Barry
(74) *Attorney, Agent, or Firm* — Meredith K. Blasingame; Robert M. Padilla; Trenton J. Roche

(57) ABSTRACT

Method of removing or adsorbing a target substance or material, for example a metal, non-metal toxin, dye, or small molecule drug), from solution by functionalizing a substrate with a peptide configured to selectively bind to the target substance or material and to bind to the substrate. Methods herein are useful for example for biomining applications. More specifically, the method employs metal-binding peptides to remove metals from solution, particularly aqueous solution. More specifically, the substrate is fungal mycelium. Fusion peptides and/or proteins containing metal-binding domain sequence and optionally containing substrate-binding domain sequence are provided. Fusion peptides/proteins containing a metal-binding domain and a chitin-binding domain are provided. Also provided are nucleic acids encoding fusion peptides and/or proteins containing metal-binding domain sequence and those further containing a substrate-binding domain, for example a carbohydrate-binding domain, and more specifically a chitin-binding domain.

20 Claims, 15 Drawing Sheets

Specification includes a Sequence Listing.

(51) Int. Cl.
  *C02F 1/28* (2023.01)
  *C07K 14/00* (2006.01)
  *C02F 101/20* (2006.01)
(52) U.S. Cl.
  CPC .......... *C02F 1/285* (2013.01); *C02F 2101/20* (2013.01); *C07K 2319/20* (2013.01)

(56) References Cited

U.S. PATENT DOCUMENTS

| | | | |
|---|---|---|---|
| 7,060,465 | B2 | 6/2006 | Xu et al. |
| 7,445,922 | B2 | 11/2008 | Nakane et al. |
| 7,659,362 | B2 | 2/2010 | Yeh et al. |
| 7,662,826 | B2 | 2/2010 | Seno et al. |
| 8,506,717 | B2 | 8/2013 | Bansal et al. |
| 8,618,066 | B1 | 12/2013 | McDaniel |
| 10,377,795 | B2 | 8/2019 | Hatanaka et al. |

OTHER PUBLICATIONS

Baldwin G.S. et al. High affinity binding of Indium and Ruthenium ions by Gastrins. PLOS ONE. 10(10): e0140126. DOI:10.1371/journal.pone.0140126 (2015).

Black G.W. et al. A modular xylanase containing a novel non-catalytic xylan-specific binding domain. Biochem J. 307:191-195 (1995).

Cerimi K. et al. Fungi as source for new bio-based materials: a patent review. Fungal Biology and Biotechnology. 6:17. (2019). DOI: /10.1186/s40694-019-0080-y.

Cetinel S. et al. Biomining of MoS2 with Peptide based Smart Biomaterials. Nat. Scientific Reports. (2018) 8:3374 | DOI:10.1038/s41598-018-21692-4 (Feb. 2018).

Chen X. et al. Fusion protein linkers: Property, design and functionality. Adv. Drug Delivery Reviews. 65:1357-1369 (2013).

Chen Y. et al. Characterization of the Organic Component of Low-Molecular-Weight Chromium-Binding Substance and Its Binding of Chromium. J. of Nutrition (American Society for Nutrition). 141(17): 1225-1232. DOI: 10.3945/n.111.139147.

Chichili V. P. R. et al. Linkers in the structural biology of protein-protein interactions. Protein Science. 22(2), 153-167 (2013).

Hatanaka T. et al. Rationally designed mineralization for selective recovery of the rare earth elements. Nature Communications. 8:15670. 10 pp. DOI: 10.1038/ncomms15670 (May 2017).

Heymann D. et al. Structure of a Consensus Chitin-Binding Domain Revealed by Solution NMR. Preprint posted Jan. 9, 2020. Available at the web site bioRxiv.org. DOI: 10.1101/2020.01.08.899344.

Horaru M. et al. Probing Metal Ion Discrimination in a Protein Designed to Bind Uranyl Cation with Femtomolar Affinity. Frontiers Molecular Biosciences. 6 Article 73. (Aug. 2019).

Kozisek, M. et al. Molecular Design of Specific Metal Binding Peptide Sequences from Protein Fragments: Theory and Experiment. Chemistry-A European Journal. 14(26), 7836-7846 (2008).

Li H. et al. Enhanced Biosorption of Nickel Ions on Immobilized Surface-Engineered Yeast Using Nickel-Binding Peptides. Frontiers in Microbiology. 10 article 1254, 7 pp. (Jun. 2019) DOI: 10.3389/fmicb.2019.01254.

Maruthamuthu M. et al. Manganese and cobalt recovery by surface display of metal binding peptide on various loops of OmpC in *Escherichia coli*. J. Industrial Microbiology & Biotechnology. 45:31-41(2018) published Nov. 2017.

Oshiro S. et al. Binding behaviour of a 12-mer peptide and its tandem dimer to gymnospermae and angiospermae ignins. RSC Adv. 7:31338 (2017).

Rosmalen M. et al. Tuning the Flexibility of Glycine-Serine Linkers to Allow Rational Design of Multidomain Proteins. Biochemisty. 56, 50, 6565-6574 (2017).

Schonberger N. et al. Directed Evolution and Engineering of Gallium-Binding Phage Clones—A Preliminary Stud. Biomimetics 4(2) 35. DOI:10.3390/biomimetics4020035 (May 2019).

Tejada Vaprio R. E. Peptide-directed Nanoparticle Synthesis with a Denovo Pd-binding Sequence Fused to a Reporter Protein. Theses and Dissertations. 2393 (2017).

Urbina J. et al. A New Approach to Biomining: Bioengineering Surfaces for Metal Recovery From Aqueous Solution. Nature Scientific Reports. 9:16422 (Nov. 2019) DOI: 10.1038/S41598-019-52778-2.

Yamaguchi A. et al. Discovery of 12-mer peptides that bind to wood lignin. Nat. Scientific Reports. 6:21833 (2016).

Zhang H. et al. Systematic identification of arsenic-binding proteins reveals that hexokinase-2 is inhibited by arsenic. Pro. Natl. Acad Sci. (PNAS). 112(49): 15084-15089.

Zhang Y. et al. Tuning the autophagy-inducing activity of lanthanide-based nanocrystals through specific surface coating peptides. Nature Materials. 11:817-826 (2012).

NASA Innovative Advanced Concepts annual meeting, Presentation, Sep. 26, 2018.

Stanford-Brown-RISD wiki site, "Experiments" p. 24 pages, uploaded on Jul. 10, 2023. Retrieved from internet: https://2018.igem.org/Team:Stanford-Brown-RISD/Experiments.

Urbina, J. "Biomining: a Biological Approach to Recycling Elemental Components from End-of-Life Electronics", Mar. 7, 2019, https://escholarship.org/uc/item/2pz196t3.

Stanford-Brown-RISD wiki site, "Results" p. 31 pages, uploaded on Jul. 10, 2023. Retrieved from internet: https://2018.igem.org/Team:Stanford-Brown-RISD/Results.

Stanford-Brown-RISD wiki site, "Demonstrate" p. 8 pages, uploaded on Jul. 10, 2023. Retrieved from internet: https://2018.igem.org/Team:Stanford-Brown-RISD/Demonstrate.

Stanford-Brown-RISD wiki site, "Parts" p. 5 pages, uploaded on Jul. 10, 2023. Retrieved from internet: https://2018.igem.org/Team:Stanford-Brown-RISD/Parts.

Registry of Standard Biological Parts, Part:BBa_K2868019, 13 pages, uploaded on Jul. 10, 2023. Retrieved from internet: http://parts.igem.org/Part:BBa_K2868019.

Registry of Standard Biological Parts, Part:BBa_K2868014, 4 pages, uploaded on Jul. 10, 2023. Retrieved from internet: http://parts.igem.org/Part:BBa_K2868014.

Registry of Standard Biological Parts, Part:BBa_K2868015, 13 pages, uploaded on Jul. 10, 2023. Retrieved from internet: http://parts.igem.org/Part:BBa_K2868015.

Registry of Standard Biological Parts, Part:BBa_K2868018, 13 pages, uploaded on Jul. 10, 2023. Retrieved from internet: http://parts.igem.org/Part:BBa_K2868018.

Stanford-Brown-RISD wiki site, "Filter Notebook" p. 13 pages, uploaded on Jul. 7, 2023. Retrieved from internet: https://drive.google.com/file/d/1rSJEY6wSu7DNRDncaKUI2054LTFPJ2Ef/view.

\* cited by examiner

SEQUENCE LISTING

```
<160> NUMBER OF SEQ ID NOS: 73

<210> SEQ ID NO 1
<211> LENGTH: 7
<212> TYPE: PRT
<213> ORGANISM: artificial sequence
<220> FEATURE:
<223> OTHER INFORMATION: synthetic peptide

<400> SEQUENCE: 1

Cys Thr Thr Cys Gly Cys Gly
1               5

<210> SEQ ID NO 2
<211> LENGTH: 10
<212> TYPE: PRT
<213> ORGANISM: artificial sequence
<220> FEATURE:
<223> OTHER INFORMATION: synthetic peptide
```

-continued

<400> SEQUENCE: 2

Met Cys Thr Thr Cys Gly Cys Gly Glu Gly
1               5                   10

<210> SEQ ID NO 3
<211> LENGTH: 13
<212> TYPE: PRT
<213> ORGANISM: artificial sequence
<220> FEATURE:
<223> OTHER INFORMATION: synthetic peptide

<400> SEQUENCE: 3

Gly Phe His Gly Arg Ala Asp Ala Leu Leu His Lys Ile
1               5                   10

<210> SEQ ID NO 4
<211> LENGTH: 6
<212> TYPE: PRT
<213> ORGANISM: artificial sequence
<220> FEATURE:
<223> OTHER INFORMATION: synthetic peptide

<400> SEQUENCE: 4

His Cys Trp Cys His Met
1               5

<210> SEQ ID NO 5
<211> LENGTH: 20
<212> TYPE: PRT
<213> ORGANISM: artificial sequence
<220> FEATURE:
<223> OTHER INFORMATION: synthetic peptide

<400> SEQUENCE: 5

His Asn Leu Gly Met Asn His Asp Leu Gln Gly Glu Arg Pro Tyr Val
1               5                   10                  15

Thr Glu Gly Cys
            20

<210> SEQ ID NO 6
<211> LENGTH: 11
<212> TYPE: PRT
<213> ORGANISM: artificial sequence
<220> FEATURE:
<223> OTHER INFORMATION: synthetic peptide

<400> SEQUENCE: 6

Cys Pro Ser Glu Asp His Val Ser Gln Asp Lys
1               5                   10

<210> SEQ ID NO 7
<211> LENGTH: 18
<212> TYPE: PRT
<213> ORGANISM: artificial sequence
<220> FEATURE:
<223> OTHER INFORMATION: synthetic peptide

<400> SEQUENCE: 7

Lys Thr Glu Tyr Val Asp Glu Arg Ser Lys Ser Leu Thr Val Asp Leu
1               5                   10                  15

Thr Lys

<210> SEQ ID NO 8
<211> LENGTH: 18

```
<212> TYPE: PRT
<213> ORGANISM: artificial sequence
<220> FEATURE:
<223> OTHER INFORMATION: synthetic peptide

<400> SEQUENCE: 8

Lys Phe Phe Lys Asp Phe Arg His Lys Pro Ala Thr Glu Leu Thr His
1               5                   10                  15

Glu Asp

<210> SEQ ID NO 9
<211> LENGTH: 16
<212> TYPE: PRT
<213> ORGANISM: artificial sequence
<220> FEATURE:
<223> OTHER INFORMATION: synthetic peptide

<400> SEQUENCE: 9

His Asn Leu Gly Met Asn His Leu Gln Gly Arg Pro Val Thr Gly Cys
1               5                   10                  15

<210> SEQ ID NO 10
<211> LENGTH: 7
<212> TYPE: PRT
<213> ORGANISM: artificial sequence
<220> FEATURE:
<223> OTHER INFORMATION: synthetic peptide

<400> SEQUENCE: 10

Cys Pro His Val Ser Gln Lys
1               5

<210> SEQ ID NO 11
<211> LENGTH: 20
<212> TYPE: PRT
<213> ORGANISM: artificial sequence
<220> FEATURE:
<223> OTHER INFORMATION: synthetic peptide

<400> SEQUENCE: 11

His Asn Leu Gly Met Asn His Val Leu Gln Gly Asn Arg Pro Leu Val
1               5                   10                  15

Thr Gln Gly Cys
            20

<210> SEQ ID NO 12
<211> LENGTH: 11
<212> TYPE: PRT
<213> ORGANISM: artificial sequence
<220> FEATURE:
<223> OTHER INFORMATION: synthetic peptide

<400> SEQUENCE: 12

Cys Pro Asn Leu Gly His Val Ser Gln Asn Lys
1               5                   10

<210> SEQ ID NO 13
<211> LENGTH: 40
<212> TYPE: PRT
<213> ORGANISM: artificial sequence
<220> FEATURE:
<223> OTHER INFORMATION: synthetic peptide

<400> SEQUENCE: 13

His Asn Leu Gly Met Asn His Val His Asn Leu Gly Met Asn His Val
1               5                   10                  15
```

Leu Gln Gly Asn Arg Pro Leu Val Thr Gln Gly Cys Leu Gln Gly Asn
                20                  25                  30

Arg Pro Leu Val Thr Gln Gly Cys
        35                  40

<210> SEQ ID NO 14
<211> LENGTH: 60
<212> TYPE: PRT
<213> ORGANISM: artificial sequence
<220> FEATURE:
<223> OTHER INFORMATION: synthetic peptide

<400> SEQUENCE: 14

His Asn Leu Gly Met Asn His Val Leu Gln Gly Asn Arg Pro Leu Val
1               5                   10                  15

Thr Gln Gly Cys His Asn Leu Gly Met Asn His Val Leu Gln Gly Asn
                20                  25                  30

Arg Pro Leu Val Thr Gln Gly Cys His Asn Leu Gly Met Asn His Val
        35                  40                  45

Leu Gln Gly Asn Arg Pro Leu Val Thr Gln Gly Cys
    50                  55                  60

<210> SEQ ID NO 15
<211> LENGTH: 26
<212> TYPE: PRT
<213> ORGANISM: artificial sequence
<220> FEATURE:
<223> OTHER INFORMATION: synthetic peptide

<400> SEQUENCE: 15

Gly Ser Gly Gly Ser Gly His Asn Leu Gly Met Asn His Val Leu Gln
1               5                   10                  15

Gly Asn Arg Pro Leu Val Thr Gln Gly Cys
                20                  25

<210> SEQ ID NO 16
<211> LENGTH: 52
<212> TYPE: PRT
<213> ORGANISM: artificial sequence
<220> FEATURE:
<223> OTHER INFORMATION: synthetic peptide

<400> SEQUENCE: 16

Gly Ser Gly Gly Ser Gly His Asn Leu Gly Met Asn His Val Leu Gln
1               5                   10                  15

Gly Asn Arg Pro Leu Val Thr Gln Gly Cys Gly Ser Gly Gly Ser Gly
                20                  25                  30

His Asn Leu Gly Met Asn His Val Leu Gln Gly Asn Arg Pro Leu Val
        35                  40                  45

Thr Gln Gly Cys
    50

<210> SEQ ID NO 17
<211> LENGTH: 78
<212> TYPE: PRT
<213> ORGANISM: artificial sequence
<220> FEATURE:
<223> OTHER INFORMATION: synthetic peptide

<400> SEQUENCE: 17

Gly Ser Gly Gly Ser Gly His Asn Leu Gly Met Asn His Val Leu Gln
1               5                   10                  15

Gly Asn Arg Pro Leu Val Thr Gln Gly Cys Gly Ser Gly Gly Ser Gly
            20                  25                  30

His Asn Leu Gly Met Asn His Val Leu Gln Gly Asn Arg Pro Leu Val
        35                  40                  45

Thr Gln Gly Cys Gly Ser Gly Gly Ser Gly His Asn Leu Gly Met Asn
    50                  55                  60

His Val Leu Gln Gly Asn Arg Pro Leu Val Thr Gln Gly Cys
65                  70                  75

<210> SEQ ID NO 18
<211> LENGTH: 104
<212> TYPE: PRT
<213> ORGANISM: artificial sequence
<220> FEATURE:
<223> OTHER INFORMATION: synthetic peptide

<400> SEQUENCE: 18

Gly Ser Gly Gly Ser Gly His Asn Leu Gly Met Asn His Val Leu Gln
1               5                   10                  15

Gly Asn Arg Pro Leu Val Thr Gln Gly Cys Gly Ser Gly Gly Ser Gly
            20                  25                  30

His Asn Leu Gly Met Asn His Val Leu Gln Gly Asn Arg Pro Leu Val
        35                  40                  45

Thr Gln Gly Cys Gly Ser Gly Gly Ser Gly His Asn Leu Gly Met Asn
    50                  55                  60

His Val Leu Gln Gly Asn Arg Pro Leu Val Thr Gln Gly Cys Gly Ser
65                  70                  75                  80

Gly Gly Ser Gly His Asn Leu Gly Met Asn His Val Leu Gln Gly Asn
                85                  90                  95

Arg Pro Leu Val Thr Gln Gly Cys
            100

<210> SEQ ID NO 19
<211> LENGTH: 130
<212> TYPE: PRT
<213> ORGANISM: artificial sequence
<220> FEATURE:
<223> OTHER INFORMATION: synthetic peptide

<400> SEQUENCE: 19

Gly Ser Gly Gly Ser Gly His Asn Leu Gly Met Asn His Val Leu Gln
1               5                   10                  15

Gly Asn Arg Pro Leu Val Thr Gln Gly Cys Gly Ser Gly Gly Ser Gly
            20                  25                  30

His Asn Leu Gly Met Asn His Val Leu Gln Gly Asn Arg Pro Leu Val
        35                  40                  45

Thr Gln Gly Cys Gly Ser Gly Gly Ser Gly His Asn Leu Gly Met Asn
    50                  55                  60

His Val Leu Gln Gly Asn Arg Pro Leu Val Thr Gln Gly Cys Gly Ser
65                  70                  75                  80

Gly Gly Ser Gly His Asn Leu Gly Met Asn His Val Leu Gln Gly Asn
                85                  90                  95

Arg Pro Leu Val Thr Gln Gly Cys Gly Ser Gly Gly Ser Gly His Asn
            100                 105                 110

```
Leu Gly Met Asn His Val Leu Gln Gly Asn Arg Pro Leu Val Thr Gln
        115                 120                 125

Gly Cys
    130

<210> SEQ ID NO 20
<211> LENGTH: 156
<212> TYPE: PRT
<213> ORGANISM: artificial sequence
<220> FEATURE:
<223> OTHER INFORMATION: synthetic peptide

<400> SEQUENCE: 20

Gly Ser Gly Gly Ser Gly His Asn Leu Gly Met Asn His Val Leu Gln
1               5                   10                  15

Gly Asn Arg Pro Leu Val Thr Gln Gly Cys Gly Ser Gly Gly Ser Gly
            20                  25                  30

His Asn Leu Gly Met Asn His Val Leu Gln Gly Asn Arg Pro Leu Val
        35                  40                  45

Thr Gln Gly Cys Gly Ser Gly Gly Ser Gly His Asn Leu Gly Met Asn
    50                  55                  60

His Val Leu Gln Gly Asn Arg Pro Leu Val Thr Gln Gly Cys Gly Ser
65                  70                  75                  80

Gly Gly Ser Gly His Asn Leu Gly Met Asn His Val Leu Gln Gly Asn
                85                  90                  95

Arg Pro Leu Val Thr Gln Gly Cys Gly Ser Gly Gly Ser Gly His Asn
            100                 105                 110

Leu Gly Met Asn His Val Leu Gln Gly Asn Arg Pro Leu Val Thr Gln
        115                 120                 125

Gly Cys Gly Ser Gly Gly Ser Gly His Asn Leu Gly Met Asn His Val
    130                 135                 140

Leu Gln Gly Asn Arg Pro Leu Val Thr Gln Gly Cys
145                 150                 155

<210> SEQ ID NO 21
<211> LENGTH: 10
<212> TYPE: PRT
<213> ORGANISM: artificial sequence
<220> FEATURE:
<223> OTHER INFORMATION: synthetic peptide

<400> SEQUENCE: 21

Asp Glu His Gly Thr Ala Val Met Leu Lys
1               5                   10

<210> SEQ ID NO 22
<211> LENGTH: 12
<212> TYPE: PRT
<213> ORGANISM: artificial sequence
<220> FEATURE:
<223> OTHER INFORMATION: synthetic peptide

<400> SEQUENCE: 22

Ser Gly Val Tyr Lys Val Ala Tyr Asp Ala Ser Arg
1               5                   10

<210> SEQ ID NO 23
<211> LENGTH: 15
<212> TYPE: PRT
<213> ORGANISM: artificial sequence
<220> FEATURE:
```

-continued

```
<223> OTHER INFORMATION: synthetic peptide

<400> SEQUENCE: 23

Gly Val Ile His Arg Asn Asp Gln Trp Thr Ala Pro Gly Gly Gly
1               5                   10                  15

<210> SEQ ID NO 24
<211> LENGTH: 10
<212> TYPE: PRT
<213> ORGANISM: artificial sequence
<220> FEATURE:
<223> OTHER INFORMATION: synthetic peptide

<400> SEQUENCE: 24

Glu Asp Gly Glu Glu Cys Asp Cys Gly Glu
1               5                   10

<210> SEQ ID NO 25
<211> LENGTH: 10
<212> TYPE: PRT
<213> ORGANISM: artificial sequence
<220> FEATURE:
<223> OTHER INFORMATION: synthetic peptide

<400> SEQUENCE: 25

Thr Arg Ser Arg Ser His Thr Ser Glu Gly
1               5                   10

<210> SEQ ID NO 26
<211> LENGTH: 20
<212> TYPE: PRT
<213> ORGANISM: artificial sequence
<220> FEATURE:
<223> OTHER INFORMATION: synthetic peptide

<400> SEQUENCE: 26

Met Cys Val Asn Met Glu Trp Gly Ala Phe Gly Asp Asn Gly Cys Leu
1               5                   10                  15

Asp Asp Phe Arg
            20

<210> SEQ ID NO 27
<211> LENGTH: 6
<212> TYPE: PRT
<213> ORGANISM: artificial sequence
<220> FEATURE:
<223> OTHER INFORMATION: synthetic peptide

<400> SEQUENCE: 27

Arg Lys Leu Pro Asp Ala
1               5

<210> SEQ ID NO 28
<211> LENGTH: 12
<212> TYPE: PRT
<213> ORGANISM: artificial sequence
<220> FEATURE:
<223> OTHER INFORMATION: synthetic peptide

<400> SEQUENCE: 28

Thr Ser Asn Ala Val His Pro Thr Leu Arg His Leu
1               5                   10

<210> SEQ ID NO 29
<211> LENGTH: 13
<212> TYPE: PRT
```

-continued

```
<213> ORGANISM: artificial sequence
<220> FEATURE:
<223> OTHER INFORMATION: synthetic peptide

<400> SEQUENCE: 29

Gly Asn Leu His Thr Ser Ala Thr Asn Leu Tyr Leu His
1               5                   10

<210> SEQ ID NO 30
<211> LENGTH: 32
<212> TYPE: PRT
<213> ORGANISM: artificial sequence
<220> FEATURE:
<223> OTHER INFORMATION: synthetic peptide

<400> SEQUENCE: 30

Phe Ile Asp Thr Asn Asn Asp Gly Trp Ile Glu Gly Asp Glu Leu Phe
1               5                   10                  15

Ile Asp Thr Asn Asn Asp Gly Trp Ile Glu Gly Asp Glu Leu Leu Ala
            20                  25                  30

<210> SEQ ID NO 31
<211> LENGTH: 12
<212> TYPE: PRT
<213> ORGANISM: artificial sequence
<220> FEATURE:
<223> OTHER INFORMATION: synthetic peptide

<400> SEQUENCE: 31

Thr Met His His Ala Ala Ile Ala His Pro Pro His
1               5                   10

<210> SEQ ID NO 32
<211> LENGTH: 17
<212> TYPE: PRT
<213> ORGANISM: artificial sequence
<220> FEATURE:
<223> OTHER INFORMATION: synthetic peptide

<400> SEQUENCE: 32

Glx Gly Pro Trp Leu Glu Glu Glu Glu Ala Tyr Gly Trp Met Asp
1               5                   10                  15

Phe

<210> SEQ ID NO 33
<211> LENGTH: 16
<212> TYPE: PRT
<213> ORGANISM: artificial sequence
<220> FEATURE:
<223> OTHER INFORMATION: synthetic peptide

<400> SEQUENCE: 33

Thr Ser Thr Gln Cys Pro Ser His Ile Arg Ala Cys Leu Lys Lys Arg
1               5                   10                  15

<210> SEQ ID NO 34
<211> LENGTH: 8
<212> TYPE: PRT
<213> ORGANISM: artificial sequence
<220> FEATURE:
<223> OTHER INFORMATION: synthetic peptide

<400> SEQUENCE: 34

Arg Cys Gln Tyr Pro Leu Cys Ser
1               5
```

<210> SEQ ID NO 35
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION

<400> SEQUENCE: 35

Asp Val Asp Ala
1

<210> SEQ ID NO 36
<211> LENGTH: 79
<212> TYPE: PRT
<213> ORGANISM: artificial sequence
<220> FEATURE:
<223> OTHER INFORMATION: synthetic peptide

<400> SEQUENCE: 36

Leu Asp Cys Arg Glu Arg Ile Glu Lys Asp Leu Glu Asp Leu Glu Lys
1               5                   10                  15

Glu Leu Met Glu Met Lys Ser Ile Lys Leu Ser Asp Asp Glu Glu Ala
            20                  25                  30

Val Val Glu Arg Ala Leu Asn Tyr Arg Asp Asp Ser Val Tyr Tyr Leu
        35                  40                  45

Glu Lys Gly Asp His Ile Thr Ser Phe Gly Cys Ile Thr Tyr Ala Glu
    50                  55                  60

Gly Leu Leu Asp Ser Leu Arg Met Leu His Arg Ile Ile Glu Gly
65                  70                  75

<210> SEQ ID NO 37
<211> LENGTH: 15
<212> TYPE: PRT
<213> ORGANISM: artificial sequence
<220> FEATURE:
<223> OTHER INFORMATION: synthetic peptide

<400> SEQUENCE: 37

Ser Cys Leu Trp Gly Asp Val Ser Glu Leu Asp Phe Leu Cys Ser
1               5                   10                  15

<210> SEQ ID NO 38
<211> LENGTH: 14
<212> TYPE: PRT
<213> ORGANISM: artificial sequence
<220> FEATURE:
<223> OTHER INFORMATION: synthetic peptide

<400> SEQUENCE: 38

Ser Cys Leu Tyr Pro Ser Trp Ser Asp Tyr Ala Phe Cys Ser
1               5                   10

<210> SEQ ID NO 39
<211> LENGTH: 16
<212> TYPE: PRT
<213> ORGANISM: artificial sequence
<220> FEATURE:
<223> OTHER INFORMATION: synthetic peptide

```
<400> SEQUENCE: 39

Ser Cys Pro Val Trp Phe Ser Asp Val Gly Asp Phe Met Val Cys Ser
1               5                   10                  15

<210> SEQ ID NO 40
<211> LENGTH: 11
<212> TYPE: PRT
<213> ORGANISM: artificial sequence
<220> FEATURE:
<223> OTHER INFORMATION: synthetic peptide

<400> SEQUENCE: 40

Ala Cys Thr Ala Arg Ser Pro Trp Ile Cys Gly
1               5                   10

<210> SEQ ID NO 41
<211> LENGTH: 11
<212> TYPE: PRT
<213> ORGANISM: artificial sequence
<220> FEATURE:
<223> OTHER INFORMATION: synthetic peptide

<400> SEQUENCE: 41

Ala Cys Trp Pro Ala Thr Arg Ile Ser Cys Gly
1               5                   10

<210> SEQ ID NO 42
<211> LENGTH: 11
<212> TYPE: PRT
<213> ORGANISM: artificial sequence
<220> FEATURE:
<223> OTHER INFORMATION: synthetic peptide

<400> SEQUENCE: 42

Ala Cys Thr Ala Ala Ser Pro Trp Ile Cys Gly
1               5                   10

<210> SEQ ID NO 43
<211> LENGTH: 11
<212> TYPE: PRT
<213> ORGANISM: artificial sequence
<220> FEATURE:
<223> OTHER INFORMATION: synthetic peptide

<400> SEQUENCE: 43

Ala Cys Thr Ala Arg Ser Pro Trp Ala Cys Gly
1               5                   10

<210> SEQ ID NO 44
<211> LENGTH: 52
<212> TYPE: PRT
<213> ORGANISM: artificial sequence
<220> FEATURE:
<223> OTHER INFORMATION: synthetic peptide

<400> SEQUENCE: 44

Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln
    50
```

<210> SEQ ID NO 45
<211> LENGTH: 30
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (30)..(30)
<223> OTHER INFORMATION: Xaa is Arg or is absent

<400> SEQUENCE: 45

Val Gly Glu Cys Val Arg Gly Arg Cys Pro Ser Gly Met Cys Cys Ser
1               5                   10                  15

Gln Phe Gly Tyr Cys Gly Lys Gly Pro Lys Tyr Cys Gly Xaa
            20                  25                  30

<210> SEQ ID NO 46
<211> LENGTH: 41
<212> TYPE: PRT
<213> ORGANISM: artificial sequence
<220> FEATURE:
<223> OTHER INFORMATION: synthetic peptide

<400> SEQUENCE: 46

Gln Thr Cys Ala Ser Arg Cys Pro Arg Pro Cys Asn Ala Gly Leu Cys
1               5                   10                  15

Cys Ser Ile Tyr Gly Tyr Cys Gly Ser Gly Asn Ala Tyr Cys Gly Ala
            20                  25                  30

Gly Asn Cys Arg Cys Gln Cys Arg Gly
            35                  40

<210> SEQ ID NO 47
<211> LENGTH: 45
<212> TYPE: PRT
<213> ORGANISM: artificial sequence
<220> FEATURE:
<223> OTHER INFORMATION: synthetic peptide

<400> SEQUENCE: 47

Ala Trp Gln Val Asn Thr Ala Tyr Thr Ala Gly Gln Leu Val Thr Tyr
1               5                   10                  15

Asn Gly Lys Thr Tyr Lys Cys Leu Gln Pro His Thr Ser Leu Ala Gly
            20                  25                  30

Trp Glu Pro Ser Asn Val Pro Ala Leu Trp Gln Leu Gln
            35                  40                  45

<210> SEQ ID NO 48
<211> LENGTH: 47
<212> TYPE: PRT
<213> ORGANISM: artificial sequence
<220> FEATURE:
<223> OTHER INFORMATION: synthetic peptide

<400> SEQUENCE: 48

Ala Ala Gln Trp Gln Ala Gly Thr Ala Tyr Lys Gln Gly Asp Leu Val
1               5                   10                  15

Thr Tyr Leu Asn Lys Asp Tyr Glu Cys Ile Gln Pro His Thr Ala Leu
            20                  25                  30

Thr Gly Trp Glu Pro Ser Asn Val Pro Ala Leu Trp Lys Tyr Val
            35                  40                  45

<210> SEQ ID NO 49
<211> LENGTH: 47
<212> TYPE: PRT
<213> ORGANISM: artificial sequence
<220> FEATURE:
<223> OTHER INFORMATION: synthetic peptide

<400> SEQUENCE: 49

Ala Ala Thr Trp Ser Ser Ser Thr Ala Tyr Asn Gly Gly Ala Thr Val
1               5                   10                  15

Ala Tyr Asn Gly His Asn Tyr Gln Ala Lys Trp Trp Thr Gln Gly Asn
            20                  25                  30

Val Pro Ser Ser Ser Thr Gly Asp Gly Gln Pro Trp Ala Asp Leu
        35                  40                  45

<210> SEQ ID NO 50
<211> LENGTH: 41
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is Met or is absent

<400> SEQUENCE: 50

Xaa Ser Ser Asn Gly Thr Ala Tyr Arg Phe Asp Cys Ser Lys Gly Leu
1               5                   10                  15

His Trp Asp Met Ser Leu Asn Thr Cys Asn Trp Pro Asp Ala Ala Gly
            20                  25                  30

Arg Val Glu Gly Asp His Leu Leu Pro
        35                  40

<210> SEQ ID NO 51
<211> LENGTH: 36
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is Met or is absent

<400> SEQUENCE: 51

Xaa Lys Leu Asn Lys Ile Thr Leu Leu Thr Gly Leu Ala Leu Leu Val
1               5                   10                  15

Ser Ser Glu Ala Tyr Ser His Gly Tyr Val Glu Ser Pro Ala Phe Ser
            20                  25                  30

Cys Ile Ile Met
        35

<210> SEQ ID NO 52
<211> LENGTH: 40
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is Met or is absent

```
<400> SEQUENCE: 52

Xaa Thr Thr Val His Gln Gly Thr Met Pro Ser Gly Lys Thr Gly Arg
1               5                   10                  15

His Met Ile Leu Ala Val Trp Thr Val Asn Asp Thr Pro Met Ala Phe
            20                  25                  30

Tyr Ser Cys Ser Asp Val Gln Phe
        35                  40

<210> SEQ ID NO 53
<211> LENGTH: 64
<212> TYPE: PRT
<213> ORGANISM: artificial sequence
<220> FEATURE:
<223> OTHER INFORMATION: synthetic peptide

<400> SEQUENCE: 53

Ser Lys Phe Arg Thr Glu Cys Asn Thr Ala Arg Gly Lys Gly His Met
1               5                   10                  15

Leu Ile Ala Tyr Pro Gly Asp Cys Ser Gln Tyr Ile Ser Cys Asp Ser
            20                  25                  30

Asn Asp Gln Ser Pro Gln Gln Cys Ala Ser Gly Thr Val Phe Asn Ser
        35                  40                  45

Glu Lys Gln Arg Cys Asp Phe Arg Ala Asn Val Pro Ser Cys Lys Val
    50                  55                  60

<210> SEQ ID NO 54
<211> LENGTH: 32
<212> TYPE: PRT
<213> ORGANISM: artificial sequence
<220> FEATURE:
<223> OTHER INFORMATION: synthetic peptide

<400> SEQUENCE: 54

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 55
<211> LENGTH: 43
<212> TYPE: PRT
<213> ORGANISM: artificial sequence
<220> FEATURE:
<223> OTHER INFORMATION: synthetic peptide

<400> SEQUENCE: 55

Met Asn Ala Ser Tyr Asn Gly Thr Leu Ala Pro Asn Ala Asn Val Thr
1               5                   10                  15

Ile Gly Tyr Gln Ala Ser His Ser Gly Asn Ser Ala Ala Pro Gly Ala
            20                  25                  30

Cys Thr Leu Asn Gly Thr Thr Cys Ala Val Gly
        35                  40

<210> SEQ ID NO 56
<211> LENGTH: 45
<212> TYPE: PRT
<213> ORGANISM: artificial sequence
<220> FEATURE:
<223> OTHER INFORMATION: synthetic peptide
```

<400> SEQUENCE: 56

Ile Ser Gly Thr Val Asn Asn Leu Trp Asn Ala Thr Trp Lys Gln Ser
1               5                   10                  15

Gly Thr Thr Leu Ser Ala Ser Gly Val Asp Trp Asn Lys Thr Leu Ala
                20                  25                  30

Pro Gly Ala Thr Ala Glu Phe Gly Phe Cys Ala Ala Arg
                35                  40                  45

<210> SEQ ID NO 57
<211> LENGTH: 44
<212> TYPE: PRT
<213> ORGANISM: artificial sequence
<220> FEATURE:
<223> OTHER INFORMATION: synthetic peptide

<400> SEQUENCE: 57

Met Ala Thr Gln Ser His Trp Gly Gln Cys Gly Gly Ile Gly Tyr Ser
1               5                   10                  15

Gly Pro Thr Val Cys Ala Ser Gly Thr Thr Cys Gln Val Leu Asn Pro
                20                  25                  30

Tyr Tyr Ser Gln Cys Leu Pro Thr Thr Pro Thr Gly
                35                  40

<210> SEQ ID NO 58
<211> LENGTH: 40
<212> TYPE: PRT
<213> ORGANISM: artificial sequence
<220> FEATURE:
<223> OTHER INFORMATION: synthetic peptide

<400> SEQUENCE: 58

Ala Glu Cys Ser Lys Leu Tyr Gly Gln Cys Gly Gly Lys Asn Trp Asn
1               5                   10                  15

Gly Pro Thr Cys Cys Glu Ser Gly Ser Thr Cys Lys Val Ser Asn Asp
                20                  25                  30

Tyr Tyr Ser Gln Cys Leu Pro Ser
                35                  40

<210> SEQ ID NO 59
<211> LENGTH: 36
<212> TYPE: PRT
<213> ORGANISM: artificial sequence
<220> FEATURE:
<223> OTHER INFORMATION: synthetic peptide

<400> SEQUENCE: 59

Thr Gln Ser His Tyr Gly Gln Cys Gly Gly Ile Gly Tyr Ser Gly Pro
1               5                   10                  15

Thr Val Cys Ala Ser Gly Thr Thr Cys Gln Val Leu Asn Pro Tyr Tyr
                20                  25                  30

Ser Gln Cys Leu
                35

<210> SEQ ID NO 60
<211> LENGTH: 88
<212> TYPE: PRT
<213> ORGANISM: artificial sequence
<220> FEATURE:
<223> OTHER INFORMATION: synthetic peptide

<400> SEQUENCE: 60

Thr Gly Ser Cys Ser Val Ser Ala Val Arg Gly Glu Glu Trp Ala Asp
1               5                   10                  15

Arg Phe Asn Val Thr Tyr Ser Val Ser Gly Ser Ser Ser Trp Val Val
                20                  25                  30

Thr Leu Gly Leu Asn Gly Gly Gln Ser Val Gln Ser Ser Trp Asn Ala
            35                  40                  45

Ala Leu Thr Gly Ser Ser Gly Thr Val Thr Ala Arg Pro Asn Gly Ser
        50                  55                  60

Gly Asn Ser Phe Gly Val Thr Phe Tyr Lys Asn Gly Ser Ser Ala Thr
65                  70                  75                  80

Pro Gly Ala Thr Cys Ala Thr Gly
                85

<210> SEQ ID NO 61
<211> LENGTH: 12
<212> TYPE: PRT
<213> ORGANISM: artificial sequence
<220> FEATURE:
<223> OTHER INFORMATION: synthetic peptide

<400> SEQUENCE: 61

His Phe Pro Ser Pro Ile Phe Gln Arg His Ser His
1               5                   10

<210> SEQ ID NO 62
<211> LENGTH: 25
<212> TYPE: PRT
<213> ORGANISM: artificial sequence
<220> FEATURE:
<223> OTHER INFORMATION: synthetic peptide

<400> SEQUENCE: 62

His Phe Pro Ser Pro Ile Phe Gln Arg His Ser His Gly His Phe Pro
1               5                   10                  15

Ser Pro Ile Phe Gln Arg His Ser His
            20                  25

<210> SEQ ID NO 63
<211> LENGTH: 12
<212> TYPE: PRT
<213> ORGANISM: artificial sequence
<220> FEATURE:
<223> OTHER INFORMATION: synthetic peptide

<400> SEQUENCE: 63

Val Gln His Asn Thr Lys Tyr Ser Val Val Ile Arg
1               5                   10

<210> SEQ ID NO 64
<211> LENGTH: 12
<212> TYPE: PRT
<213> ORGANISM: artificial sequence
<220> FEATURE:
<223> OTHER INFORMATION: synthetic peptide

<400> SEQUENCE: 64

Tyr His Pro Asn Gly Met Asn Pro Tyr Thr Lys Ala
1               5                   10

<210> SEQ ID NO 65
<211> LENGTH: 78

```
<212> TYPE: PRT
<213> ORGANISM: artificial sequence
<220> FEATURE:
<223> OTHER INFORMATION: synthetic peptide

<400> SEQUENCE: 65

Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln Gly Ser Gly Gly Ser Gly His Asn Leu Gly Met Asn
    50                  55                  60

His Val Leu Gln Gly Asn Arg Pro Leu Val Thr Gln Gly Cys
65                  70                  75

<210> SEQ ID NO 66
<211> LENGTH: 104
<212> TYPE: PRT
<213> ORGANISM: artificial sequence
<220> FEATURE:
<223> OTHER INFORMATION: synthetic peptide

<400> SEQUENCE: 66

Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln Gly Ser Gly Gly Ser Gly His Asn Leu Gly Met Asn
    50                  55                  60

His Val Leu Gln Gly Asn Arg Pro Leu Val Thr Gln Gly Cys Gly Ser
65                  70                  75                  80

Gly Gly Ser Gly His Asn Leu Gly Met Asn His Val Leu Gln Gly Asn
                85                  90                  95

Arg Pro Leu Val Thr Gln Gly Cys
            100

<210> SEQ ID NO 67
<211> LENGTH: 130
<212> TYPE: PRT
<213> ORGANISM: artificial sequence
<220> FEATURE:
<223> OTHER INFORMATION: synthetic peptide

<400> SEQUENCE: 67

Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln Gly Ser Gly Gly Ser Gly His Asn Leu Gly Met Asn
    50                  55                  60

His Val Leu Gln Gly Asn Arg Pro Leu Val Thr Gln Gly Cys Gly Ser
65                  70                  75                  80
```

```
Gly Gly Ser Gly His Asn Leu Gly Met Asn His Val Leu Gln Gly Asn
            85                  90                  95

Arg Pro Leu Val Thr Gln Gly Cys Gly Ser Gly Ser Gly His Asn
        100                 105                 110

Leu Gly Met Asn His Val Leu Gln Gly Asn Arg Pro Leu Val Thr Gln
        115                 120                 125

Gly Cys
    130
```

<210> SEQ ID NO 68
<211> LENGTH: 156
<212> TYPE: PRT
<213> ORGANISM: artificial sequence
<220> FEATURE:
<223> OTHER INFORMATION: synthetic peptide

<400> SEQUENCE: 68

```
Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln Gly Ser Gly Ser Gly His Asn Leu Gly Met Asn
50                  55                  60

His Val Leu Gln Gly Asn Arg Pro Leu Val Thr Gln Gly Cys Gly Ser
65                  70                  75                  80

Gly Gly Ser Gly His Asn Leu Gly Met Asn His Val Leu Gln Gly Asn
            85                  90                  95

Arg Pro Leu Val Thr Gln Gly Cys Gly Ser Gly Ser Gly His Asn
        100                 105                 110

Leu Gly Met Asn His Val Leu Gln Gly Asn Arg Pro Leu Val Thr Gln
        115                 120                 125

Gly Cys Gly Ser Gly Gly Ser Gly His Asn Leu Gly Met Asn His Val
        130                 135                 140

Leu Gln Gly Asn Arg Pro Leu Val Thr Gln Gly Cys
145                 150                 155
```

<210> SEQ ID NO 69
<211> LENGTH: 182
<212> TYPE: PRT
<213> ORGANISM: artificial sequence
<220> FEATURE:
<223> OTHER INFORMATION: synthetic peptide

<400> SEQUENCE: 69

```
Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln Gly Ser Gly Ser Gly His Asn Leu Gly Met Asn
50                  55                  60

His Val Leu Gln Gly Asn Arg Pro Leu Val Thr Gln Gly Cys Gly Ser
65                  70                  75                  80
```

```
Gly Gly Ser Gly His Asn Leu Gly Met Asn His Val Leu Gln Gly Asn
            85                  90                  95

Arg Pro Leu Val Thr Gln Gly Cys Gly Ser Gly Ser Gly His Asn
        100                 105                 110

Leu Gly Met Asn His Val Leu Gln Gly Asn Arg Pro Leu Val Thr Gln
        115                 120                 125

Gly Cys Gly Ser Gly Ser Gly His Asn Leu Gly Met Asn His Val
130                 135                 140

Leu Gln Gly Asn Arg Pro Leu Val Thr Gln Gly Cys Gly Ser Gly Gly
145                 150                 155                 160

Ser Gly His Asn Leu Gly Met Asn His Val Leu Gln Gly Asn Arg Pro
                165                 170                 175

Leu Val Thr Gln Gly Cys
        180
```

<210> SEQ ID NO 70
<211> LENGTH: 208
<212> TYPE: PRT
<213> ORGANISM: artificial sequence
<220> FEATURE:
<223> OTHER INFORMATION: synthetic peptide

<400> SEQUENCE: 70

```
Thr Thr Asn Pro Gly Val Ser Ala Trp Gln Val Asn Thr Ala Tyr Thr
1               5                   10                  15

Ala Gly Gln Leu Val Thr Tyr Asn Gly Lys Thr Tyr Lys Cys Leu Gln
            20                  25                  30

Pro His Thr Ser Leu Ala Gly Trp Glu Pro Ser Asn Val Pro Ala Leu
        35                  40                  45

Trp Gln Leu Gln Gly Ser Gly Ser Gly His Asn Leu Gly Met Asn
    50                  55                  60

His Val Leu Gln Gly Asn Arg Pro Leu Val Thr Gln Gly Cys Gly Ser
65                  70                  75                  80

Gly Gly Ser Gly His Asn Leu Gly Met Asn His Val Leu Gln Gly Asn
            85                  90                  95

Arg Pro Leu Val Thr Gln Gly Cys Gly Ser Gly Ser Gly His Asn
        100                 105                 110

Leu Gly Met Asn His Val Leu Gln Gly Asn Arg Pro Leu Val Thr Gln
        115                 120                 125

Gly Cys Gly Ser Gly Ser Gly His Asn Leu Gly Met Asn His Val
130                 135                 140

Leu Gln Gly Asn Arg Pro Leu Val Thr Gln Gly Cys Gly Ser Gly Gly
145                 150                 155                 160

Ser Gly His Asn Leu Gly Met Asn His Val Leu Gln Gly Asn Arg Pro
                165                 170                 175

Leu Val Thr Gln Gly Cys Gly Ser Gly Ser Gly His Asn Leu Gly
        180                 185                 190

Met Asn His Val Leu Gln Gly Asn Arg Pro Leu Val Thr Gln Gly Cys
        195                 200                 205
```

<210> SEQ ID NO 71
<211> LENGTH: 5
<212> TYPE: PRT
<213> ORGANISM: artificial sequence
<220> FEATURE:
<223> OTHER INFORMATION: synthetic peptide

```
-continued

<400> SEQUENCE: 71

Gly Gly Ser Gly Gly
1               5

<210> SEQ ID NO 72
<211> LENGTH: 5
<212> TYPE: PRT
<213> ORGANISM: artificial sequence
<220> FEATURE:
<223> OTHER INFORMATION: synthetic peptide

<400> SEQUENCE: 72

Gly Gly Gly Gly Ser
1               5

<210> SEQ ID NO 73
<211> LENGTH: 6
<212> TYPE: PRT
<213> ORGANISM: artificial sequence
<220> FEATURE:
<223> OTHER INFORMATION: synthetic peptide

<400> SEQUENCE: 73

Gly Ser Gly Gly Ser Gly
1               5
```

FUNCTIONALIZING BIOLOGICAL SUBSTRATES WITH BIOENGINEERED PEPTIDES TO BIND TARGETED MOLECULES

CROSS-REFERENCE TO RELATED APPLICATIONS

This application claims the benefit of U.S. Provisional application U.S. 62/916,179, filed Oct. 16, 2019, which is incorporated by reference herein in its entirety.

ORIGIN OF THE INVENTION

The invention described herein was made in the performance of work under a NASA contract and by (an) employee(s) of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor has elected not to retain title.

REFERENCE TO A SEQUENCE LISTING

A sequence listing containing SEQ ID NOs: 1-73 is provided herewith in a computer-readable nucleotide/amino acid .txt file and is specifically incorporated by reference herein.

FIELD OF THE INVENTION FIELD OF THE INVENTION

The invention is in the field of remediation of potentially harmful chemical species from solution environments employing non-naturally-occurring peptides and proteins to capture the target chemical species from solution. More specifically the invention relates to the capture and removal of metal species from solution, particularly aqueous solutions. Capture and filtering methods employing and materials containing fusion peptides and proteins are provided.

BACKGROUND OF THE INVENTION

End-of-life electronics waste (e-waste) production has been fueled by economic growth and the demand for faster, more efficient consumer electronics. The glass and metals in e-waste can be reused or recycled; however, developed countries tend to not recycle due to high labor costs and strict environmental regulation. Instead, e-waste accumulates in landfills or is exported to developing countries where it is recycled using primitive techniques such as open-air incineration or strong acid treatments for metal recovery, without regard for worker safety or environmental impact (Kuroda & Ueda, 2011; Ilyas et al., 2013). Additionally, many elemental components in e-waste such as the rare earth elements (REEs) and transition metals like titanium (Ti) are emerging as new contaminants that have never before existed in concentrated quantities sufficient to produce toxicity to organisms. These activities have led to severe heavy metal pollution in communities that handle e-waste as they are experiencing adverse health effects and toxicity to aquatic and terrestrial ecosystems.

Clean water is vital for human health, infrastructure, food and sanitation. Regularly filtered water supply, and access to clean water remain a challenge whether in space or on Earth. Sometimes remediation is the only option. Another challenge is metal acquisition, whether from waste electronics or lunar or Martian regolith. Development of economically viable alternatives for elemental recovery is essential for sustaining a balance between technological development and environmental responsibility.

Conventional extraction methods rely on energy-intensive processes and are inefficient when applied to recycling e-waste or waste streams that contains mixed materials and small amounts of metals. Applying a biological approach to resource extraction from e-waste (urban biomining) allows for metal extraction at ambient temperatures with lower environmental impacts and energy requirements than current approaches.

Microbial surface adsorption can aid in metal recovery from aqueous solutions containing metals from e-waste (Kuroda & Ueda, 2011); however, there is limited specificity because the surface functional groups will bind many cations with high affinity (Borrok & Fein, 2005; Navarrete et al. 2011). Studies have been reported that focused on the addition of metal-binding peptide tags onto bacterial surface proteins and they have shown to sequester more metal than controls; however, the tags offer limited specificity as to the metals that are adsorbed (Cruz, 2000; Prabhukumar et al., 2004; Stair & Holcombe, 2005; Yunus & Tsai, 2015; Park et al., 2016).

In principle, a biological approach to metal extraction using peptides should be exquisitely specific, because all cellular fluids contain a mixture of metal ions at different concentrations; yet metal cofactors are not easily replaced from their cognate metalloproteins by competing ions in the intracellular milieu. Metal coordination number (the ability to bind to a given number of ligands) and molecular geometry are shared properties between a ligand and its cognate metal and are proposed to be a key determinant of specificity (Dudev & Lim, 2014). A metalloprotein will bind a metal cofactor with amino acids in the primary coordination sphere that refers to the molecules that are attached directly to the metal, and that is optimal for the molecular geometry and coordination number of the cognate metal. The effects of the second and third coordination spheres consist of molecules that interact via hydrogen and Van der Waals interactions with the primary coordination sphere, and are those presumed to determine specificity for a metal co-factor. Computer-generated design that considers only the primary coordination sphere of a metal and the approximate steric compatibility of a scaffold protein can be used to introduce a selective binding site into a protein (Benson et al., 1998; Yang et al., 2003). It remains challenging to model metal specificity into de novo designed proteins due to substantial computational requirements (Nanda & Koder, 2010; Gutten & Rulisek, 2013).

Biopanning techniques, such as those using phage libraries, can be used to identify metal-binding peptides that are selective for a target metal and for identifying natural proteins that adsorb target metals (Nguyen et al, 2013; Maruyama et al., 2007; U.S. Pat. No. 7,659,362; Hatanaka et al., 2017; U.S. Pat. No. 10,377,795; Zhang et al. 2012).

There is a significant need in the art for an inexpensive biological approach to recover specific, targeted metals and other target materials in e-waste or other aqueous solutions that requires minimal input of resources, including energy. An approach that enables simple scale up to a level that could be successfully implemented in an environment with limited resources, such as on a space mission or on earth in developing countries with poor access to clean water, is of particular interest.

SUMMARY OF THE INVENTION

The invention provides a method of capturing a target substance or material (e.g., a metal, metal complex, non-metal toxin, dye, a metabolite, or small molecule drug) from solution by functionalizing a biological or biologically-derived substrate using a peptide configured to selectively bind to the target substance or material and to bind to the substrate. The target can be any chemical species dissolved or suspended in the solution. Capture of the target by the substrate can isolate and allow removal of the target substance from solution. In some embodiments, the invention provides a method of functionalizing biological substrates with naturally-occurring or bioengineered peptides to bind targeted chemical species. Binding of target substance to the peptide which in turn is bound to the substrate functions to capture the target substance. In some embodiments, the invention provides a method of functionalizing biological substrates with naturally-occurring or bioengineered peptides to bind targeted chemical species, including molecules or metals, for utilization in water filtration applications. In some embodiments, the invention provides a method of functionalizing biological substrates with naturally-occurring or bioengineered peptides to bind targeted chemical species, including molecules or metals, for recovery of targeted chemical species from solution, particularly aqueous solution. In some embodiments, the methods herein can be utilized for the removal or filtering of targeted chemical species from solution, particularly aqueous solution. In some embodiments, the methods herein can be utilized to reduce the amount of targeted chemical species in solution, particularly aqueous solution. In some embodiments, the methods herein can be utilized to remove the targeted chemical species from solution, particularly aqueous solution, to an undetectable level. In some embodiments, the methods herein can be utilized for the detection and/or identification of targeted chemical species in solution, particularly aqueous solution. In some embodiments, after target chemical species is captured on the substrate, the substrate is separated from contact with solution and the target is released from the substrate for collection. In some embodiments, the target chemical species contains a metal. In some embodiments, the target chemical species is a metal oxide or hydroxide. In some embodiments, the target chemical species comprises a metal ion.

In some embodiments, the invention is a cost-effective, scalable, completely biodegradable filtration system for waste metal recovery from aqueous solution by functionalizing a chitin-containing substrate with a peptide comprising a metal-binding domain (an amino acid sequence) and a chitin-binding domain (an amino acid sequence). In some embodiments, the metal-binding domain is selected from those having an amino acid sequence of any one of SEQ ID NOs: 1-10 or an amino acid sequence having 85% or higher sequence identity thereto. In some embodiments, the metal-binding domain is selected from those having an amino acid sequence of any one of SEQ ID NOs: 11-20 or an amino acid sequence having 85% or higher sequence identity thereto. In some embodiments, the metal-binding domain is selected from those having an amino acid sequence of any one of SEQ ID NOs: 30-43 or an amino acid sequence having 85% or higher sequence identity thereto. In some embodiments, the metal-binding domain binds to a transition metal. In some embodiments, the metal-binding domain binds to a rare earth or lanthanide group metal. In some embodiments, the metal-binding domain binds to a platinum group metal. In some embodiments, the metal-binding domain binds to copper, nickel, and/or zinc. In some embodiments, the metal-binding domain binds to one of manganese, nickel, molybdenum, chromium, cobalt, arsenic, titanium, palladium, neodymium, terbium, gallium, indium, lanthanum, praseodymium, or uranium.

In some embodiments, the biological or biologically-derived substrate is a carbohydrate substrate. In some embodiments, the carbohydrate is a carbohydrate substrate is a polysaccharide or comprises a polysaccharide. In some embodiments, the biological or biologically-derived substrate comprises a biological polymer, such as a polysaccharide. In some embodiments, the biological or biologically-derived substrate comprises cellulose, hemicellulose, xylan, chitin or lignin. In some embodiments, the biological or biologically-derived substrate is a plant or agricultural waste material comprising lignocellulose, cellulose, hemicellulose, xylan, or lignin. In some embodiments, the biological or biologically-derived substrate is a cellulose-containing substrate. In some embodiments, the biological or biologically-derived substrate is a chitin-containing substrate. In some embodiments, the biological or biologically-derived substrate is a chitin-containing substrate derived from shellfish waste, seafood waste or shrimp waste. In some embodiments, the biological or biologically-derived substrate is a chitin-containing substrate derived from a fungus. In some embodiments, the fungus is a unicellular or multicellular fungus. In some embodiments, the fungus is a *Basidomycetes*. In some embodiments, the fungus is an *Ascomycetes*. In some embodiments, the fungus is a mushroom. In some embodiments, the fungus is a polypore fungus. In some embodiments, the fungus is a species of *Gandoderma*. In some embodiments, the fungus is a strain of *Gandoderma lucidum*.

In some embodiments, the chitin-containing substrate comprises fungal hyphae. In some embodiments, the chitin-containing substrate is fungal mycelium. In some embodiments, the chitin-containing substrate comprises fungal mycelium. In some embodiments, the fungal mycelium is that of a mushroom. In some embodiments, the fungal mycelium is that of a polypore fungus. In some embodiments, the fungal mycelium is that of a *Basidiomycetes* fungus. In some embodiments, the fungal mycelium is that of an Ascomycetes fungus. In some embodiments, the fungal mycelium is that of a species of *Gandoderma*. In some embodiments, the fungal mycelium is that of a strain of *Gandoderma lucidum*.

In some embodiments, the invention provides a fusion peptide or protein comprising at least one metal-binding domain and at least one chitin-binding domain. In some embodiments, the fusion peptide or protein comprises two or more metal-binding domains. In some embodiments, the fusion peptide or protein comprises at least one metal-binding domain, at least one chitin-binding domain and at least one peptide spacer sequence. In some embodiments, the fusion peptide or protein comprises at least two metal-binding domains, at least one chitin-binding domain and at least one peptide spacer sequence. In some embodiments, the fusion peptide or protein comprises at least one peptide spacer sequence positioned between the sequences of at least two metal binding domains. In some embodiments, the fusion peptide or protein comprises at least one peptide spacer sequence positioned between the sequences of the metal binding domain or domains and the chitin-binding domain.

In some embodiments, the fusion peptide or protein comprises at least one metal-binding domain selected from those having an amino acid sequence of any one of SEQ ID NOs: 11-20 or an amino acid sequence having 85% or higher amino acid sequence identity thereto. In some embodiments, the fusion peptide or protein comprises at least one metal-binding domain selected from those having an amino acid sequence of any one of SEQ ID NOs: 11-20 or an amino acid sequence having 85% or higher amino acid sequence identity thereto and at least one carbohydrate-binding domain or an amino acid sequence having 85% or higher amino acid sequence identity therewith. In some embodiments, the carbohydrate-binding domain is one having an amino acid sequence of any one of SEQ ID NOs: 54-60 or an amino acid having 85% or higher sequence identity therewith. In some embodiments, the fusion peptide or protein comprises at least one metal-binding domain selected from those having an amino acid sequence of any one of SEQ ID NOs: 11-20 or an amino acid sequence having 85% or higher amino acid sequence identity thereto and at least one carbohydrate-binding domain or an amino acid sequence having 85% or higher amino acid sequence identity thereto and at least one peptide spacer sequence.

In some embodiments, the invention provides a chitin-containing substrate functionalized or derivatized with a fusion peptide or fusion protein comprising a metal-binding domain and a chitin-containing domain. In some embodiments, the invention provides a chitin-containing substrate derivatized with a fusion peptide or fusion protein comprising at least two metal-binding domains and a chitin-containing domain. In some embodiments, the invention provides a chitin-containing substrate derivatized with a fusion peptide or fusion protein comprising at least one metal-binding domain, at least one peptide spacer sequence and a chitin-containing domain.

In some embodiments, the invention provides fungal mycelium functionalized or derivatized with a fusion peptide or fusion protein comprising a metal-binding domain and a chitin-containing domain. In some embodiments, the invention provides fungal mycelium functionalized or derivatized with a fusion peptide or fusion protein comprising at least two metal-binding domains and a chitin-containing domain. In some embodiments, the invention provides fungal mycelium functionalized or derivatized with a fusion peptide or fusion protein comprising at least one metal-binding domain, at least one peptide spacer sequence and a chitin-containing domain. In some embodiments, the fungal mycelium is that of a mushroom. In some embodiments, the fungal mycelium is that of a polypore fungus. In some embodiments, the fungal mycelium is that of a Basidiomycetes fungus. In some embodiments, the fungal mycelium is that of an Ascomycetes fungus. In some embodiments, the fungal mycelium is that of a species of *Gandoderma*. In some embodiments, the fungal mycelium is that of a strain of *Gandoderma lucidum*.

In some embodiments, the invention provides a metal-binding domain selected from those having an amino acid sequence of any one of SEQ ID NO: 11-20 or a sequence having 85% or higher sequence identify thereto. In some embodiments, the invention provides a fusion peptide or protein comprising a metal-binding domain selected from those having an amino acid sequence of any one of SEQ ID NO: 11-20 or a sequence having 85% or higher sequence identify thereto and an amino acid sequence that binds to a biological or biologically-derived substrate. In some embodiments, the invention provides a fusion peptide or protein comprising a metal-binding domain selected from those having an amino acid sequence of any one of SEQ ID NO: 11-20 or a sequence having 85% or higher sequence identify thereto and an amino acid sequence that binds to a polysaccharide. In some embodiments, the invention provides a fusion peptide or protein comprising a metal-binding domain selected from those having an amino acid sequence of any one of SEQ ID NO: 11-20 or a sequence having 85% or higher sequence identify thereto and an amino acid sequence that binds to cellulose, hemicellulose or chitin. In some embodiments, the invention provides a fusion peptide or protein comprising a metal-binding domain selected from those having an amino acid sequence of any one of SEQ ID NO: 11-20 or a sequence having 85% or higher sequence identify thereto and an amino acid sequence that binds to lignin.

In some embodiments, the invention provides a biological or biologically-derived substrate derivatized with a peptide or protein comprising a metal-binding domain selected from those having an amino acid sequence of any one of SEQ ID NO: 11-20 or a sequence having 85% or higher sequence identify thereto. In some embodiments, the invention provides a biological or biologically-derived substrate derivatized with a fusion peptide or protein comprising a metal-binding domain selected from those having an amino acid sequence of any one of SEQ ID NO: 11-20 or a sequence having 85% or higher sequence identify thereto and an amino acid sequence that binds to the biological or biologically-derived substrate. In some embodiments, the invention provides a chitin-containing substrate derivatized with a peptide or protein comprising a metal-binding domain selected from those having an amino acid sequence of any one of SEQ ID NO: 11-20 or a sequence having 85% or higher sequence identify thereto. In some embodiments, the invention provides a chitin-containing substrate derivatized with a fusion peptide or protein comprising a metal-binding domain selected from those having an amino acid sequence of any one of SEQ ID NO: 11-20 or a sequence having 85% or higher sequence identify thereto and an amino acid sequence that binds to the chitin-containing substrate. In some embodiments, the invention provides a chitin-containing substrate derivatized with a fusion peptide or protein comprising a metal-binding domain selected from those having an amino acid sequence of any one of SEQ ID NO: 11-20 or a sequence having 85% or higher sequence identify thereto and an amino acid sequence of a chitin-binding domain. In some embodiments, the invention provides fungal mycelium derivatized with a fusion peptide or protein comprising a metal-binding domain selected from those having an amino acid sequence of any one of SEQ ID NO: 11-20 or a sequence having 85% or higher sequence identify thereto and an amino acid sequence of a chitin-binding domain. In some embodiments, the chitin-binding domain is an amino acid sequence of any one of SEQ ID NOs: 44 to 53 or an amino acid sequence having 85% or higher sequence identity therewith.

In some embodiments, the invention is a filtration system for waste metal recovery from solution comprising a chitin-containing substrate carrying a fusion peptide or fusion protein comprising a metal-binding domain and a chitin-binding domain. In some embodiments, the metal-binding domain binds to a transition metal. In some embodiments, the metal-binding domain binds to a rare earth metal. In some embodiments, the metal-binding domain binds to copper. In some embodiments, the metal-binding domain is selected from those having an amino acid sequence of any one of SEQ ID NOs: 1-10 or a sequence having 85% or higher sequence identify thereto In some embodiments, the metal-binding domain is selected from those having an amino acid sequence of any one of SEQ ID NOs: 11-20 or a sequence having 85% or higher sequence identify thereto.

In some embodiments, the chitin-binding domain is an amino acid sequence of any one of SEQ ID NOs: 44 to 53 or an amino acid sequence having 85% or higher sequence identity therewith. In some embodiments, the chitin-containing substrate is fungal mycelium. In some embodiments, the chitin-containing substrate is fungal mycelium of a unicellular or multicellular fungus. In some embodiments, the fungus is a mushroom. In some embodiments, the fungus is a species of *Gandoderma*. In some embodiments, the fungus is a strain of *Gandoderma lucidum*. In some embodiments, the fungal mycelium is formed into a selected shape by molding. In some embodiments, the fungal mycelium is grown within a mold of a selected shape and is thereby formed into that shape. In some embodiments, the molded and shaped fungal mycelium is dried. In some embodiments, the fungal mycelium is formed into a mycelium foam. In some embodiments, the fungal mycelium is formed into a substrate that is porous to water or aqueous solution.

In some embodiments, the fusion peptides or proteins of this invention are prepared by peptide or protein synthesis. In some embodiments, the fusion peptide or proteins of this invention are prepared by expression of nucleic acid constructs containing nucleic acid which encodes those fusion peptide or proteins. In some embodiments, the invention provides nucleic acids which encode metal-binding peptides, or fusion peptides or fusion proteins comprising such metal-binding peptides or which encode peptides or proteins having 85% or higher sequence identify to such peptides or proteins. In some embodiments, the invention provides nucleic acid vectors which comprise nucleic acids encoding the metal-binding peptides, fusion peptides and fusion proteins of the invention or which encode peptides or proteins having 85% or higher sequence identify thereto.

In some embodiments, fusion peptides or proteins herein comprise one or more flexible peptide linkers positioned between tandem repeats of metal-binding domains or between tandem repeats of substrate-binding domains or between a metal-binding domain and a substrate-binding domain. In some embodiments, more than one flexible linker is employed in a fusion peptide or protein herein and the one or more flexible linkers employed may have the same or different amino acid sequence. In some embodiments, the flexible linkers are selected from those having the amino acids sequence of any of SEQ ID NOs:71-73 or those having 2-6 tandem repeats thereof.

In some embodiments, the fusion peptides or proteins useful in this invention are those having amino acid sequences of SEQ ID NOs: 65-70 or amino acids having 85% or higher sequence identity therewith. In some embodiments, the invention provides, nucleic acids encoding the amino acid sequences of SEQ ID NOs: 65-70 or amino acids having 85% or higher sequence identity therewith.

Other aspects and embodiments of the invention will be apparent on review of the non-limiting drawings, non-limiting detailed description and non-limiting examples herein.

BRIEF DESCRIPTION OF THE DRAWINGS

FIGS. 1-1C: Raw data and isotherms for tested peptides and Cu. The natural HypB peptides (FIG. 1A, left and center) had a range of affinities with Ka=(2.37±0.7)×106 M−1 and (1.30±0.07)×106 M−1, for HypB1 and HypB2, respectively. The HypB peptide was tested with and without leading and trailing residues and showed that the addition or absence of the amino acids at the N- and C-termini did not lead to an appreciable difference in Cu binding affinities. The CZB-7 peptide (FIG. 1A, right) had low affinity with Ka= (7.78±1.25)×103 M−1. The consensus sequence Cu02 (FIG. 1B) exhibited a mid-range affinity with Ka=(9.89±2.18)× 105 M−1. The designer peptides (FIG. 1C, left and right) showed comparable affinities to the HypB motifs with HHTC Ka=(1.89±0.3)×106 M−1 (left) and CHSK Ka= (1.28±0.3)×106 M−1. FIG. 1D: Cu was first titrated into HHTC and an isotherm was calculated based on changes in enthalpy. Ni was then titrated into the HHTC-Cu complex and this resulted in no isotherm calculated for Ni indicating that Cu was not displaced from the peptide. Analogous experiments performed (data not shown) with for CHSK solution containing Zn with added Cu where Zn was first titrated into CHSK revealed no changes in enthalpy. Cu was then titrated into the sample cell containing CHSK+Zn and this resulted in an isotherm for Cu (data not shown). FIG. 1E: Raw data and isotherm showing binding affinity of HHTC for Cu in the absence (left) and presence (right) of the competing ion, Zn or Ni.

FIG. 4B is a graph of Cu (µM) remaining in solution for n=3 samples after incubation with mycelium treated or not treated with CBD-2×HHTC-Re for 30 minutes and FIG. 4C is a similar graph after 72 hours. The Cu concentration in the initial copper solution was 325 (+/−25) µM Cu. Control reactions contained Cu solution only. All experiments were conducted in triplicate. The amount of Cu adsorbed was calculated by taking the difference between the initial Cu in system and the remaining Cu after incubation with treated or untreated mycelium. Cu is below detection limits for the treated filters after 30 minutes and 72 hours. After 30 minutes of tangential flow, the untreated mycelium adsorbed about 23% of the copper in solution, while the treated mycelium (filter prototype) was able to sequester ~92% of the available Cu in solution.

DETAILED DESCRIPTION OF THE INVENTION

Figure 1A:
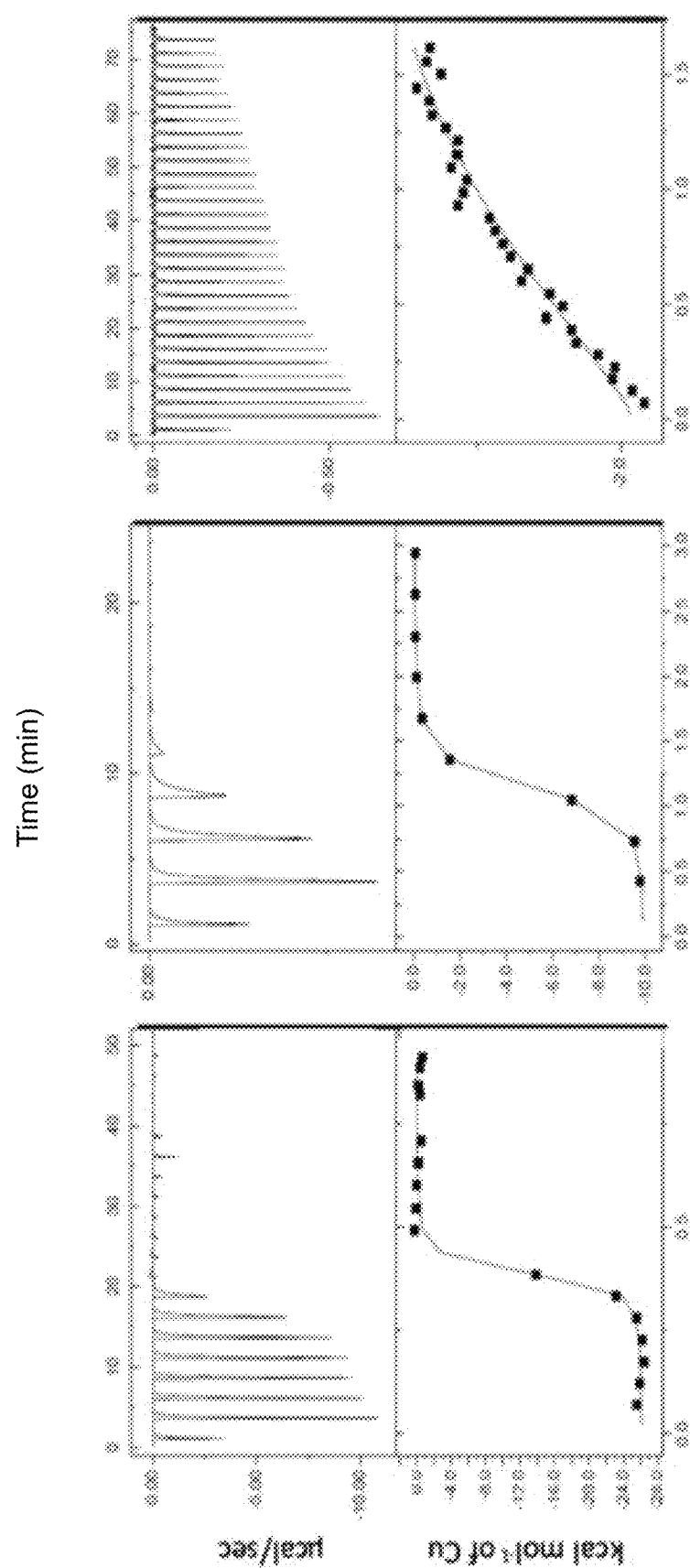
FIGS. 1A-1E. Graphs of raw data (µcal/sec vs. time (minutes)) and isotherms (kcalmol-1 of Cu vs. Molar ratio).

The invention relates to method of capturing a target chemical species from solution using a naturally-occurring or bioengineered peptide configured to selectively bind to the target chemical species. The naturally-occurring or bioengineered peptide is called a target-binding domain. The target chemical species binds to the target-binding domain and is removed from solution. The target-binding domain is chemically bonded to a selected solid substrate. Chemical bonding of the target-binding domain to the substrate results in functionalization or derivatization of the substrate. Chemical bonding of the target-binding domain to the substrate does not interfere with binding of the target to the target-binding domain. Binding of the target to the target-binding domain which in turn is bound to the substrate results in capture of the target by the substrate which allows isolation of the target from solution and other solutes in the solution and removal of the target substance from solution. Substrates which are functionalized to carry one or more target-binding domains can be used to purify the solution or to capture and collect target chemical species from solution. Functionalized substrates of the invention have a variety of purification, filtering, and collection applications and can be used to facilitate detection, identification and quantitation of target chemical species in solution. In general, substrates and the means used to functionalize the substrate to carry the target-binding domain are selected to be compatible with a given application, target, solution and the operating conditions (temperature, pH, solvent, etc.) under which the method is to be applied. In some embodiments, the target-binding domain binds to a metal. In some embodiments, the metal-binding domain is one that is selective for binding a given metal or groups of metals. The terms functionalized (functionalization) and derivatized (derivatization) are used interchangeably herein. Any method for functionalization or derivatization of a solid substrate with a fusion peptide or protein can be employed to make functionalized or derivatized substrates herein.

Target-binding is selective when the target-binding domain exhibits a higher binding affinity for one target species than for a structurally or chemically related target species. For example, metal binding is selective when the metal-binding domain exhibits a higher binding affinity for one metal or groups of metals compared to another metal or another group of metals. For example, a metal-binding domain may have a higher affinity for binding to a metal of a given group of metal, e.g., the lanthanide metals, than it has for a different group of metals, e.g., transition metals. For example, a metal-binding domain may have a higher affinity for binding to a particular metal, e.g., copper, than it has for different but related metals, e.g., nickel, zinc or other transition metals. Selective target binding can be useful for the separation of targets from different chemically or structurally related targets in solution. For example, selective metal binding can be useful for separating one desired metal from other undesired metals dissolved or suspended in solution. Preferably, a target-binding domain exhibits selective target binding when the binding affinity for the desired target is at least 1.5 fold higher than the binding affinity for the undesired metals. Selectivity depends on a given application and what it is desired to bind, isolate or collect and what the desired target is to be separated from. A metal-binding domain is selective for a given desired metal when its binding affinity to that desired metal is higher than its binding affinity to other metals from which the desired metal is to be separated. In some embodiments, the binding affinity to the desired metal is at least 2-fold higher than the binding affinity to other metals form which the desired metal is to be separated. In some embodiments, the differential target or metal binding affinity for desired target or metal is at least 5-fold or at least 10-fold higher than target or metal binding affinity for undesired targets or metals. Selectivity for target binding will depend upon conditions in which target binding occurs, such as temperature, solvent or solvent mixture, pH and the relative concentrations of desired and undesired target species in solution. For many applications, target-binding selectivity is not critical. Target-binding selectivity is useful or important in applications where separation of related target species is needed.

The examples herein demonstrate that modification of the amino acid sequence of metal-binding domains can provide enhanced selectivity for binding of a selected metal, such as copper. In some embodiments, metal-binding domains herein have been modified to enhance binding affinity to copper, particularly with respect to zinc and nickel.

Any means known in the art can be employed to functionalize or derivatize a selected substrate with the target-binding domain (a peptide). Chemical means are known in the art for covalently attaching peptides to various surfaces, include glass, quartz, resin, plastics, organic polymers, biological polymers, cellulose, chitin, xylan and the like. One of ordinary skill in the art can select suitable chemical means for functionalization of a selected substrate with a given peptide that results in retention of the target-binding function of the peptide. In some embodiments, a selected peptide can be synthesized and thereafter chemically bonded to the substrate, typically a surface of the substrate. In some embodiments, a selected peptide can be synthesized by stepwise addition of amino acids to a growing peptide bonded to a surface by known methods of solid phase peptide synthesis. In some embodiments, a selected peptide or protein can be synthesized by expression of a nucleic acid encoding the peptide or protein and thereafter bound to a substrate. In some embodiments, a fusion peptide or protein comprises a target-binding domain and a substrate-binding domain where the substrate-binding domain allows for binding to the substrate. In some embodiments, a fusion peptide or protein comprises a target-binding domain and a substrate-binding domain and both the target-binding domain and the substrate-binding domain retain their binding functions. In some embodiments, a fusion peptide or protein comprises a selective target-binding domain and a substrate-binding domain and the target-binding domain retained its selective binding and the substrate-binding domain retained its binding functions.

In embodiments, the invention provided fusion peptides and proteins for applications to methods described herein. There term peptide as used herein refers to relatively short chains of amino acids between 2 and 50 amino acids linked by peptide bonds. Shorter peptides are designated oligopeptides, herein up to 10 amino acids. Longer peptides from 10 to 50 amino acids in length are designated polypeptides. The term protein is used herein for polypeptides having greater than 50 amino acids linked by peptide bonds. Fusion peptides and proteins herein can have N-terminal amine groups and C-terminal carboxy groups and may in the form of salts or may be zwitterionic. Fusion peptides and proteins herein can be derivatized at their N-terminus or at their C-terminus or both as is known in the art. In some embodiments, peptides and proteins herein are derivatives at their N-terminus and C-terminus to generate a non-charged species. For example, the N-terminal of the fusion peptide or protein can be derivatized as is known in the art with an acyl group (particularly an alkylacyl group and more particularly and acetyl group), a urea group a carbamate group or an alkyl amine group. For example, the C-terminus of the fusion peptide or protein can be derivatized as is known in the art with an amide (particularly an alkyl amide), an ester (particularly an alkyl ester), or an aldehyde. Fusion peptides and proteins herein are optionally derivatized with a label or reported group. The label or reporter is a chemical or biochemical group that is detectable by some means, such a fluorescent label.

A fusion peptide or protein herein is formed by combining amino acid sequences from heterologous sources. For example, a fusion peptide or protein can contain a first amino acid sequence derived originally from an organism of one genus or species with a second amino acid sequence that is synthetic sequence, is sequence derived from an organism of a different genus or species as the first sequence, or is sequence derived from an organism of the same genus or species as the first sequence, but which is not from the same protein origin as the first sequence. For example, in a fusion peptide or protein containing heterologous sequences, a target-binding sequence can be derived from a first protein of an organism and a substrate-binding sequence can be derived from a different protein of the same organism. In some embodiment, the target-binding sequence or the substrate-binding sequence are artificial or synthetic sequences in which the sequence derived from an organism is modified in amino acid sequence, for example as described herein. Amino acid sequence modifications include replacement of one or more amino acids in the original sequence derived from the organism. Amino acid sequence modifications can also include deletions or replacements of amino acids from a known sequence, such as a known target-binding sequence or a known substrate-binding sequence. In some embodiments, target-binding and/or substrate binding sequences herein can be modified as is known in the art by conservative amino acid replacements. A conservative amino acid replacement in a peptide or protein is replacement of an amino acid in the peptide or protein with a different amino acid having similar biochemical properties to the amino acid that is replaced. Biochemical properties include, among others, charge, hydrophobicity and size.

Conservative replacements, include:
Replacement of an aliphatic amino acid for another aliphatic amino acid, where aliphatic amino acids are glycine, alanine, valine, leucine and isoleucine;
Replacement of a hydroxyl or sulfur/selenium-containing amino acid for another a hydroxyl or sulfur/selenium-containing amino acid, where hydroxyl or sulfur/selenium-containing amino acid are serine, cysteine, selenocysteine, threonine and methionine;
Replacement of an aromatic amino acid for another aromatic amino acid, where aromatic amino acids are phenylalanine, tyrosine and tryptophan;
Replacement of a basic amino acid for another basic amino acid, where basic amino acids are histidine, lysine and arginine; and/or
Replacement of an acidic amino acid for another acidic amino acid, where acidic amino acids are aspartate, glutamate, asparagine and glutamine.

In some embodiments, substrate-bind sequences herein can be modified as is known in the art by conservative amino acid replacements. In some embodiments, a substrate-bind sequence herein can be modified as is known in the art by conservative amino acid replacements and the modified substrate-binding sequence retains 85% or more sequence identity with the non-modified substrate-binding sequence. In some embodiments, a substrate-binding sequence that is modified by conservative amino acid sequence replacements retains 90% or more, 95% or more, 97% or more, 98% or more, or 99% or more sequence identity with the non-modified substrate-binding sequence.

In some embodiments, chitin-bind sequences herein can be modified as is known in the art by conservative amino acid replacements. In some embodiments, a chitin-bind sequence herein can be modified as is known in the art by conservative amino acid replacements and the modified chitin-binding sequence retains 85% or more sequence identity with the non-modified chitin-binding sequence. In some embodiments, a chitin-binding sequence that is modified by conservative amino acid sequence replacements retains 90% or more, 95% or more, 97% or more, 98% or more, or 99% or more sequence identity with the non-modified chitin-binding sequence.

In some embodiments, metal-binding sequences herein can be modified as is known in the art by conservative amino acid replacements. In some embodiments, a metal-bind sequence herein can be modified as is known in the art by conservative amino acid replacements and the modified metal-binding sequence retains 85% or more sequence identity with the non-modified metal-binding sequence. In some embodiments, a metal-binding sequence that is modified by conservative amino acid sequence replacements retains 90% or more, 95% or more, 97% or more, 98% or more, or 99% or more sequence identity with the non-modified metal-binding sequence.

In some embodiments, copper-binding sequences herein can be modified as is known in the art by conservative amino acid replacements. In some embodiments, a copper-bind sequence herein can be modified as is known in the art by conservative amino acid replacements and the modified copper-binding sequence retains 85% or more sequence identity with the non-modified copper-binding sequence. In some embodiments, a copper-binding sequence that is modified by conservative amino acid sequence replacements retains 90% or more, 95% or more, 97% or more, 98% or more, or 99% or more sequence identity with the non-modified copper-binding sequence.

In some embodiments, metal-binding sequences herein can be modified by deletion of one or more lysine, aspartate, glutamate, threonine, serine or tyrosine from the metal-binding sequence. In some embodiments, metal-binding sequences herein can be modified by replacement of one or more lysine, aspartate, glutamate, threonine, serine or tyrosine with one or more asparagine, leucine, glycine, glutamate or valine. In some embodiments, the metal-bind sequence that is so modified retains 85% or more sequence identity with the non-modified metal-binding sequence. In some embodiments, the so modified metal-binding sequence retains 90% or more, 95% or more, 97% or more, 98% or more, or 99% or more sequence identity with the non-modified metal-binding sequence.

In some embodiments, copper-binding sequences herein can be modified by deletion of one or more lysine, aspartate, glutamate, threonine, serine or tyrosine from the copper-binding sequence. In some embodiments, copper-binding sequences herein can be modified by replacement of one or more lysine, aspartate, glutamate, threonine, serine or tyrosine with one or more asparagine, leucine, glycine, glutamate or valine. In some embodiments, the copper-bind sequence that is so modified retains 85% or more sequence identity with the non-modified copper-binding sequence. In some embodiments, the so modified copper-binding sequence retains 90% or more, 95% or more, 97% or more, 98% or more, or 99% or more sequence identity with the non-modified copper-binding sequence.

In some embodiments, the fusion peptides herein are 20-50 amino acids in length. In some embodiments, the fusion peptides herein are 30-50 amino acids in length. In some embodiments, the fusion peptides herein are 40-50 amino acids in length. In some embodiments, the fusion peptides herein are 20-50 amino acids in length. In some embodiments, the fusion peptides herein are 30-50 amino acids in length. In some embodiments, the fusion peptides herein are 40-50 amino acids in length.

The substrate and its bond to the target chemical species are preferably inert with respect to the solvent and solution in which the target is dissolved or suspended.

In some embodiments, the invention provides a method of functionalizing biological substrates with naturally-occurring or bioengineered peptides to bind targeted chemical species. Binding of target substance to the peptide which in turn is bound to the substrate functions to capture the target substance. In some embodiments, the invention provides a method of functionalizing biological substrates with naturally-occurring or bioengineered peptides to bind chemical species, including molecules or metals, for utilization in water filtration applications. In some embodiments, the invention provides a method of functionalizing biological substrates with naturally-occurring or bioengineered peptides to bind targeted chemical species, including molecules or metals, for recovery of targeted chemical species from solution, particularly aqueous solution. In some embodiments, the methods herein can be utilized for the removal or filtering of targeted chemical species from solution, particularly aqueous solution. In some embodiments, the methods herein can be utilized to reduce the amount of targeted chemical species in solution, particularly aqueous solution. In some embodiments, the methods herein can be utilized to remove the targeted chemical species from solution, particularly aqueous solution, to an undetectable level. In some embodiments, the methods herein can be utilized for the detection and/or identification of targeted molecules in solution, particularly aqueous solution. In some embodiments, after target chemical species is captured on the substrate, the substrate is separated from contact with solution and the target is released from the substrate for collection. In some embodiments, the target chemical species contains a metal. In some embodiments, the target chemical species is a metal complex. In some embodiments, the target chemical species is a metal oxide or hydroxide. In some embodiments, the target chemical species comprises a metal ion.

Any chemical species can be a target chemical species and in general any chemical species for which a target-binding domain has been identified in the art. Target species include among others various metabolites (e.g., mono- or disaccharides), steroids, organic dyes, small molecule drugs, non-metal toxins, other peptides, nucleosides, nucleic acids. In embodiments, employing a target-binding domain in combination with a substrate-binding domain in a fusion peptide or protein, the target and the substrate are distinct and the target-binding domain does not bind to the substrate and the substrate-binding domain does not bind to the target.

The target can, for example, be a metal ion, metal complex, metal ion, neutral (uncharged) molecule or a charged molecule (anion or cation) dissolved in solution. The target can be a metal species, which includes metal ions (which may have different valences/charge states), or metal complexes. Target metal species include those that comprise metals classified into different groups, such as the alkali metals, the alkaline-earth metals, transition metals, lanthanide metals (metals with atomic numbers 57-71 from lanthanum to lutetium) or rare earth metals (the lanthanide metals and scandium and yttrium), the actinides, precious metals (e.g., gold, silver, platinum), or the platinum group metals (ruthenium, rhodium, palladium, osmium, iridium and platinum). Exemplary metal-binding domains are provided in Tables 3 and 4. Many additional metal-binding domains are known in the art or can be identified by methods that are well-known in the art such as biopanning techniques, and particularly those techniques which employ phage, bacterial surface or related displayed combinatorial peptide libraries or related peptide libraries.

His-tags (polyhistidine-tags) are known in the art and are often used in the preparation of fusion peptides and proteins to facilitate peptide or protein purification by binding of the His-tag to a Ni2+-affinity column. His-tags bind to copper, nickel, zinc and cobalt (where affinity to the metal decreases in the listed order). While in general, His-tags can be employed as metal-binding domains in the methods and materials of this invention, the use of metal-binding domains other than His-tags is preferred. In some embodiments, the metal-binding domain of fusion peptides and fusion proteins of this invention is a metal-binding domain other than a His-tag.

In some embodiments, the invention employs one or more of the metal-binding domains having an amino acid sequence of SEQ ID NOs: 11-20, some of which include tandem repeats of metal-binding domains with optional flexible linkers separating the domains. In some embodiments, the invention employs one or more of the metal-binding domains having an amino acid sequence of SEQ ID NOs: 11-20 or an amino acid sequence having 85% or higher sequence identity therewith and which retain metal-binding. In some embodiments, the invention employs one or more of the metal-binding domains having an amino acid sequence of SEQ ID NOs: 11-20 or an amino acid sequence wherein the N-terminal or the C-terminal amino acid are deleted and which retain metal-binding. In some embodiments, the invention employs one or more of the metal-binding domains having one or more repeats of a metal-binding domain having amino acid sequence of SEQ ID NOs: 1-10, or an amino acid sequence having 85% or higher sequence identity therewith, wherein the repeats of the metal-binding sequence are separated by a flexible linker peptide sequence. In some embodiments, the forgoing metal-binding domains are bonded to a selected solid substrate by any chemical or biologically-based method (e.g., use of a substrate-binding domain) know in the art for bonding peptides to a substrate. In some embodiments, the forgoing metal-binding domains are bonded to a selected solid substrate without the use of a substrate-binding domain. In some embodiments, where the forgoing metal-binding domains are bonded to a substrate, a fusion peptide or protein containing a substrate-binding domain is sued to functionalize the substrate with the metal-binding domain. In some embodiments, the forgoing metal-binding domains are bonded to any solid substrate, including among others, a polysaccharide, lignocellulose, cellulose, hemicellulose, xylan, chitin, lignin, glass, quartz, paper, polymers, cloth, cotton fiber, plastic, or resin. In some embodiments, the forgoing metal-binding domains are bonded to plant materials, such as wood shavings, sawdust, bagasse, corn stover and the like. In some embodiments, the forgoing metal-binding domains bonded to substrate are employed in the methods herein to capture or isolate metals from solution.

Figure 6:
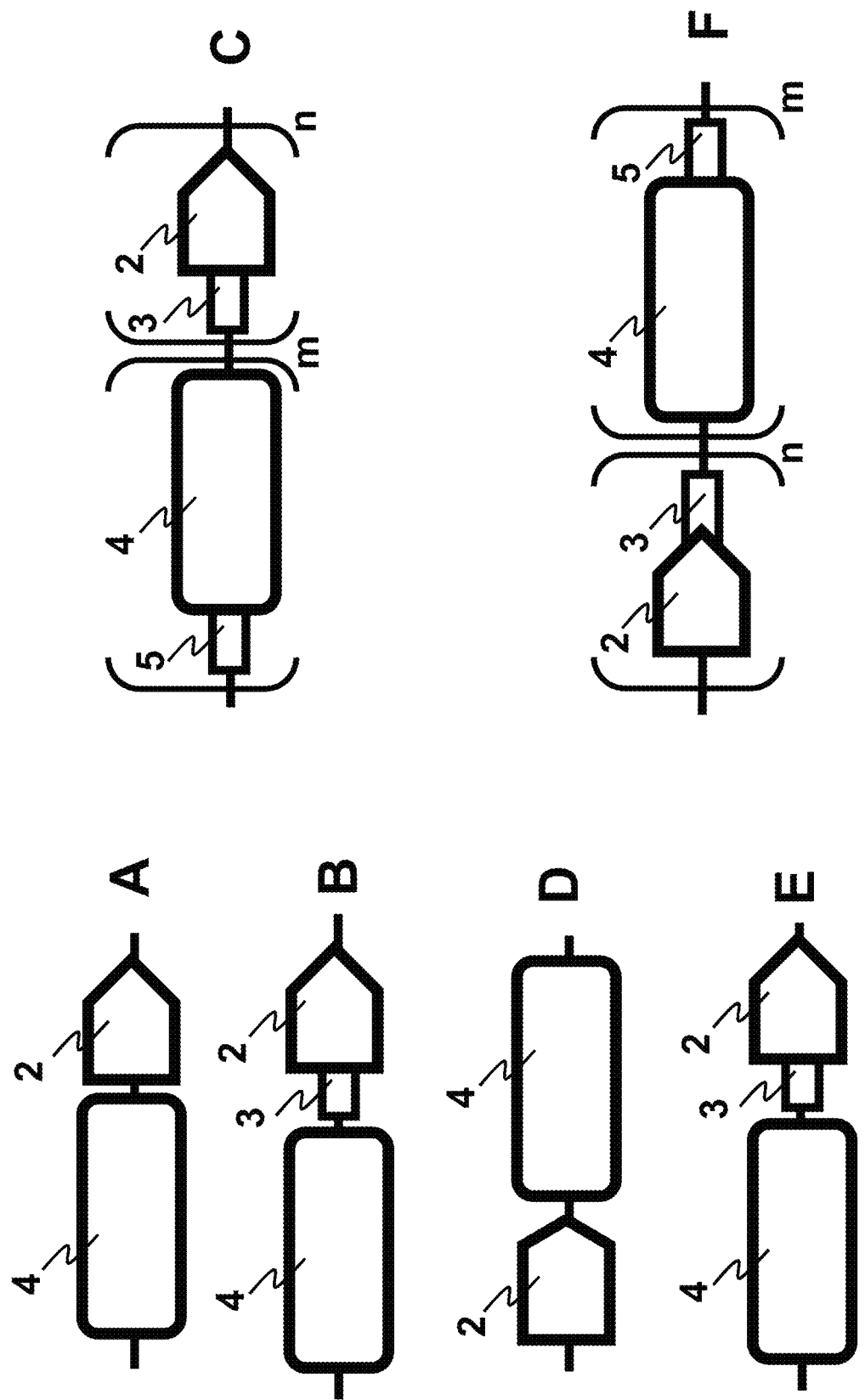
FIG. 6: Schematic illustration of construction of fusion proteins comprising one or more repeats of flexible amino acid linker-metal-binding peptide (e.g., Flex-HHTC-Re, SEQ ID NO: 15), chitin-binding domain (ChBD, e.g., SEQ ID NO: 44). Construction, expression and purification of fusion proteins is described in the Examples herein. Nucleic acid encoding the fusion protein is inserted between the RBS (Ribosome-binding site) and the T7 terminator into the schematically illustrated expression vector for expression by the T7 promoter. The illustrated vector contains a His-tag (×6), a Lumio Tag and Intein which are employed for expression and purification, but which are cleaved from the final fusion protein product. The amino acid sequences of exemplary fusion proteins expressed and purified using the illustrated system are provided in Table 7.
Figure 7:
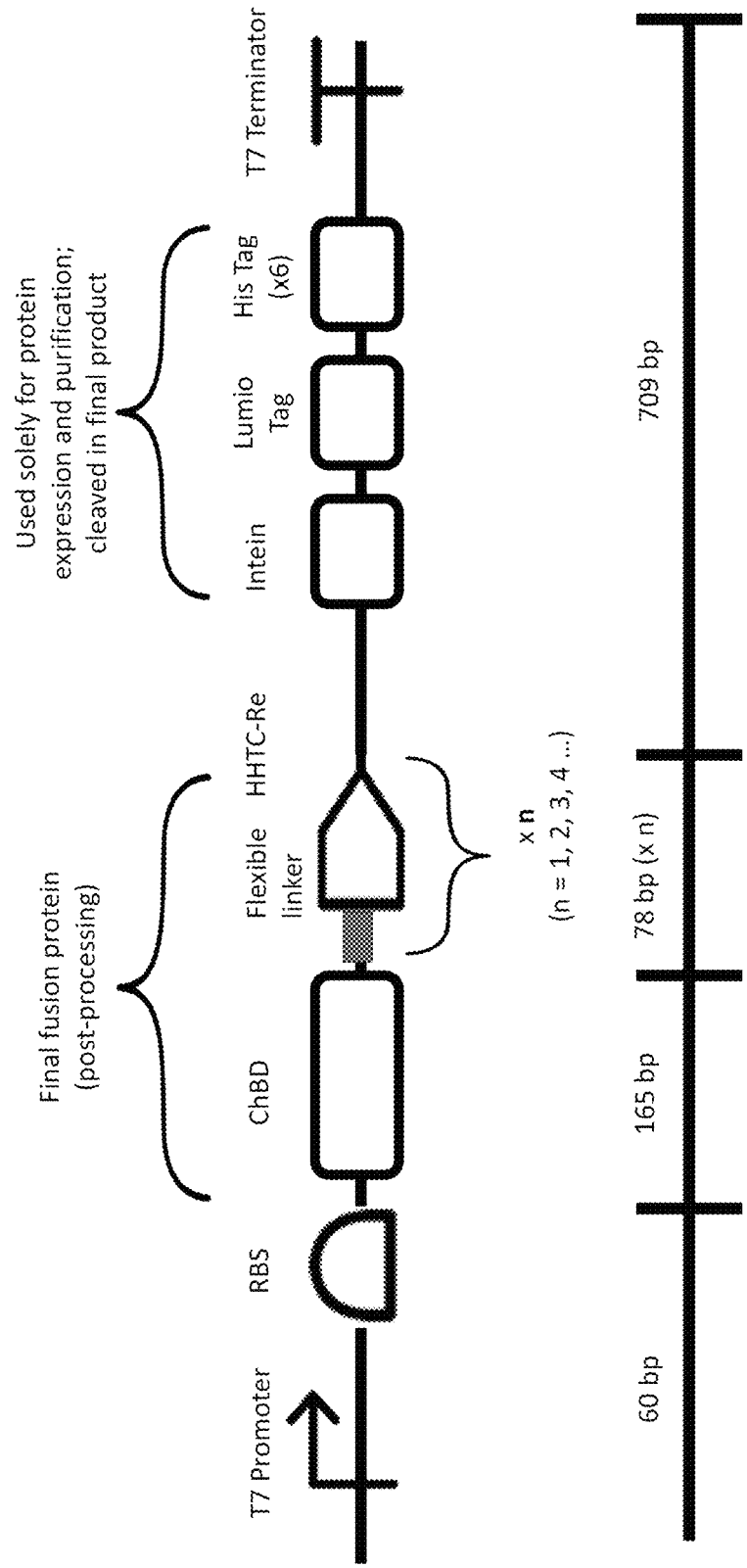
FIG. 7: Schematic illustrations of exemplary fusion peptides and proteins of the invention where the peptides and proteins are shown as convention from the N-terminus to the C-terminus. View A illustrates a fusion with a single metal-binding domain (2) and a single substrate-binding domain (4), where the target-binding domain is positioned downstream (i.e., towards the C-terminus) from the substrate-binding domain. View B illustrates a fusion with a single metal-binding domain (2) and a single substrate-binding domain (4), and a single flexible linker 3 between these domains and where the target-binding domain is positioned downstream (i.e., towards the C-terminus) from the substrate-binding domain. View C illustrates an exemplary fusion with multiple metal-binding domains (2), where n is 2-6, for example, and multiple substrate-binding domains (4), wherein m is 2-6, for example, and preferably is 2, and one or more flexible linkers 3 or 5 (which can be the same or different) between these domains and where the target-binding domain is positioned downstream (i.e., towards the C-terminus) from the substrate-binding domain. View C also encompasses structures where there is no flexible linker 5 preceding a first iteration of the substrate-binding domain. View D illustrates a fusion with a single metal-binding domain (2) and a single substrate-binding domain (4), where the target-binding domain is positioned upstream (i.e., towards the N-terminus) from the substrate-binding domain. View E illustrates a fusion with a single metal-binding domain (2) and a single substrate-binding domain (4), and a single flexible linker 3 between these domains and where the target-binding domain is positioned upstream (i.e., towards the N-terminus) from the substrate-binding domain. View F illustrates an exemplary fusion with multiple metal-binding domains (2), where n is 2-6, for example, and multiple substrate-binding domains (4), wherein m is 2-6, for example, and preferably is 2, and one or more flexible linkers 3 or 5 (which can be the same or different) between these domains and where the target-binding domains are positioned upstream (i.e., towards the N-terminus) from the substrate-binding domain. View F also encompasses structures where there is no flexible linker 5 following the last iteration of the substrate-binding domain.

Additional exemplary metal-binding domains are listed in Table 4 herein. This listing provides the amino acid sequence of the domain and the metal or group of metals to which the domain binds. It is noted that in some cases, the indicated metal-binding domain may bind to metals other than the metal indicated. One of ordinary skill in the art will recognize that a large number of metal-binding domains have been identified and can be employed in the methods of this invention. In particular, any of the metal-binding domains listed in Table 4 can be introduced into a fusion peptide or protein containing a chitin-binding domain as described herein. More specifically, any of the metal-binding domains listed in Table 4 can be introduced into a fusion peptide or protein comprising a chitin-binding domain herein in a 2×-6× repeat optionally separated by a flexible peptide linker as illustrated in FIG. 6 and FIG. 7. In some embodiments, any one of the metal-binding domains of the amino acid sequences of SEQ ID NOs: 21-43 or an amino acid sequence having 85% or higher sequence identity thereto can be employed in fusion peptides and proteins of this invention which also include a chitin-binding domain.

Target chemical species are isolated or collected from a solution in which the target species are dissolved or suspended. In some embodiments, a targeted metal species is isolated or collected from a solution in which the targeted metal species is dissolved or suspended. In some embodiments, the solution is an aqueous solution comprising the targeted chemical species. which may contain the targeted chemical species. In some embodiments, the aqueous solution is a miscible mixture of water and an organic solvent, such as alcohols (methanol, ethanol, propanol), tetrahydrofuran, dimethylformamide, dimethylsulfoxide, acetone, or acetonitrile. In some embodiments, the aqueous solution comprises up to 25% by volume of an organic solvent soluble in water. In some embodiments, the aqueous solution comprises up to 10% by volume of an organic solvent soluble in water. In some embodiments, the aqueous solution has pH ranging from 4 to 10. In some embodiments, the aqueous solution has pH ranging from 5 to 9.

The concentration of the target chemical species in the solution is not critical. It will be appreciated that high levels of target in solution may saturate a substrate which is functionalized with a target-binding domain. It will be appreciated that the amount of functionalization on a substrate, the amount of functionalized substrate employed and the manner and time of contacting the functionalized substrate with the solution may be varied to achieve a desired level of capture of the target or a desired level of reduction of target in the solution.

The functionalized substrate may have a variety of forms. It may be in the form of beads, pellets, particles, films or a mat or sheet. Any of such forms of functionalized substrate may be simply placed in contact with the solution. In some embodiments, the functionalized substrate should be readily removed from contact with the solution in order to remove target from solution. The functionalized substrate may, for example, be porous so that solution can be passed through functionalized pores in the substrate. The functionalized substrate may, for example, be coated on a surface of a vessel or conduit into which or through which the solution is flowed. The functionalized substrate may, for example, be formed into a filter for capturing target form solution. Beads or other particles of functionalized substrate may, for example, be formed into a column through which solution is flowed.

Functionalizing a biological surface with engineered peptides and/or proteins as described herein can be applied to any biological substrate that can be bound with a protein binding tag. For example, a cellulose surface can be similarly used with a peptide containing a cellulose binding domain and a metal binding peptide domain. Additionally, these include fusing the chitin-binding domain with proteins that can bind non-metal toxins, dyes, drugs or other products to be concentrated from solution. It could also include fusion proteins of the chitin-binding domain with proteins that themselves bind to antibodies.

In some embodiments, the substrate is a carbohydrate and more specifically is a polysaccharide, such as cellulose or hemicellulose. In some embodiments, the substrate comprises cellulose, hemicellulose, xylan, lignocellulose or lignin and the fusion peptide or protein comprises a carbohydrate-binding domain that binds to the substrate. In some embodiments, the substrate is a naturally-occurring material to which a carbohydrate-binding domain binds. In some embodiments, the substrate is wood chips, saw dust, cotton fiber or cloth, or paper. In some embodiments, the substrate comprises or is cellulose and the substrate-binding domain binds to cellulose. In some embodiments, the substrate comprises or is lignocellulose or lignin and the substrate-binding domain binds to lignin. In some embodiments, the substrate comprises or is xylan and the substrate-binding domain binds to xylan.

A large number of carbohydrate-binding domains (also designated carbohydrate-binding modules) have been identified and many sequenced. A carbohydrate-biding domain is a peptide domain typically found in an enzyme active towards a carbohydrate, such as cellulose, which functions for binding of the enzyme to the carbohydrate. Carbohydrate-binding domains have been characterized into a large number of families based on similarities in structure, binding specificity or origin (e, g., fungal, bacterial). For example, families CMB1-CBM49 are known. Certain families, such as CBM3 are associated with cellulose binding. Other families, such as CBM5 and CBM19 are associated with chitin-binding. Some carbohydrate-binding domains bind to more than one type of carbohydrate. Some carbohydrate-binding domains that bind to cellulose also bind to lignin. Any carbohydrate-binding domain that binds to a solid substrate can be used in the materials and methods of this invention.

In some embodiments, the substrate comprises cellulose. In some embodiments, the substrate comprises cellulose and the fusion peptide or protein comprises a cellulose-binding domain. In some embodiments, the cellulose-binding domain is one having an amino acid sequence of SEQ ID NOs:54-59 or an amino acid sequence having 85% or higher sequence identity therewith. Consensus sequences for cellulose-binding domains have been identified in the art. Consensus sequences can be identified by comparison of cellulose-binding sequences from a number of cellulose-binding domains of different origin. Consensus sequences can be identified by experimentally determining the effect of changing amino acids in the binding domain on binding affinity to the substrate. For example, U.S. Pat. No. 7,445,922 identified a consensus cellulose-binding sequences and is incorporated by reference herein at least for that consensus sequence which can be employed as a cellulose-binding domain in fusion peptides and proteins useful in this invention. U.S. Pat. Nos. 6,407,208, 7,445,922 and 8,506,717 may describe and provide sequence for cellulose-binding domains other than those specifically listed in Table 6. These patents are incorporated by reference herein at least for any cellulose-binding domains described therein.

In some embodiments, the substrate comprises chitin. In some embodiments, the substrate comprises chitin and the fusion peptide or protein comprises a chitin-binding domain. In some embodiment, the substrate comprises 1 to 100% by weight chitin. In some embodiments, the substrate comprises 5 to 100% by weight chitin. In some embodiments, the substrate comprises 5 to 25% by weight chitin. In some embodiments, the substrate comprises 25% or more by weight chitin. In some embodiments, the substrate comprises 80% or more by weight chitin. In some embodiments, the chitin-containing substrate comprises naturally-occurring materials that contain chitin. Chitin is a polymer of N-acetylglusocamine and is found in the cell walls of fungi and the exoskeletons of arthropods (e.g., crustaceans and insects). In some embodiment, the chitin-substrate comprises shrimp, lobster or crab shells, fish scales or related seafood waste. In some embodiments, the chitin containing substrate is derived from certain fungi and more particularly is derived from fungal hyphae or mycelium.

In some embodiments, the chitin-binding domain is one having an amino acid sequence of SEQ ID NOs:44-53 or an amino acid sequence having 85% or higher sequence identity therewith. Consensus sequences for chitin-binding domains have been identified in the art. Consensus sequences can be identified by comparison of cellulose-binding sequences from a number of cellulose-binding domains of different origin. Consensus sequences can be identified by experimentally determining the effect of changing amino acids in the binding domain on binding affinity to the substrate. Consensus chitin-binding domains which are known in the art can be employed in the methods and materials herein. For example, U.S. Pat. No. 7,060,465 identified a consensus chitin-binding sequence by such a comparison and is incorporated by reference herein at least for that consensus sequence information which can be employed as a cellulose-binding domain in fusion peptides and proteins useful in this invention. U.S. Pat. No. 7,060,465 also describes modified chitin-binding domains in which one or more amino acids of a naturally-occurring chitin-binding domain having been modified without substantial detriment to chitin-binding affinity and is incorporated by reference herein for such modified chitin-binding domains. U.S. Pat. Nos. 5,514,779, 7,862,826, 7,060,465, and 8,618,066 may describe and provide sequence for chitin-binding domains other than those specifically listed in Table 5. These patents are incorporated by reference herein at least for any chitin-binding domains described therein.

Fungal mycelium is the vegetative part of a fungus or a fungal colony composed of branched hyphae of the fungus. Fungal mycelium is a fibrous material that can be grown in large quantities. Methods are known for growing fungal mycelium into a selected shape or structure by growing the mycelium on a growth substrate within a mold having the selected shape or structure (Cerimi et al., 2019). This reference is incorporated by reference herein for its description of methods for use of fungal mycelium to formed shaped articles. Methods are known for forming porous mycelium material called mycelium foam. Such methods can be employed to form mycelium into a variety for shapes and structures for use as substrates in the methods of this invention. Mycelium comprises chitin and as is shown herein, chitin-binding domains bind to the chitin in mycelium to functionalize the mycelium.

In general, any fungal mycelium containing chitin can be employed as a substrate for functionalization by fusion peptides or proteins described herein which comprise a chitin-binding domain. In some embodiments, the mycelium is that of a unicellular or multicellular fungus. In some embodiments, the mycelium is that of a basidiomycete. In some embodiment, the mycelium is that of a mushroom. In some embodiments, the mycelium is that of an edible or medicinal fungus. In some embodiments, the mycelium is that of a species of the genus *Gandoderma*. In some embodiments, the mycelium is that of a species of the genus *Pleurotus*. Exemplary species of *Gandoderma*, include among others, *G. lucidum, G. tsugae, G. applanatum, G. meredithiae* and *G. resinaceum*. Exemplary species of *Pleurotus* (oyster mushroom) include among others, *P. ostreatus, P. pulmonarius, P. populinus* and *P. eryngii*. In some embodiments, the mycelium is that of *G. lucidum*. In some embodiment, the mycelium is that of *P. ostreatus*.

In some embodiments, metal sequestration is achieved using functionalized fungal mycelium by treating the mycelium surface with peptides containing metal-binding motifs, optionally in tandem repeats containing a chitin-binding domain that can bind to the solid mycelium surface.

One of the benefits of using mycelium material, as compared to flagella-based or cellulose filtration tools, is that it leverages the concept of economies of scale, and presents an entirely feasible option of scale-up of this technology to a level that could be successfully implemented on a space mission and on earth in developing countries with poor access to clean water. Fungi are capable of displaying growth on an enormous variety of biomass types, and grow at a rate that is unparalleled by other biological agents used in synthetic biology today.

Growth rate of fungi on various growth substrates can be assessed to determine which growth substrate could be used with minimal added growth medium. The use of growth substrate with minimal added growth medium decreases cost of product of mycelium. Useful growth substrates included sawdust, lawn clippings, used coffee grounds and other forms of food waste. In some embodiments, fungal mycelium can be grown on agricultural waste. In some embodiments, fungal mycelium can be grown on food waste.

Mycelium are believed to be hydrophobic. It was found that functionalization with peptides as described herein turned an otherwise hydrophobic surface into a more hydrophilic functionalized adsorptive surface that can interact with dissolved ions in aqueous solutions.

FIG. 6 schematically illustrates the preparation of nucleic acid constructs encoding fusion peptides and proteins of this invention. It will be appreciated by one of ordinary skill in the art that a number of methods for constructions of such constructs and the expression of fusion peptide and proteins are known in the art. All such known methods can be employed for the preparation of fusion peptides and proteins of this invention. Methods are exemplified herein in the preparation of fusion peptides and proteins comprising certain metal-binding domains and a chitin-binding domain. The methods exemplified herein can be readily adapted to the preparation of fusion peptides and proteins comprising any target-binding domain and any substrate-binding domain. In some embodiments, the methods described herein can be employed to prepare fusion peptides and proteins comprising any metal-binding domain and any known substrate-binding domain. In some embodiments, the methods described herein can be employed to prepare fusion peptides and proteins comprising any metal-binding domain and any known carbohydrate-binding domain. In some embodiments, the methods described herein can be employed to prepare fusion peptides and proteins comprising any metal-binding domain and any known cellulose binding domain. In some embodiments, the methods described herein can be employed to prepare fusion peptides and proteins comprising any metal-binding domain and any known chitin-binding domain. In some embodiments, the methods described herein can be employed to prepare fusion peptides and proteins comprising any metal-binding domain and any known xylan-binding domain. In some embodiments, the methods described herein can be employed to prepare fusion peptides and proteins comprising any metal-binding domain and any known lignin-binding domain.

The amino acid sequences of exemplary chitin-binding domains are provided in Table 5 herein. The amino acid sequences of exemplary cellulose-binding domains are provided in Table 6 herein. The amino acid sequences of exemplary xylan-binding domains are provided in Table 6 herein. The amino acid sequences of exemplary lignin-binding domains are provided in Table 6 herein.

FIG. 7 illustrates exemplary fusion peptides and proteins of this invention comprising target-binding domains and substrate-binding domains. The constructs of FIG. 7 illustrate the use of a single iteration or of tandem repeats of a metal-binding domain where repeats of the metal-binding domain are optionally separated by a flexible linker amino acid sequence. The number of repeats of the metal-binding domain is exemplified as 2-6. The constructs of FIG. 7 illustrate the use of a single iteration or of tandem repeats of a substrate-binding domain where repeats of the substrate-binding domain are optionally separated by a flexible linker amino acid sequence. The number of repeats of the metal-binding domain is exemplified as 2-6. In preferred embodiments, a single iteration of the substrate-binding domain is used or a tandem repeat of the substrate-domain where sequence repeats are optionally separated by a flexible amino acid linker are used. The constructs of FIG. 7 illustrate that the relative position of the metal-binding domain and the substrate-binding domain in the fusion are not critical. The metal-binding domain or repeats thereof can be either upstream (toward the HN-terminus) or downstream (towards the COOH terminus) of the substrate-binding domain or repeats thereof.

Fusion peptides or proteins useful for capture of metals can include any of the metal-binding domains of the amino acid sequences of SEQ ID NO: 1 to SEQ ID NO: 43 or an amino acid sequence having 85% or higher sequence identity thereto. With respect to the metal-binding domains of the amino acid sequences of SEQ ID NO: 21-43 or an amino acid sequence having 85% or higher sequence identity thereto, these sequences can be included in useful fusion peptides or proteins in single iterations or as tandem repeats as illustrated in FIG. 7.

Fusion peptides or proteins useful for capture of metals can include any of the metal-binding domains described herein, including those of Tables 3 and 4, in combination with a substrate-binding domain that is a carbohydrate-binding domain or tandem repeats thereof. Fusion peptides or proteins useful for capture of metals can include any of the metal-binding domains described herein, including those of Tables 3 and 4, in combination with a substrate-binding domain that is selected from a cellulose-binding domain, a chitin-binding domain, a xylan-binding domain or a lignin-binding domain or tandem repeats thereof. In some embodiments, fusion peptides and proteins have a single iteration of the carbohydrate-binding domain, cellulose-binding domain, chitin-binding domain, xylan-binding domain or lignin-binding domain. In some embodiments, fusion peptides and proteins have a tandem repeat of the carbohydrate-binding domain, cellulose-binding domain, chitin-binding domain, xylan-binding domain or lignin-binding domain where sequence repeats are optionally separated by a flexible linker amino acid. In some embodiments, fusion peptides and proteins have 2 to 6 repeats of a lignin-binding domain where repeats are optionally separated by a flexible amino acid linker. In some embodiments, the substrate-binding domain is a substrate-binding domain listed in Table 5 or Table 6.

Fusion peptides or proteins useful for capture of metals can include any of the metal-binding domains described herein, including those of Tables 3 and 4, in combination with a substrate-binding domain having an amino acid sequence of any one of SEQ ID NOs: 44-64 or an amino acid sequence having 85% or higher sequence identify therewith. In some embodiments, fusion peptides and proteins have a single iteration of the amino acid sequence of SEQ ID NOs: 44-64 or an amino acid sequence having 85% or higher sequence identity therewith. In some embodiments, fusion peptides and proteins have a tandem repeat of the amino acid sequence of SEQ ID NOs: 44-64 or an amino acid sequence having 85% or higher sequence identity therewith wherein sequence repeats are optionally separated by a flexible linker amino acid.

In some embodiments, the fusion peptides and proteins herein include at least one target-binding domain sequence and at least one substrate-binding domain sequence. In some embodiments, the at least one target-binding domain sequence and the at least one substrate-binding domain sequence are spaced apart from each other by at least one flexible linker peptide. In some embodiments, the fusion peptides and proteins herein include at least one metal-binding domain sequence and at least one chitin-binding domain sequence. In some embodiments, the at least one metal-binding domain sequence and the at least one chitin-binding domain sequence are spaced apart from each other by at least one flexible linker peptide.

In some embodiments, the fusion peptides or proteins herein include more than one target-binding domain sequence, which may be the same or different. In some embodiments, the more than one target-binding domain sequences are arranged sequentially in the fusion peptide or protein and optionally, but preferably one target-binding domain is spaced apart from another target-binding domain by a flexible peptide linker. In some embodiments, the fusion peptides or proteins herein include more than one substrate-binding domain sequence, which may be the same or different. In some embodiments, the more than one substrate-binding domain sequences are arranged sequentially in the fusion peptide or protein and optionally, but preferably one substrate-binding domain is spaced apart from another target-binding domain by a flexible peptide linker.

In some embodiments, the fusion peptides or proteins herein include one or more tandem repeats of the same target-binding domain sequence. In some embodiments, the fusion peptides or proteins herein include two to six repeats of the same target-binding domain. In some embodiments, the fusion peptides or proteins herein include one or more tandem repeats of the same metal-binding domain sequence. In some embodiments, the fusion peptides or proteins herein include two to six repeats of the same metal-binding domain. Such tandem repeats of the target-binding domain amino acid sequence optionally include one or more flexible linker amino acids intervening between one or more of the repetitions of the target-binding domain sequence.

In some embodiments, the fusion peptides and proteins herein include one or more tandem repeats of the same substrate-binding domain sequence. In some embodiments, the fusion peptides or proteins herein include one or two tandem repeats of the same substrate-binding domain. In some embodiments, the fusion peptides or proteins herein include one or more tandem repeats of the same chitin-binding domain sequence. In some embodiments, the fusion peptides or proteins herein include one or two repeats of the same chitin-binding domain. Such tandem repeats of the target-binding domain amino acid sequence optionally include one or more flexible linker amino acids intervening between one or more of the repetitions of the substrate-binding domain sequence.

Flexible linkers of various sizes, typically 2-31 amino acids in length, are designed, as is known in the art, by including various numbers and combinations of serine, threonine, or glycine residues or combinations thereof. Lysine and glutamate residues can also be included to improve solubility, while alanine residues can be included to improve flexibility. Rosmalen et al., 2017; Chichili et al., 2013; and Chen et al., 2013, for example, provide description of flexible amino acids linkers useful for preparation of fusion proteins. Each of these references is incorporated by reference herein to provide detail, including sequences of exemplary flexible linkers, of the use of such flexible peptide linkers. In some embodiments, the flexible linkers used in fusion peptides and proteins herein include among others:

(GS)n, where n is 3-15,
(GGS)n, where n=2-10,
(GGSGG)n, where n=1 to 6 (when n=1, the linker has sequence of SEQ ID NO: 71),
(GGGGS)n, where n=1 to 6 (when n=1, the linker has sequence of SEQ ID NO: 72),
(GSGGSG)n, where n=1-6 (when n=1, SEQ ID NO: 73).

Fusion peptides and proteins herein are optionally modified at the N-terminus or C-terminus as is known in the art. For example, N-terminal modifications include acylation (—NCOR, where R is H, or an alkyl group). Specific acylations include formylation (—NCOH) and acetylation (—NCOCH$_3$). For example, C-terminal modifications include amination (—CONHR, where R is H or alkyl) or esterification (—COOR, where R is a group other than H, e.g., alkyl).

Various specific amino acid sequences are provided in the Tables herein for metal-binding domains and substrate-binding domains. These amino acid sequences can be used in the methods herein as described herein. These amino acid sequences can be used in the preparation of fusion peptides and proteins herein as described herein. As is recognized in the art, some sequence variation can be accommodated without loss of biological function. With respect to target-binding and substrate-binding sequences herein, some sequence variation can be accommodated without loss of biological function. Sequence variation may affect binding affinity or selectivity of binding. In general, for metal-binding domains and substrate-binding domains specifically listed in Tables herein, sequences with 85% or higher sequence identity to the sequences provided will retain binding function. The listed sequences or amino acid sequences having 85% or higher, 90% or higher, 95% or higher, 96% or higher, 97% or higher, 98% or higher, or 99% or higher sequence identity are useful in the methods herein and in the fusion peptides and proteins herein. In some embodiments, the sequences in the Tables herein and amino acid sequences having 85% or higher, 90% or higher, 95% or higher, 96% or higher, 97% or higher, 98% or higher, or 99% or higher sequence identity thereto are useful in the methods and materials of this invention. In some embodiments, the sequences in the Tables herein and amino acid sequences having 85% or higher, 90% or higher, 95% or higher, 96% or higher, 97% or higher, 98% or higher, or 99% or higher sequence identity thereto and which retain at least 10% binding affinity to the target or substrate of the base binding domain are useful in the methods and materials of this invention. In some embodiments, the sequences in the Tables herein and amino acid sequences having 85% or higher, 90% or higher, 95% or higher, 96% or higher, 97% or higher, 98% or higher, or 99% or higher sequence identity thereto and which retain at least 50% binding affinity to the target or substrate of the base binding domain are useful in the methods and materials of this invention.

Sequence identity refers to the level of amino acid sequence identity between a given reference amino acids sequence, such as specifically described in Tables herein and another second amino acid sequence, such as those that are in public databases of amino acid sequences or that are described in the literature. In determining sequence identity, sequences are optimally aligned using a sequence alignment program. If, in the optimal alignment, a position in the reference sequence is occupied by the same amino acid residue as the corresponding position in the second sequence, the sequences exhibit identity with respect to that position. The level of identity between two sequences is expressed as a percent sequence identity. Exemplary computer programs which can be used to determine identity between two sequences include, but are not limited to, the BLAST programs, e.g., BLASTP, BLASTX, TBLASTX, BLASTN and TBLASTN, publicly available through NCBI (National Center for Biotechnology Information).

Comparisons of amino acid sequences are typically carried out using the BLASTP program when evaluating a given amino acid sequence relative to sequences in the GenBank protein and other public databases or other literature sources. In embodiments, BLASTP is run using default parameters of an open gap penalty of 11.0, and an extended gap penalty of 1.0, and utilize a BLOSU matrix. In some embodiments, the alignment of selected sequences in order to determine "% identity" between two or more sequences, is performed using for example, the CLUSTAL-W program. In some embodiments, the alignment program is operated with default parameters, including an open gap penalty of 10.0, an extended gap penalty of 0.1, and a BLOSUM 30 similarity matrix. In some embodiments, sequence identity is determined without allowance for sequence gaps between amino acids in the sequence. In some embodiments, sequence identity is determined allowing gaps of 1-5 amino acids in the sequence. In some embodiments, sequence identity is determined allowing differences in length of the sequences compared, where missing amino acids at the ends of the sequence being compared are counted as mismatched. Percent sequence identify can also be assessed for nucleic acid sequences as is known in the art.

In some embodiments, the invention provides nucleic acids, particularly DNA molecules having nucleic acid sequences which encode a fusion peptide or protein of this invention. For a given amino acid sequence one of ordinary skill in the art, in view of what is known in the art, can routinely determine many nucleic acid sequences that encode that amino acid sequence. One or ordinary skill in the art can routinely select from the many nucleic acids encoding a given amino acid sequence those nucleic acids that will function for expression of the amino acids in one of the many expression systems now available in the art. The examples herein describe exemplary methods used to generate a nucleic acid encoding a selected amino acid sequence, insert the nucleic acid in a vector, express the coding sequence and purify expression products to produce the desired amino acid sequence. One of ordinary skill in the art recognizes that a variety of methods are available in the art for generating nucleic acids encoding a given amino acid sequence and expressing that nucleic acid to generate the peptide or protein having that amino acid sequence.

All references throughout this application, for example patent documents including issued or granted patents or equivalents, patent application publications, and non-patent literature documents or other source material, are each incorporated by reference herein in its entirety, as though individually incorporated by reference. The non-patent and patent references cited herein are incorporated by reference herein at least for the subject matter for which they were cited herein. References cited herein are also incorporated by reference herein in their entirety to indicate the state of the art, in some cases as of their filing date, and it is intended that this information can be employed herein, if needed, to exclude (for example, to disclaim) specific embodiments that are in the prior art. More specifically, the references cited herein are incorporated by reference herein for descriptions of target-binding domains and substrate-binding domains, particularly those that are not specifically listed in Tables herein.

Urbina et al., 2019 provides details of the experiments described herein and is incorporated by reference herein in its entirety.

When a group or range is disclosed herein, it is understood that each individual member of that group or range and all subgroups and subranges of the group or range members are disclosed separately herein. When a Markush group or other grouping is used herein, all individual members of the group and all combinations and subcombinations possible of the group are intended to be individually disclosed herein.

Every combination of components described or exemplified herein can be used to practice the invention, unless otherwise stated. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles or mechanisms of action relating to the invention. It is recognized that regardless of the ultimate correctness of any mechanistic explanation or hypothesis, an embodiment of the invention can nonetheless be operative and useful.

One of ordinary skill in the art will appreciate that methods, materials, growth substrates, growth conditions, peptide synthesis methods, protein expression methods, transformation methods and conditions, strains, strain of fungi, cloning methods and DNA assembly methods other than those specifically exemplified can be employed in the practice of the invention without resort to undue experimentation. All art-known functional equivalents, of any such methods, materials, growth substrates, growth conditions, peptide synthesis methods, proteins expression methods, transformation methods and conditions, strains, cloning methods and DNA assembly methods are intended to be included in this invention.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1: Intrinsic Binding Parameters for Copper

To compare binding affinities from natural peptide motifs versus those derived in silico, select peptides were characterized for their binding parameters through isothermal titration calorimetry (ITC). The natural peptides were chosen because they have been previously characterized and have amino acid residues that are highly represented in Cu-binding. The putative Cu-binding domain CXXC, is found in metalloproteins with diverse functions, such as the metal-binding domain of *E. coli* GTPase (HypB1,2) (Chung et al, 2008; Douglas et al, 2012); *Arabidopsis* sp. Zn- and Cu-binding peptides (CZB-7) (U.S. Pat. No. 7,659,362), and in a consensus motif represented in different types of Cu binding (Cu-02) (Bertini et al, 2010). The rationally-designed peptide motifs, used for comparison are predicted, in silico to bind Cu (HHTC, CHSK) or Zn (KDKD, KDTK) (Kozisek et al., 2008). The peptides were derived by applying quantum mechanical methods that consider complexation energies of the metal with the amino acid side chains of a primary coordination sphere in a metalloprotein, and the molecular geometry (Ni-octahedral, Zn-tetrahedral, Cu-square planar) of the cognate metal 27. These are referred to according to their metal binding residues. A positive control, HHTC, was used that was previously characterized for Cu binding by using matrix-assisted desorption/ionization (MALDI) and isothermal titration calorimetry (ITC). A negative control, CHSK, was used that was determined through MALDI to not bind Cu in the gas phase, despite in silico predictions. The list of assessed peptides is provided in Table 1 and their respective amino acid sequences is provided in Table 3.

Figure 1B:
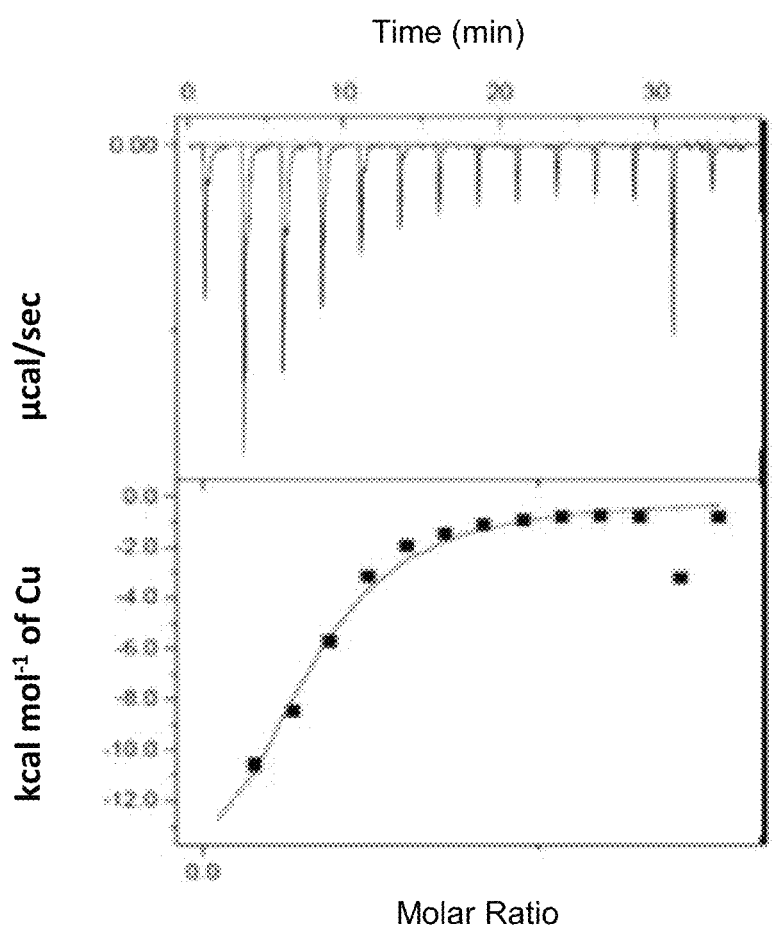
Figure 1C:
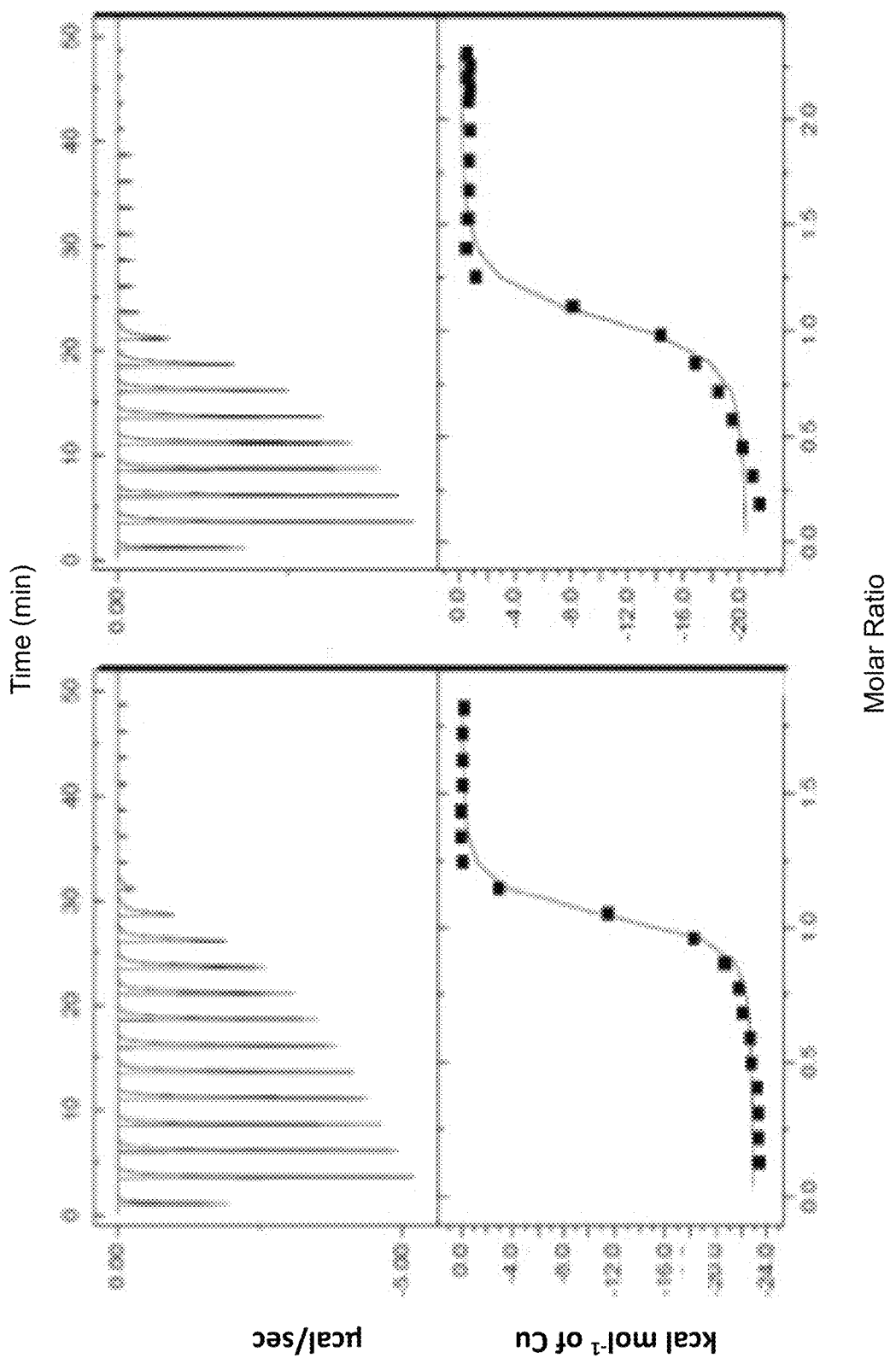

The natural peptides showed a range of affinities for Cu as shown in FIGS. 1A-1C and Table 1. The binding affinities for the rationally-designed motifs HHTC and CHSK had high affinities for Cu and were comparable to the natural HypB peptides. Binding parameters for HHTC with Cu have been previously published and were conducted at pH 7 with ACES buffer (Kozisek et al., 2008). At pH 7, thermodynamic modeling and experimental data show that Cu is mostly precipitated (>99%) into a solid mineral $Cu(OH)_2(s)$ phase (Navarette et a., 2011). This suggested that the reported binding parameters would be confounded by a change in enthalpy due to Cu dissociation from a solid mineral phase, rather than from Cu binding to the HHTC peptide. The binding experiments were thus conducted at pH 5.5, where 99.991% of Cu is predicted to remain as $Cu^{2+}$. The published binding affinity for HHTC is $K_a=(2.4\pm0.5)\times 10^6$ $M^{-1}$. The observed parameters for HHTC match the published binding affinity within error despite differences in experimental conditions. Additionally, the use of buffers with different heats of ionization, such as ACES (N-(2-Acetamido)-2-aminoethanesulfonic acid) buffer and MES buffer (used in these experiments), with $\Delta H_{ion}=31.4$ kJ/mol and 15.5 kJ/mol, respectively, did not appear to affect the measured enthalpies for Cu binding. These results indicate the previously published binding parameters accurately describe between Cu and the peptide under these conditions and are not due to proton transfer or Cu-mineral phase changes.

Example 2: Specificity of Metal Binding

E-waste components have multiple metals, and these remain in solution after removal of the scaffold material. In order to determine if the constructs tested herein were specific for Cu, competing metal ions were added to the peptide-Cu complex. Ni and Zn were chosen as the competing ions and are often competitors for the same ligand due to their similar electron configuration, ionic radius, valence, and/or molecular geometry. Similarly, Cu was added as a competing ion to solutions with other metal-peptide mixtures.

Figure 1D:
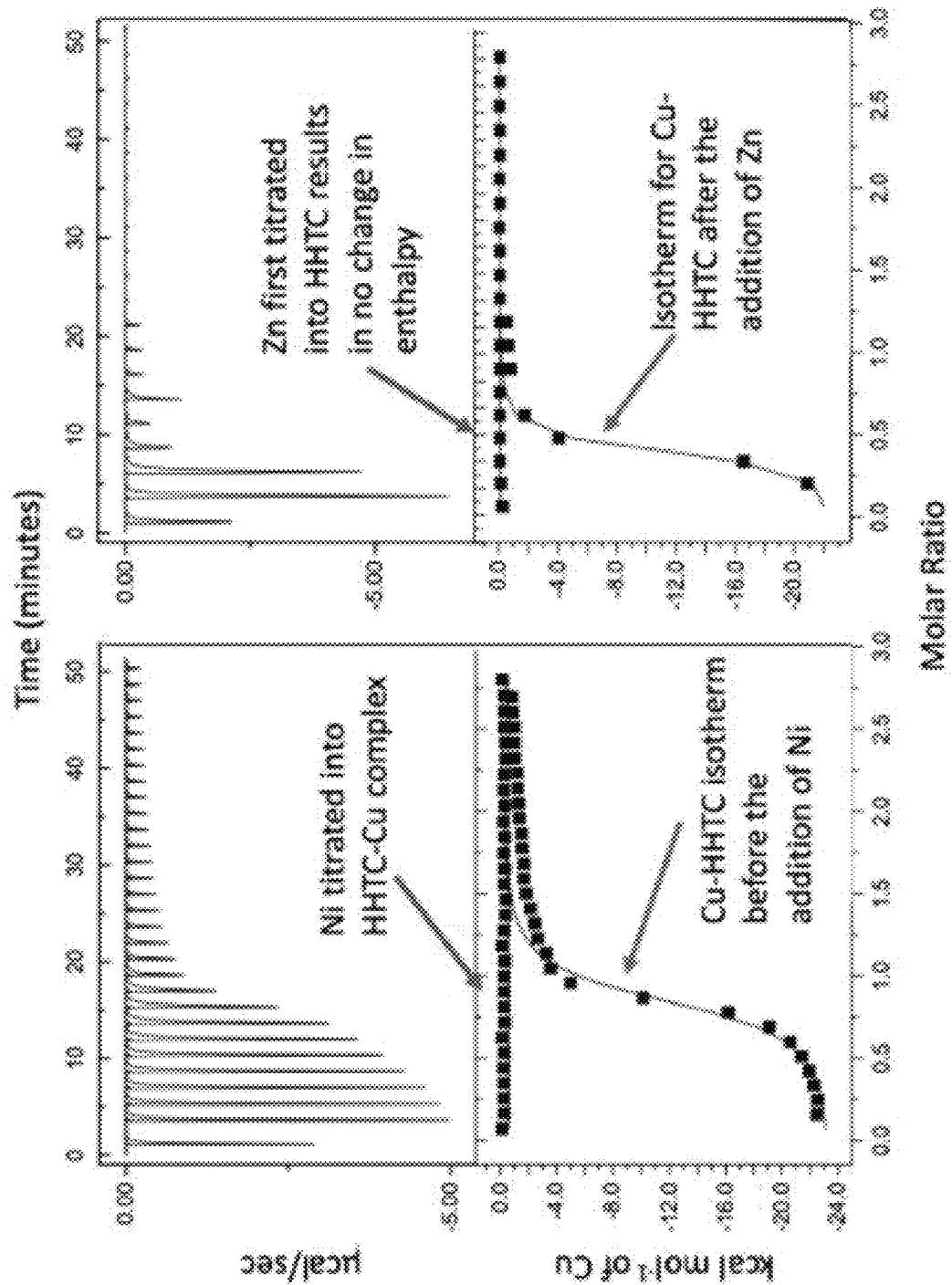

Intrinsic binding parameters were first determined for each peptide with individual metal solutions then apparent binding parameters were obtained when a competing metal was titrated into the already-formed metal-peptide complex. Previously published binding parameters on the select peptides did not determine whether they were specific to or showed preference for Cu when competing with other ions in solution FIG. 1D shows isotherms for competition experiments with HHTC and Cu, where Ni was titrated into the HHTC-Cu complex and resulted in no observed change in heat. Additionally, Cu was titrated into the sample cell containing I-HTC and Zn and revealed Cu binding but no Zn binding. This indicates that Cu occupied all available binding sites and was not dissociated from the peptide when competing ions were introduced into the solution. In all cases where Zn or Ni was titrated into an already-formed peptide-Cu complex, there was no change in enthalpy when the competing metals were added to the solution, indicating that Cu was not replaced by the competing ions.

Figure 1E:
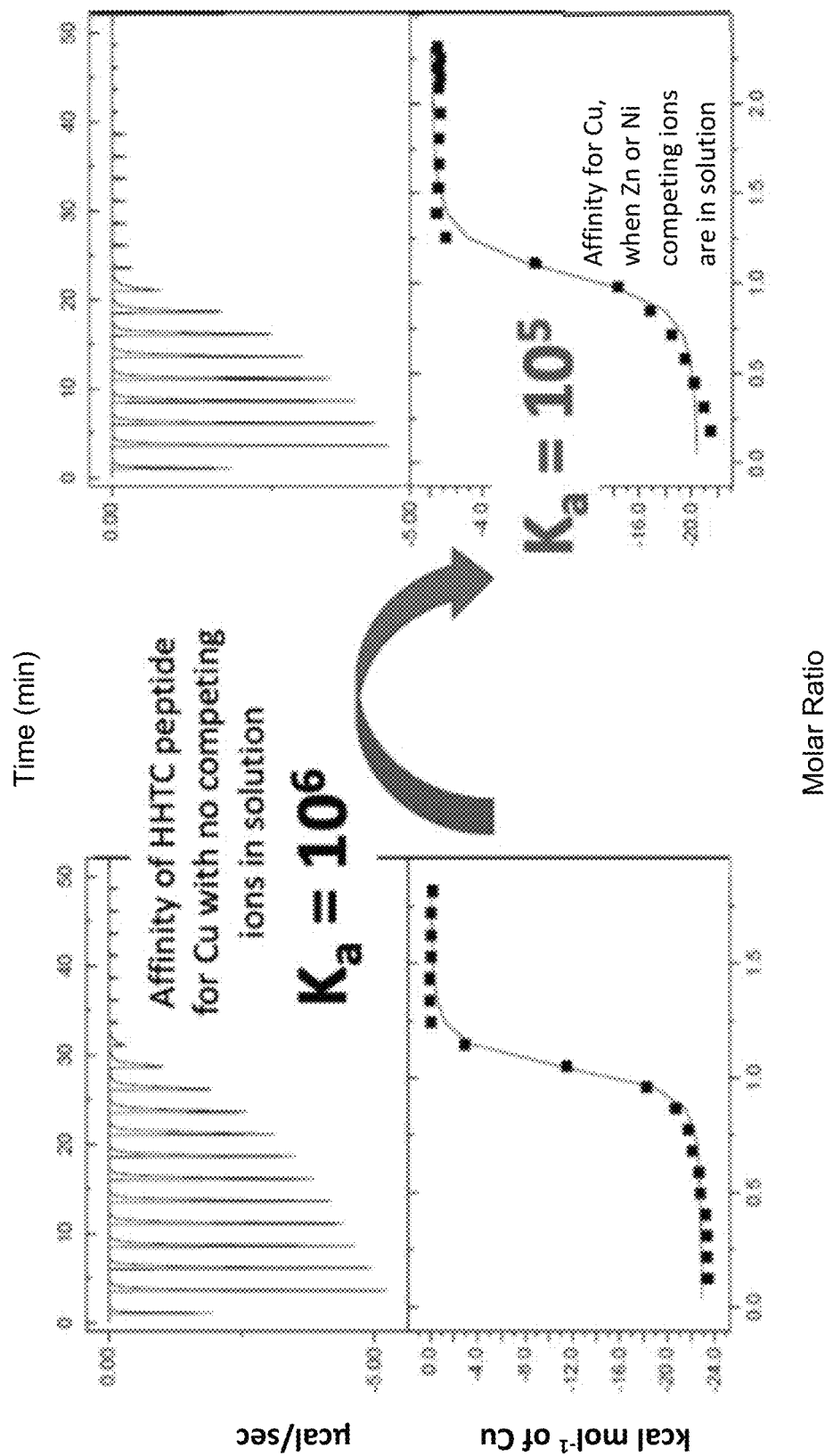

It was then tested whether the peptides would bind to Zn or Ni only. No isotherm was calculated in all cases, indicating the peptides did not bind these metals (Table 1). Cu was subsequently titrated into the peptide+Zn, or peptide+Ni solutions to determine if the affinity for Cu was retained when competing ions were in solution. The HypB peptides retained their affinity for Cu at the same or higher level when Ni or Zn was in solution while Cu affinity for the consensus motif Cu-02 was an order of magnitude lower when Zn was in solution and Cu affinity was lost when Ni was in solution (Table 1). The CZB-7 peptide that had previously shown a weak affinity for Cu at $K_a=(7.78\pm1.25)\times 10^3$ $M^{-1}$, did not bind Cu at all when the competing ions were in solution even though there was no appreciable binding to Zn or Ni, as no isotherm was calculated in these cases. In the case of the synthetic peptides (rational design), the affinities of HHTC and CHSK for Cu were lowered by an order of magnitude when Zn or Ni was in solution (Table 1). Additionally, the peptide CHSK showed the affinity for Cu was lost when Ni was the competing ion. The Cu isotherm for HHTC is shown after it was titrated into a solution containing Zn and HHTC (FIG. 1E).

It is a recognized phenomenon that a determinant of peptide selectivity for a divalent metal ion follows the Irving-Williams series (Irving & Williams, 1948), where the stability constants (i.e., strength of bonds due to electrostatic interactions between molecules) for metal complexes with any set of ligands is: $Mg^{2+}<Mn^{2+}<Fe^{2+}<Co^{2+}<Ni^{2+}<Cu^{2+}>Zn^{2+}$. If this is the case, then any peptide tested would preferentially bind Cu, and it would displace all of the other metals in the series, regardless of other metal-ligand specificity principles. To test whether the rational design approach was effective at predicting specific binding to other metals, or whether any peptide would bind Cu with high affinity, peptides were assessed that were designed to bind Zn. The Zn-binding peptide KDTK had a higher affinity for Cu than it did for the cognate metal, Zn (Table 1) and KDKD did not show any binding to Zn, however KDKD did bind Cu with low affinity. Thus, with these peptides, Cu bound with higher affinity by at least an order of magnitude than for the cognate metal, Zn.

Example 3: Binding Parameters of Modified Synthetic Peptides

Figure 2:
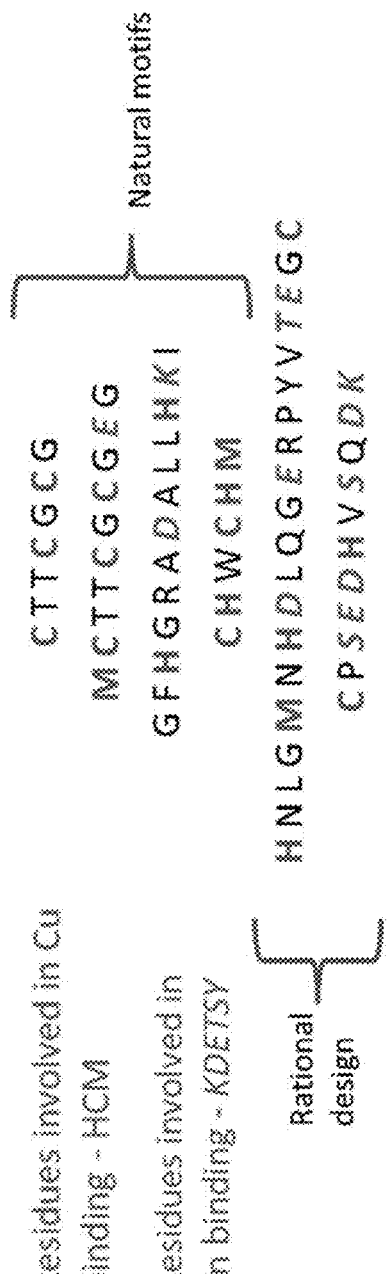
FIG. 2: Primary amino acid sequences for natural peptides (HypB1, HypB2, CZB-7, Cu02, and those derived through rational design (HHTC, CHSK), SEQ ID NOs: 1-6, respectively. Amino acids that are highly represented in Cu binding in the sequences are shown in gray, and those most implicated in Ni or Zn binding are shown in gray and italics. SEQ ID NOs for the sequences shown in FIG. 2 are listed in Table 3.

It was observed that rationally-derived peptides had a lower affinity for Cu when competing ions were in solution, despite there being no apparent binding to the competing ions. The designer peptides were further examined. The primary amino acid sequences for the natural and rationally-derived peptides were compared and some of the latter contained residues that are highly represented in Ni and Zn binding sites (FIG. 2). Data mining studies show KDETSY (i.e., Lys, Asp, Glu, Thr, Ser and Tyr) amino acids are favored in Zn and Ni binding sites (Rulisek & Havlasm 2000), while 95% of residues in Cu binding sites are HCM (i.e., His Cys, and Met) (Chung et al., 2008). The natural motif from the HypB protein did not contain any of the Zn/Ni binding residues, while the peptides with low Cu-binding affinities, such as CZB-7 and the rationally designed peptides, did (FIG. 2).

To test whether the KDETSY residues were essential for retaining specificity for Cu by accommodating for molecular geometry, the binding parameters for HHTC and CHSK that had either the KDETSY residues omitted or replaced with non-interacting residues NLGQV (Asn, Leu, Gly, Gln, and Val) (Table 2). Amino acid sequences of the peptides of Table 2 are found in Table 3. The Cu binding affinities of the modified motifs were comparable to HypB and unmodified HHTC and CHSK affinities. An unpaired t-test between the original HHTC peptide and the one with KDETSY residues omitted (HHTC-Tr), revealed no significant difference (two-tailed P value=0.2783) in intrinsic binding affinity for Cu. The HHTC-Tr peptide had an intrinsic binding affinity for Cu comparable to the unmodified peptide and retained its affinity for Cu when Zn or Ni were in solution. The HHTC peptide with the KDETSY residues replaced with NLGQV (HHTC Replaced) had a slightly higher affinity (but not quite statistically significant by conventional criteria, two-tailed P=0.0621) for Cu than the original peptide and HHTC Replaced retained its affinity for Cu when Zn or Ni was in solution. Peptides in tandem were not assessed for Ni or Zn affinity.

The binding affinity for CHSK, however, was markedly different when non-binding amino acid residues were replaced or omitted. When the KDETSY residues were omitted from the peptide, CHSK-Tr, Cu affinity was similar to the original CHSK. However, affinity for Cu was lost, when Ni or Zn were present in solution even though no binding isotherm was observed for Ni or Zn. When the CHSK peptide had the KDETSY residues replaced with the non-interacting NLGQV residues, binding affinity of CHSK—Re for Cu was lowered by an order of magnitude and this was only slightly less, if Zn was in solution prior to the addition of Cu, and completely lost, if Ni was the competing ion.

TABLE 1

Metal-binding motifs assessed for Cu-binding parameters. Intrinsic association constants ($K_a$) for peptides titrated with Cu, Zn, Ni, and apparent binding constants when titrated with Cu after Zn or Ni was in solution.

| Type | Name[1] | Cognate Metal[2] | Cu $K_a$ [M$^{-1}$] | Zn $K_a$ [M$^{-1}$] | Ni $K_a$ [M$^{-1}$] | Zn → Cu $K_a$ [M$^{-1}$] | Ni → Cu $K_a$ [M$^{-1}$][3] | Ref. |
|---|---|---|---|---|---|---|---|---|
| Natural motif | HYpB1 | Unk | $(2.37 \pm 0.71) \times 10^6$ | 0 | 0 | $(1.29 \pm 0.26) \times 10^7$ | n/a | Douglas et al., 2012 |
| | HYpB2 | Unk | $(1.30 \pm 0.07) \times 10^6$ | 0 | 0 | $(1.98 \pm 0.99) \times 10^6$ | $(3.51 \pm 0.18) \times 10^6$ | Chung et al., 2008 |
| | CB-7 | Cu/Zn | $(7.78 \pm 1.25) \times 10^3$ | 0 | 0 | 0 | 0 | U.S. Pat. No. 7,659,362 |
| Consensus | Cu-02 | Cu | $(9.89 \pm 2.18) \times 10^5$ | 0 | 0 | $(4.97 \pm 0.70) \times 10^4$ | 0 | Bertini et al., 2010 |
| Rational Design | HHTC | Cu | $(1.74 \pm 0.49) \times 10^6$ | 0 | 0 | $(8.64 \pm 3.11) \times 10^5$ | $(5.02 \pm 1.10) \times 10^5$ | Kozisek et al., 2008 |
| | CHSK | Cu | $(1.28 \pm 0.33) \times 10^6$ | 0 | 0 | $(2.35 \pm 0.81) \times 10^5$ | 0 | Kozisek et al., 2008 |
| | KDTK | Zn | $(1.05 \pm 0.91) \times 10^4$ | $(2.44 \pm 3.53) \times 10^3$ | 0 | $(6.51 \pm 0.75) \times 10^3$ | n/a | Kozisek et al., 2008 |
| | KDKD | Zn | $(1.27 \pm 0.11) \times 10^4$ | 0 | 0 | $(3.08 \pm 2.33) \times 10^6$ | $(1.71 \pm 1.08) \times 10^6$ | Kozisek et al., 2008 |

[1] Amino acid sequences of named peptides in Table 3;
[2] Unk = Unknown;
[3] n/a not available.

TABLE 2

Intrinsic association constants ($K_a$) for modified rational design peptides titrated with Cu, Zn, Ni, and apparent binding constants when titrated with Cu after Zn or Ni was in solution.[1]

| Type | Name | Cu $K_a$ [M$^{-1}$] | Zn $K_a$ [M$^{-1}$] | Ni $K_a$ [M$^{-1}$] | Zn → Cu $K_a$ [M$^{-1}$] | Ni → Cu $K_a$ [M$^{-1}$][3] |
|---|---|---|---|---|---|---|
| Rational design with K, D, E, T, S, Y residues removed | HHTC Truncated | $(4.92 \pm 2.17) \times 10^6$ | 0 | 0 | $(1.67 \pm 0.85) \times 10^6$ | $(1.50 \pm 0.69) \times 10^6$ |
| | CHSK Truncated | $(1.08 \pm 0.10) \times 10^6$ | 0 | 0 | 0 | 0 |
| Rational design with K, D, E, T, S, Y residues replaced with N, L, G, Q, V | HHTC Replaced | $(1.55 \pm 0.21) \times 10^6$ | 0 | 0 | $(3.99 \pm 2.24) \times 10^6$ | $(6.42 \pm 3.76) \times 10^6$ |
| | CHSK Replaced | $(4.86 \pm 0.83) \times 10^5$ | 0 | 0 | $(3.34 \pm 0.46) \times 10^5$ | 0 |

TABLE 2-continued

Intrinsic association constants ($K_a$) for modified rational design peptides titrated with Cu, Zn, Ni, and apparent binding constants when titrated with Cu after Zn or Ni was in solution[1]

| Type | Name | Cu $K_a$ [M$^{-1}$] | Zn $K_a$ [M$^{-1}$] | Ni $K_a$ [M$^{-1}$] | Zn → Cu $K_a$ [M$^{-1}$] | Ni → Cu $K_a$ [M$^{-1}$][3] |
|---|---|---|---|---|---|---|
| 2xHHTC Replaced in tandem | 2x-HHTC-Re | (3.73 ± 0.53) × 10$^5$ | | | | |
| 3xHHTC Replaced in tandem | 3x-HHTC-Re | (1.50 ± 0.05) × 10$^5$ | | | | |

[1]Arrows Zn → Cu, Ni → Cu, indicate the association constants for Cu after Zn or Ni are in solution as competing ions.

TABLE 3

Amino Acid Sequences of Metal-Binding Peptides in Tables 1 and 2

| Name | Amino-Acid Sequence |
|---|---|
| HYpB1 | CTTCGCG SEQ ID NO: 1 |
| HYpB2 | MCTTCGCGEG SEQ ID NO: 2 |
| CZB-7 | GFHGRADALLHKI SEQ ID NO: 3 |
| CuO2 | HCWCHM SEQ ID NO: 4 |
| HHTC | HNLGMNHDLQGERPYVTEGC SEQ ID NO: 5 |
| CHSK | CPSEDHVSQDK SEQ ID NO: 6 |
| KDTK | KTEYVDERSKSLTVDLTK SEQ ID NO: 7 |
| KDKD | KFFKDFRHKPATEL THED SEQ ID NO: 8 |
| HHTC Truncated | HNLGMNHLQGRPVTGC SEQ ID NO: 9 |
| CHSK Truncated | CPHVSQK SEQ ID NO: 10 |
| HHTC Replaced | HNLGMNHVLQGNRPLVTQGC SEQ ID NO: 11 |
| CHSK Replaced | CPNLGHVSQNK SEQ ID NO: 12 |
| 2x-HHTC-Re | HNLGMNHVLQGNRPLVTQGCHNLGMNHVLQGNRPLVTQGC SEQ ID NO: 13 |
| 3x-HHTC-Re | HNLGMNHVLQGNRPLVTQGCHNLGMNHVLQGNRPLVTQGCHNLGMNHVLQGNRPLVTQGC SEQ ID NO: 14 |
| Flex-HHTC-Re | GSGGSGHNLGMNHVLQGNRPLVTQGC SEQ ID NO: 15 |
| (Flex-HHTC-Re)$_2$ | GSGGSGHNLGMNHVLQGNRPLVTQGCGSGGSGHNLGMNHVLQGNRPLVTQGC SEQ ID NO: 16 |
| (Flex-HHTC-Re)$_3$ | GSGGSGHNLGMNHVLQGNRPLVTQGCGSGGSGHNLGMNHVLQGNRPLVTQGCGSGGSGHNLGMNHVLQGNRPLVTQGC SEQ ID NO: 17 |
| (Flex-HHTC-Re)$_4$ | GSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGC SEQ ID NO: 18 |
| (Flex-HHTC-Re)$_5$ | GSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGC SEQ ID NO: 19 |
| (Flex-HHTC-Re)$_6$ | GSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGC SEQ ID NO: 20 |

In Examples 2 and 3, binding affinity and specificity of naturally-occurring metal-binding motifs and peptides derived in silico were compared. It was found that they had comparable binding parameters. Cu is an essential element in biology with roles as a cofactor in a wide range of proteins and differences in binding affinities are due to the function of the metalloprotein from which they are derived. Copper is a highly reactive element that can cause oxidative damage if not tightly controlled and regulated by the cellular machinery thus, Cu proteins are characterized by high affinity for their cognate metal. When applying the rational design approach for peptide engineering, an important consideration is that the algorithms used to predict peptide binding partners rely on protein databases to characterize the molecular geometry of a cognate metal in a metalloprotein. The rationally-designed motifs showed comparable affinities to the natural peptides because they themselves are derived from known Cu structures in Protein Data Bank. (Rulisek & Havlas, 2000).

The algorithms used by previous researchers build from known metalloprotein structures to take short motifs and put them together into one peptide that fulfills the molecular geometry of the target metal (Kozisek et al., 2008). A key feature of these previous approaches is that only metal-peptide complexes for which there is crystal structure data are used, thus limiting the computational approach to metals with known biological functions and excluding metals that have not been characterized for biological interactions. It is possible to model interacting ligands with amino acid binding partners represented by individual residue side chains and without the need for the short motifs obtained through PDB that add rigidity to the peptides predicted to bind Cu. For example, it was found that while softer ligands such as cysteine and methionine have to be modeled using bulkier representations (e.g., the whole side chain of the residue). Harder ligands can be represented by simply using carboxyl groups, amines, and alcohols in computational models (Gutten & Rulisek, 2015). This approach to peptide prediction achieves a similar level of accuracy to using the whole amino acid molecule, while greatly reducing the computational requirements.

The rationally-designed HHTC and CHSK peptides give insight into the types of binding a metal can participate in. Both fulfill the preferred geometry of Cu, square planar, but with very different binding residues that suggest a certain fluidity in binding principles with regard to the ligands involved. Both tested peptides have non-canonical binding partners (threonine in HHTC, and serine and lysine in CHSK) as the residues that coordinate a Cu atom yet they each bind selectively and with similar affinity despite having vastly different primary sequences. Their affinity for Cu was enhanced when removing or replacing the amino acid residues (KDETSY) that were presumed to interact with competing metal ions. It is possible that this observed phenomenon was due to a more favorable fit around the Cu ion. An interesting phenomenon was observed when the Cu-02 and modified CHSK motifs, which lack the Zn and Ni binding residues, both lost affinity for Cu when Ni was in solution. While the peptide was designed for the square planar molecular geometry of Cu, Ni can bind in octahedral molecular geometry which can also accommodate square planar molecular geometry, thus making these peptides susceptible to competitive inhibition (Watt & Ludden, 1999).

The rational design peptides KDKD and KDTK, that were designed to bind Zn did bind Cu with more affinity than for their cognate metal and thus conform to the Irving-Williams stability series principles. While no S-containing residues are present in the peptide sequences (cysteine, methionine), both sequences tested contain the hydroxyl-containing threonine resides that can interact with Cu. Removal of these residues may affect their affinity to Zn, while limiting the electrostatic interactions with Cu. Additionally, since Cu is predicted to form the most stable complexes, metal sequestration from mixed solutions should follow the order of the stability of complexes as stated in the Irving-Williams series.

Metal-binding motifs developed through rational design by applying quantum mechanical methods that account for complexation energies of the elemental binding partners and molecular geometry of the cognate metal, not only show high affinity for the cognate metal, but they show specificity and discrimination against other metal ions that would-be competitors for the same binding sites. Previous computational models used to predict metal-peptide complexes use known crystal structure data. This limits peptide models to metals with biological function and known ligands. It is possible to model interacting ligands de novo with binding partners represented by using individual residue side chains as discreet binding partners and this approach can be used to design peptides to recover other metals such as rare earth or platinum group elements for biomining/recycling.

Example 4: Tandem Metal-Binding Motifs and Linear Increase in Metal Binding

Figure 3A:
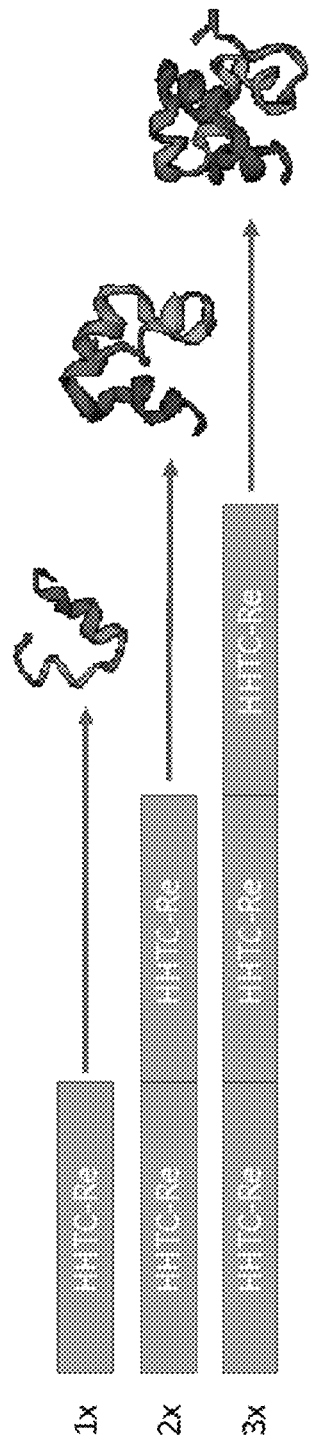
FIGS. 3A-D: Visual representation of the peptide molecules predicted by the QUARK ab initio program (FIG. 3A). ITC experiments to determine binding parameters for peptides 1×-(FIG. 3B), 2×-(FIG. 3C), and 3×-(FIG. 3D) HHTC-Re. Results indicate that 1×HHTC-Re is saturated in 5 injections, 2×HHTC-Re is saturated in 10 injections and 3×HTTC-Re is saturated in 15 injections. The binding affinity Ka reveals strong Cu binding for all tested peptides and a trend is observed that indicates the 2× and 3× peptides do bind 2 and 3 times more Cu, respectively.
Figure 3B:
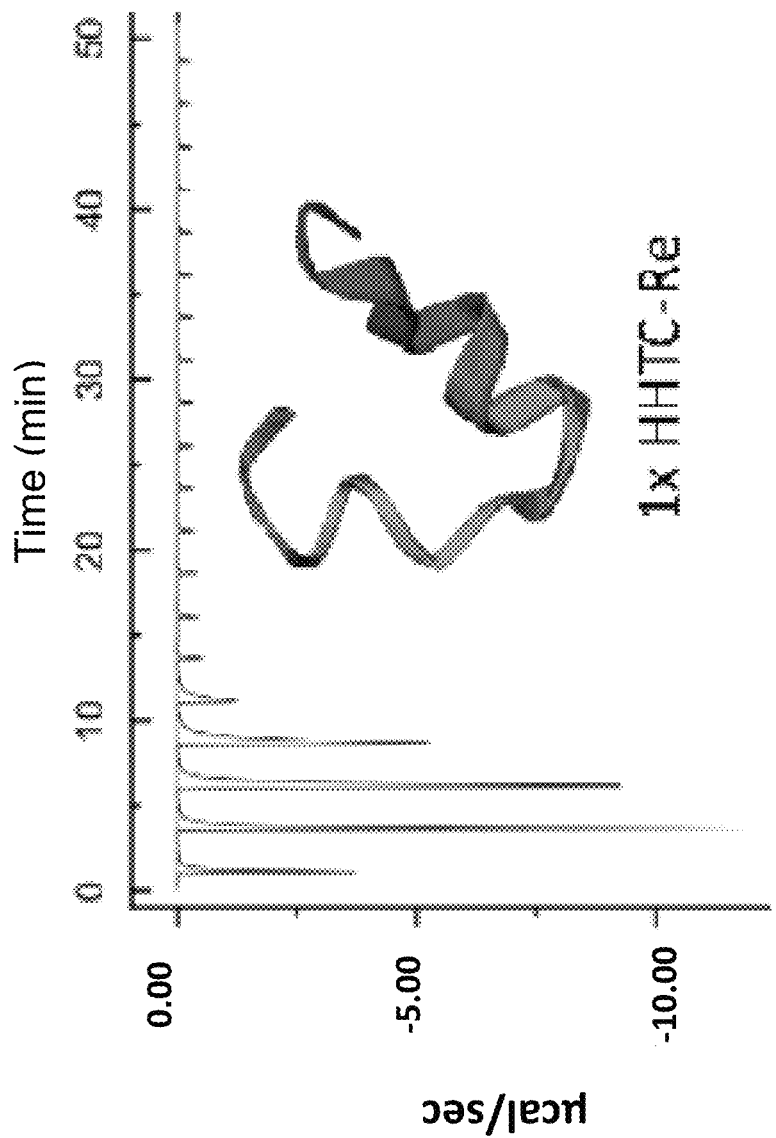
Figure 3C:
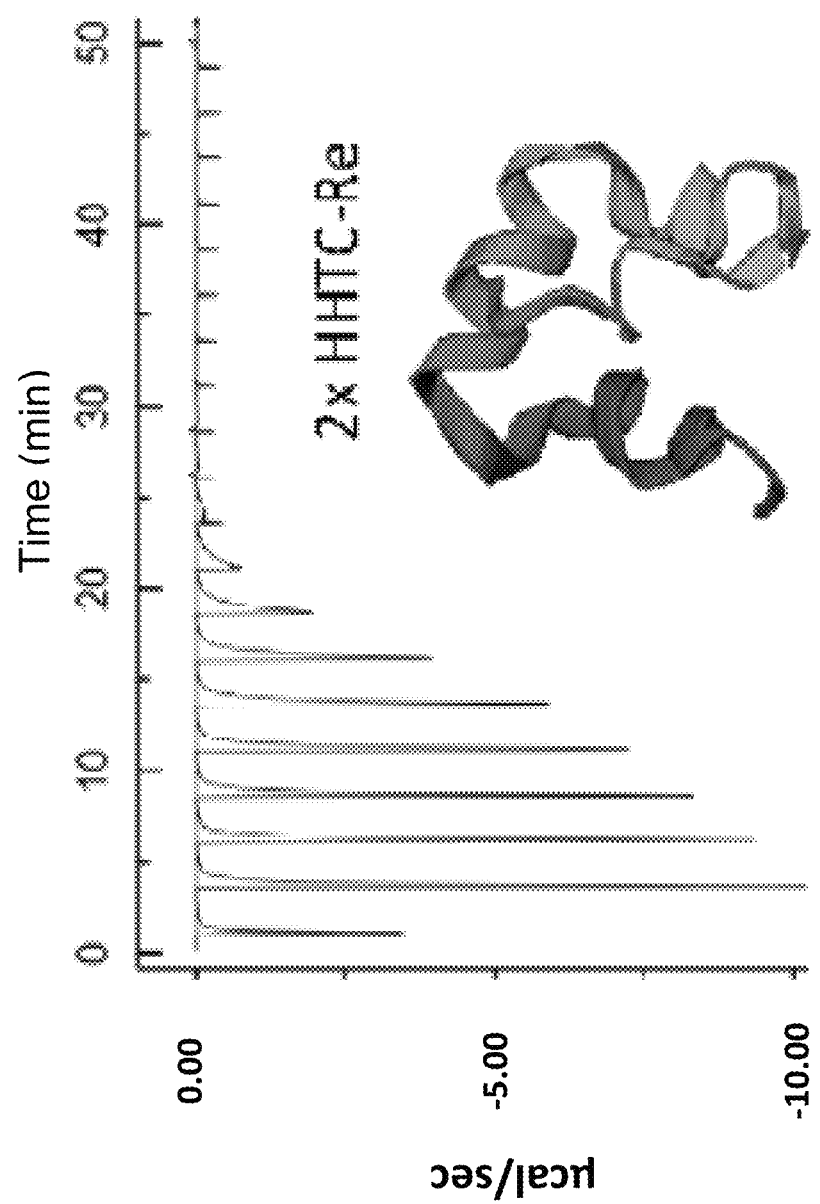
Figure 3D:
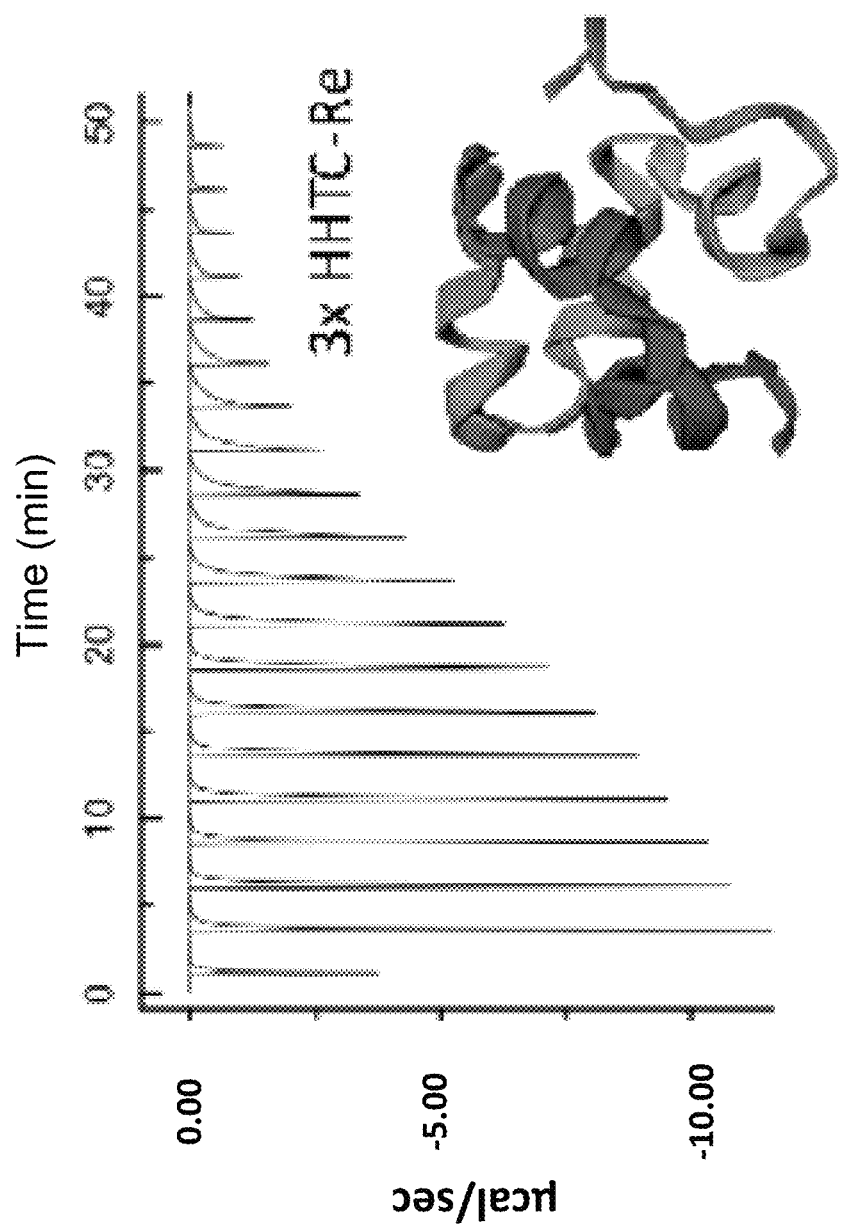

The tested peptides with a single iteration of the sequence indicated all had a 1:1 stoichiometry to Cu. In an applied setting it would be preferably to bind more than one metal atom per peptide molecule, thus it was tested whether having more than one metal binding motif in each peptide molecule would lead to a stoichiometric increase in Cu binding. Experiments were continued with the rationally designed peptide, HHTC, because it remained robust when non-binding amino acids were excluded or replaced with amino acids that did not interact with competing ions Ni or Zn. HHTC-Re motifs designed to have tandem repeats in series as single (1x-HHTC-Re), double (2x-HHTC-Re), and triple (3x-HHTC-Re) peptide molecules were modeled (Xu & Zhang, 2012) and constructed and assessed for their binding parameters (FIG. 3A). These peptides containing repeated motifs were tested for Cu binding parameters with ITC and binding affinity Ka reveals strong Cu binding for the all of the peptides (Table 2). Additionally, a trend is observed that indicated the 2x and 3x peptides do bind 2 and 3 times more Cu, respectively as a linear increase is observed as more motifs are added in series indicating that multiple metal ions are bound per peptide molecule (FIGS. 3B-D).

Example 5: Functionalizing Mycelium Surface with Metal-Binding Peptides Containing Chitin-Binding Domain This example describes steps to create a platform for functionalizing mycelial material. Using mycelia in comparison to previous efforts, such as flagella-based or cellulose filtration tools (Eckhard et al., 2017, Shipovskaya et al., 2003). One of the biggest benefits of using mycelium material is that it leverages the concept of economies of scale, and presents a feasible option for scale-up of the technology to a level that could be successfully implemented on a space mission or on Earth in developing countries with poor access to clean water. Fungi are capable of growth on diverse biomass types, and grow at a rate that is unparalleled by other biological agents used in synthetic biology applications today (Cavka & Jo, 2014).

Fungal mycelium was used as an immobile substrate, to design a cost-effective, scalable, biodegradable filtration system for metal recovery from aqueous solutions. Copper recovery is used in this example as a proof of concept. The feasibility of metal sequestration was assessed using functionalized mycelia by treating the fungal surface with peptides containing metal-binding motifs in tandem repeats containing a chitin-binding domain that could bind to the solid mycelial surface of a fungus. An exemplary fungus, the mushroom, *Gandoderma lucidum*, was employed for illustrative purposes. *G. lucidum* has been described in the literature for heavy metal binding, however this strain was not chosen for the innate metal-binding abilities, rather it was chosen because it was shown to be a suitable candidate for the objectives of our overall project; these include ease of growth on diverse substrates, under different temperature regimes, and in environments that would be representative of those found in space-exploration applications. Please refer to the iGEM Stanford-Brown-RISD team website: for the characterization of this and other fungal strains: 2018.igem.org/Team:Stanford-Brown-RISD/Experiments.

Mycelium, the vegetative structure of a fungus that is analogous to the root system of most plants, can branch out and bind various substrates to fill molds in different shapes, thus making it a good candidate for water filtration applications. Mycelium comprise chitin and as such chitin-binding domains will bind to fungal mycelium.

Figure 5:
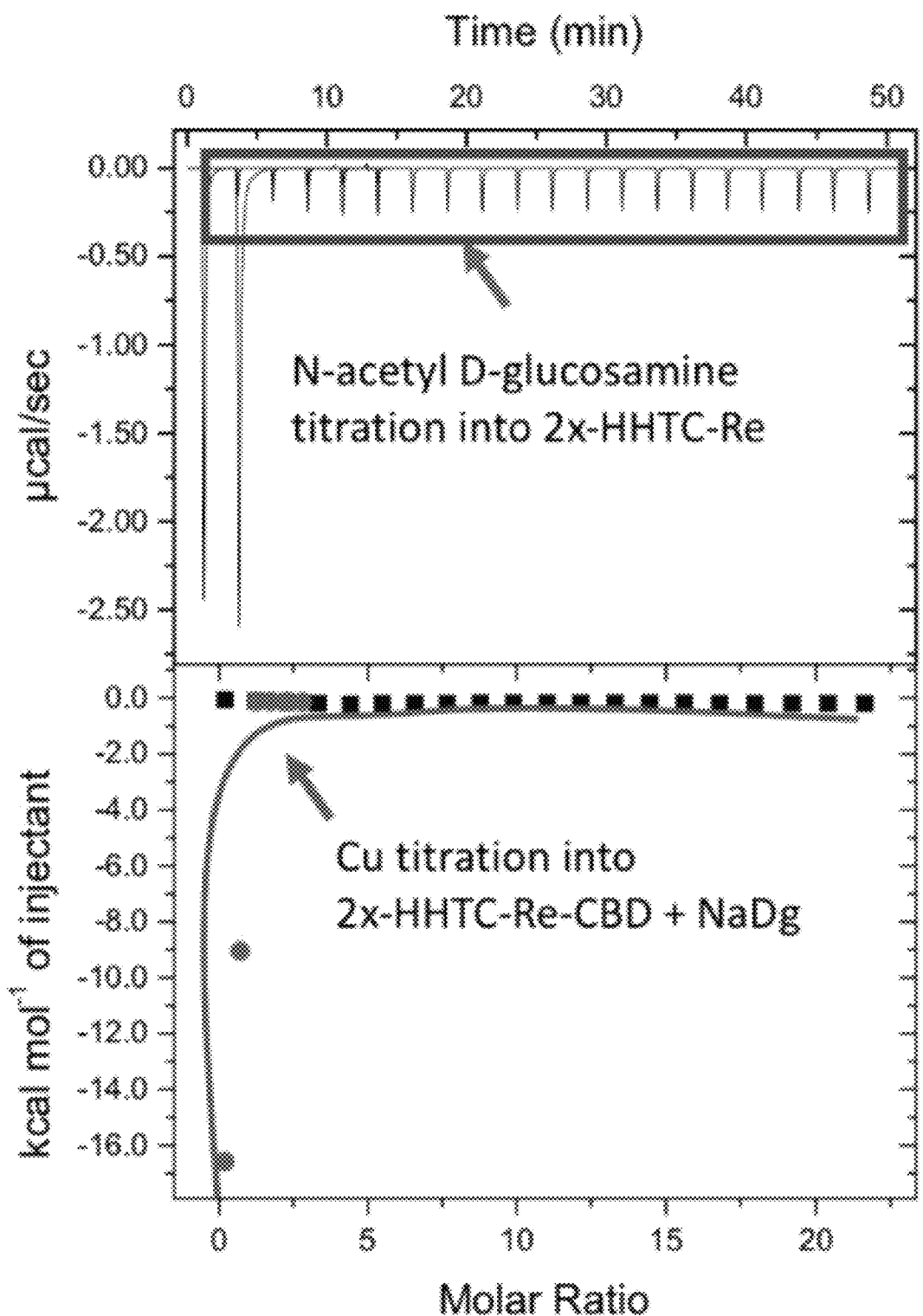
FIG. 5: ITC raw data and isotherm for experiment to assess binding affinity of fusion protein CBD-2×-HHTC-Re for chitin (represented by N-acetyl D-glucosamine) and Cu. Motifs retained affinity for chitin monomers in the presence of Cu, and retained affinity for Cu in the presence of chitin (monomers).

FIG. 5 depicts two experiments including Raw data (upper graph) and isotherm (lower graph) for 2x-HHTC-Re-CBD+N-acetyl D-glucosamine (NaDg) and Cu. N-acetyl D-glucosamine is analogous to a chitin monomer and is widely used in the art for assessing chitin binding). NaDg was first titrated into 2x-HHTC-Re-CBD and no isotherm was calculated because binding sites were not saturated by the ligand. Cu was then titrated into the 2x-HHTC-Re-CBD+NaDg complex and this resulted in a Cu affinity at $Ka=(7.61\pm1.49)\times10^6$ M$^{-1}$ that is an order of magnitude higher than 2x-HHTC-Re (no CBD) with $Ka=(3.73\pm0.53)\times$ 105 M−1 and comparable to 2×-HHTC-Re-CBD without bound NaDg with Ka=(1.55±0.21)×106 M−1. Data in FIG. 5 show 20 1 µL injections.

Figure 4A:
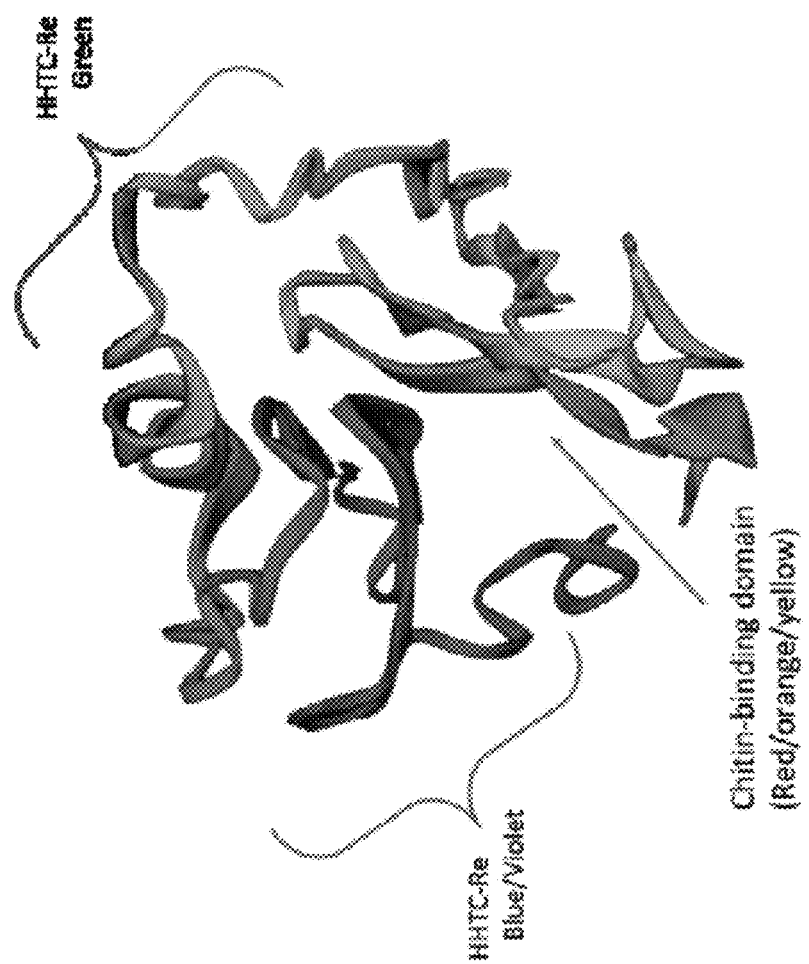
FIGS. 4A-C: QUARK ab initio model of 2×-HHTC-Re with chitin binding domain (FIG. 4A). Domains within the fusion protein have been annotated to display the conformation and spatial orientation.
Figure 4B:
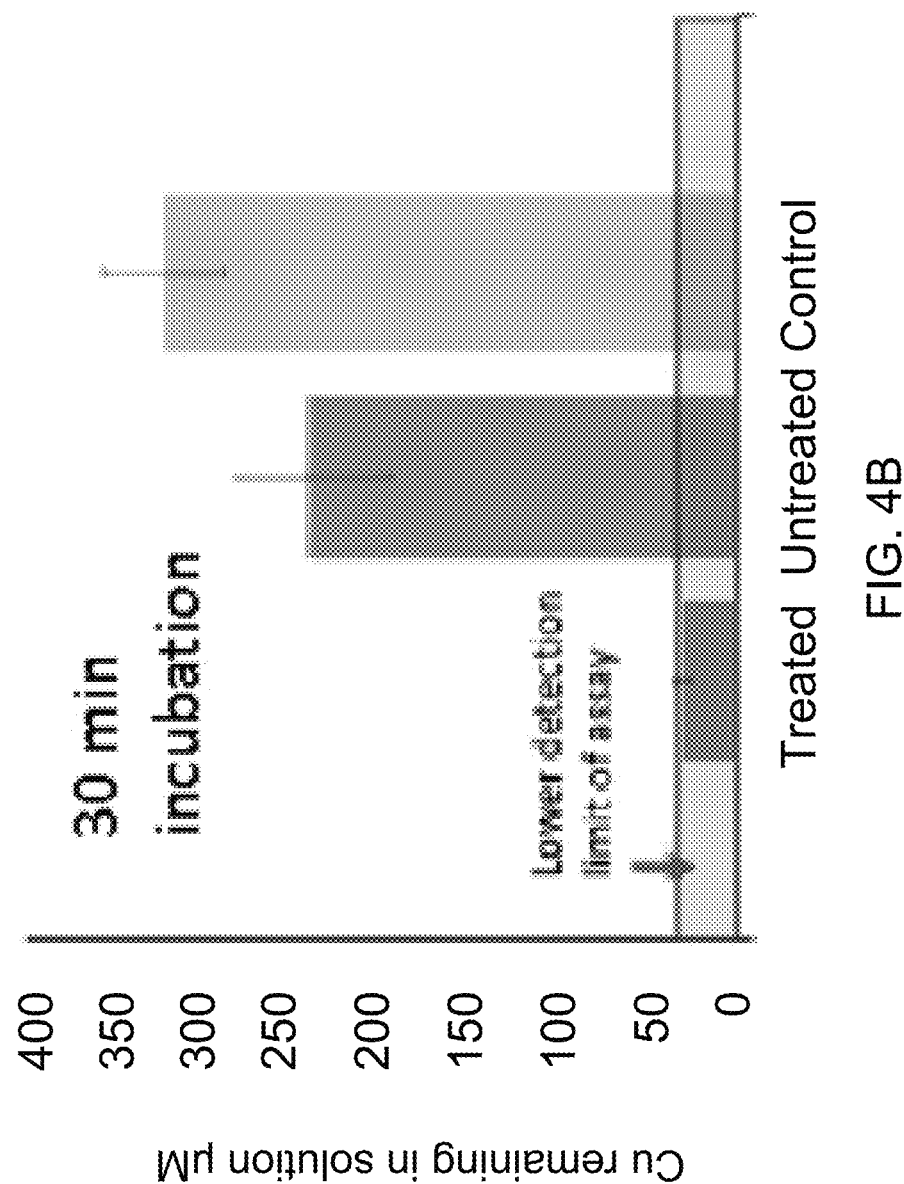
Figure 4C:
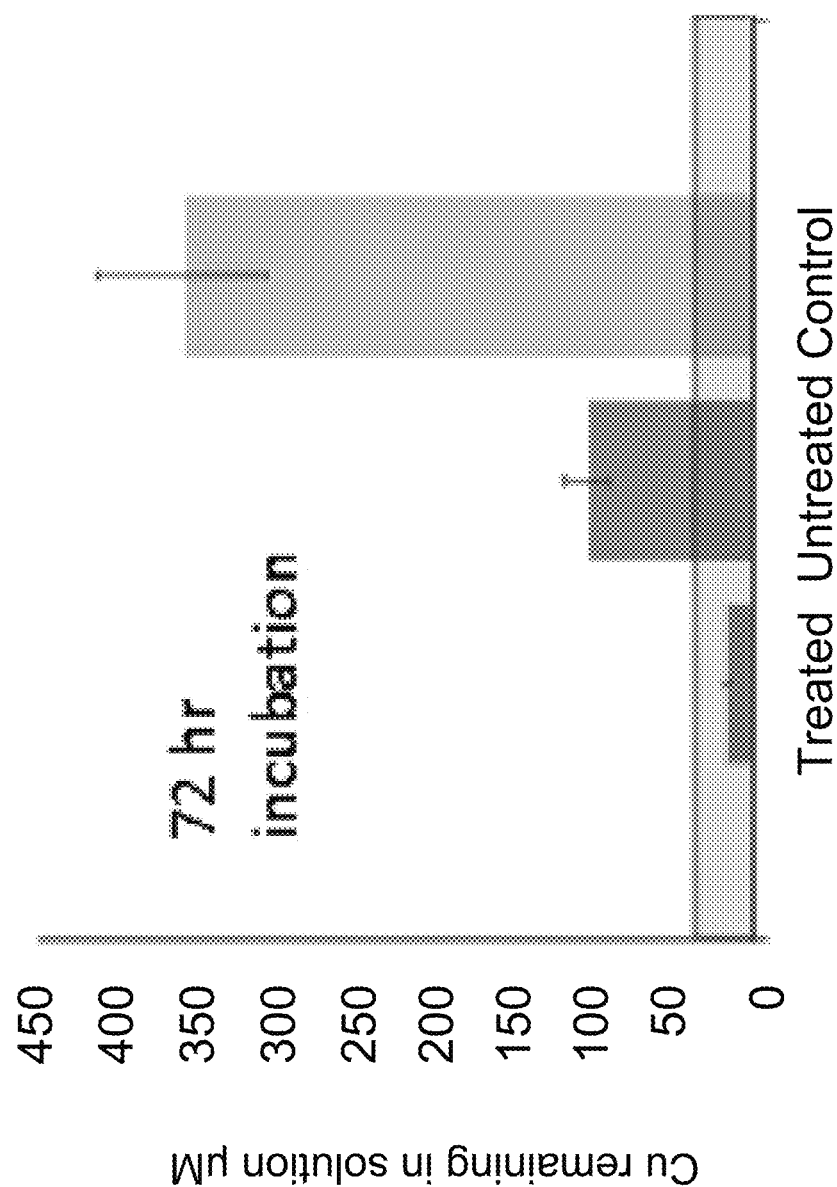

Mycelium treated with and without 0.45 mM 2×-HHTC-Re-CBD Cu/chitin-binding peptides (FIG. 4A) were incubated with a solution containing Cu to determine the amount of Cu sequestered by the mycelium. The Cu concentration in the starting solution was 325 (+/−25) µM Cu and after an incubation with the untreated mycelium, the remaining solution contained 250 (+/−50) µM Cu, thus the untreated mycelium adsorbed approximately 23% of the Cu available in solution. In contrast, after a 30-minute incubation, the mycelium treated with the CBD-2×-HHTC-Re motifs removed Cu to below detection limits thus sequestering at least 92% of the available Cu in solution (FIG. 4B). Incubation for 72 hours revealed (FIG. 4C) that the untreated mycelium removed about 70% of Cu in solution, while the treated mycelium removed all Cu from solution within the detection limits of the assay.

The fusion protein was designed to contain a chitin-binding domain (CBD), flexible linkers GSGGSG, and 2×-HHTC-Re (as illustrated schematically in FIG. 6). After confirming the copper binding of the individual HHTC-Rexn peptides it as assessed whether a fusion protein containing the copper binding sequence and the CBD could bind copper and chitin, and whether it could do so when already saturated with the other substrate. FIG. 6 schematically illustrates the method for making an exemplary fusion protein and an exemplary fusion protein made by the method. The method used to make the fusion is described below. The illustrated fusion 2×-HHTC-Re-CBD was employed in binding assays. The fusion 2×-HHTC-Re-CBD was selected as the candidate for testing because it displayed the most consistent and strong results during protein purification procedures and seemed most promising for downstream applications.

Schematic illustrations of various exemplary fusion peptide and protein configurations are provided in FIG. 7. Amino acid sequences of exemplary fusion peptides/proteins of the invention are provided in Table 7.

Tables 1-3 and 4 provide exemplary metal-binding domain useful in the fusion peptides/proteins of this invention. Table 5 provides exemplary Chitin-binding domains useful in the fusion peptides/proteins of this invention. Table 6 provides exemplary Substrate-binding domains useful in the fusion peptides/proteins of this invention.

This work assesses the feasibility of metal attenuation with engineered peptides and functionalized fungal mycelia. Incubation with metal-binding peptides containing a chitin binding domain increased the amount of Cu removed from solution. Previous studies have characterized the adsorptive properties of mycelium and they found that differences in metal-binding capacity for Cu was directly related to the cation exchange capacity at the mycelial surface of individual fungal species (Gonzalez-Chavez et al., 2002). Thus, there is an inherent ability for mycelium to attenuate heavy metals despite the hydrophobicity of the chitin substrate. This property is further enhanced by treatment with peptide constructs as described herein that turn an otherwise hydrophobic surface into a functionalized adsorptive surface that can interact with dissolved ions in aqueous solutions. While cellulose provides an alternative substrate and cellulose-binding motifs are known, the production of nanocellulose requires substantial inputs of glucose, and other forms of cellulose incur agricultural costs (Thakur & Voicu, 2016). Thus, it is our view that fungal mycelia provide a better alternative in most situations including biomining and bioremediation.

TABLE 4

Examplary Metal-Binding Domains

| Metal | Name | Sequence | Ref. |
|---|---|---|---|
| Manganese | DP1 | DEHGTAVMLK SEQ ID NO: 21 | Peana, et al., 2016 |
| Nickel | N3 | SGVYKVAYDASR SEQ ID NO: 22 | Li et al., 2019 |
| Molybdenum | MoS2-P15 | GVIHRNDQWTAPGGG SEQ ID NO: 23 | Cetinel et al., 2018 |
| Chromium | | EDGEECDCGE SEQ ID NO: 24 | Chen Y. et al., 2011 |
| Cobalt | Portion of cap43 | TRSRSHTSEG SEQ ID NO: 25 | Maruthamuthu M. et al., 2017 |
| Arsenic | | MCVNMEWGAFGDNGCLDDFR SEQ ID NO: 26 | Zhang et al., 2015 |
| Titanium (oxide) | | RKLPDA SEQ ID NO: 27 | Suzuki, 2016 |
| Palladium | Pd4 | TSNAVHPTLRHL SEQ ID NO: 28 | Tejada Vaprio, 2017 |
| Neodymium | Nd1 | GNLHTSATNLYLH SEQ ID NO: 29 | Sawada, 2016 |
| Terbium | dLBT | FIDTNNDGWIEGDELFIDTNNDGWIEGDELLA SEQ ID NO: 30 | Park et al., 2016 |
| Gallium | C3.8 | TMHHAAIAHPPH SEQ ID NO: 31 | Schonberger et al., 2019 |
| Indium | | ZGPWLEEEEEAYGWMDF SEQ ID NO: 32 | Baldwin G. et al., 2015 |

TABLE 4-continued

Examplary Metal-Binding Domains

| Metal | Name | Sequence | Ref. |
|---|---|---|---|
| Lanthanum | | TSTQCPSHIRACLKKR SEQ ID NO: 33 | Lederer et al. 2019 |
| | | RCQYPLCS SEQ ID NO: 34 | Lederer et al. 2019 |
| Praseodymium | | Ac-DVDA SEQ ID NO: 35 | Asso M. et al. 1985 |
| Uranium (uranyl oxide) | SUP | LDCRERIEKDLEDLEKELMEMKSIKLSDDEEAVVERALNYRDDSVYYLEKGD HITSFGCITYAEGLLDSLRMLHRIIEG SEQ ID NO: 36 | Horaru et al., 2019; Zhou et al., 2014 |
| Lanthanide | Lamp-1 | SCLWGDVSELDFLCS SEQ ID NO: 37 | Hatanaka et al. 2017 |
| | Lamp-2 | SCL YPSWSDYAFCS SEQ ID NO: 38 | |
| | Lamp-3 | SCPVWFSDVGDFMVCS SEQ ID NO: 39 | |
| | RE-1 | ACTARSPWICG SEQ ID NO: 40 | Zhang Y. et al. 2012 |
| | RE-3 | ACWPATRISCG SEQ ID NO: 41 | |
| | RE-6 | ACTAASPWICG SEQ ID NO: 42 | |
| | RE-10 | ACTARSPWACG SEQ ID NO: 43 | |

TABLE 5

Exemplary Chitin-Binding Domains (ChBD)

| | |
|---|---|
| TTNPGVSAWQVNTAYTAGQLVTYNGKTYKCLQPHTSLAGWEPSNVPALWQLQ SEQ ID NO: 44 | Examples herein |
| VGECVR-GRCPSGMCCSQFGYCGKGPKYCGX, where X is R or is absent SEQ ID NO: 45 | U.S. Pats. 5,514,779 and 8,618,066 |
| QTCASRCPRPCNAGLCCSIYGYCGSGNAYCGAGNCRCQCRG SEQ ID NO: 46 | U.S. Pat. 7,862,826 |
| AWQVNTAYTAGQLVTYNGKTYKCLQPHTSLAGWEPSNVPALWQLQ SEQ ID NO: 47 | U.S. Pat. 7,060,465 |
| AAQWQAGTAYKQGDLVTYLN KDYECIQPHTALTGWEPSNVPALWKYV SEQ ID NO: 48 | U.S. Pat. 7,060,465 |
| AATWSSSTAY NGGATVAYNG HNYQAKWWTQ GNVPSSSTGD GQPWADL SEQ ID NO: 49 | U.S. Pat. 7,060,465 |
| XSSNGTAYRFDCSKGLHWDMSLNTCNWPDAAGRVEGDHLLP where X is M or is absent SEQ ID NO: 50 | NCBI:WP_123954886.1 |
| XKLNKITLLTGLALLVSSEAYSHGYVESPAFSCIIM where X is M or is absent SEQ ID NO: 51 | GenBank: AJI64525.1 |
| XTTVHQGTMPSGKTGRHMILAVWTVNDTPM AFYSCSDVQF where X is M or is absent SEQ ID NO: 52 | GenBank: KPI33923.1 |
| SKFRTECNTARGKGHMLIAYPGDCSQYISCDSNDQSPQQCASGTVFNSEKQ RCDFRANVPSCKV SEQ ID NO: 53 | Heyman et al. 2020; GeneBank AK130064.1 |

TABLE 6

Exemplary Substrate-Binding Domains

| Substrate | Substrate-Binding Domain Sequence | Reference |
|---|---|---|
| Cellulose | MDWNANIAPGNSVEFGIQGAGSVGNVIDITVE SEQ ID NO: 54 | GenBank CBK74878 |
| | MNASYNGTLAPNANVTIGYQASHSGNSAAPGACTLNGTTCAVG SEQ D NO: 55 | NCBI WP099505134.1 |
| | ISGTVNNLWNATWKQSGTTLSASGVDWNKTLAPGA-TAEFGFCAAR SEQ ID NO: 56 | NCBI WP 148830312.1 |
| | MATQSHWGQCGGIGYSGPTVCASGTTCQVLNPYYSQCLPTTPTG SEQ ID NO: 57 | U.S. Pat. 6,407,208 |
| | AECSKLYGQCGGKNWNGPTCCESGSTCKVSNDYYSQCLPS SEQ ID NO: 58 | U.S. Pat. 7,445,922 |
| | TQSHYGQCGG IGYSGPTVCA SGTTCQVLNP YYSQCL SEQ ID NO: 59 | U.S. Pat. 8,506,717 |
| Xylan | TGSCSVSAVRGEEWADRFNVTYSVSGSSSWVVTLGLNGGQSVQSSW NAALTGSSGTVTARPNGSGNSFGVTFYKNGSSATPGATCATG SEQ ID NO: 60 | Black et al., 1995 |
| Lignin | HFPSPIFQRHSH SEQ ID NO: 61 | Oshiro et al., 2017; Yamaguchi et al., 2016 |
| | HFPSPIFQRHSHGHFPSPIFQRHSH SEQ ID NO: 62 | Oshiro, et al., 2017 |
| | VQHNTKYSVVIR SEQ ID NO: 63 | Yamaguchi et al., 2016 |
| | YHPNGMNPYTKA SEQ ID NO: 64 | Yamaguchi et al., 2016 |

TABLE 7

Exemplary Fusion Peptide/Proteins

| | | |
|---|---|---|
| CBD-linker-HTTC-Re | TTNPGVSAWQVNTAYTAGQLVTYNGKTYKCLQPHTSLAGWEPSNVPALWQLQGSGGSGHNLGMNHVLQGNRPLVTQGC | SEQ ID NO: 65 |
| CBD-(linker-HTTC-Re)$_2$ | TTNPGVSAWQVNTAYTAGQLVTYNGKTYKCLQPHTSLAGWEPSNVPALWQLQGSGGSGHNLGMNHVLQGNRPLVTQGCGSGGSGHNLGMNHVLQGNRPLVTQGC | SEQ ID NO: 66 |
| CBD-(linker-HTTC-Re)$_3$ | TTNPGVSAWQVNTAYTAGQLVTYNGKTYKCLQPHTSLAGWEPSNVPALWQLQGSGGSGHNLGMNHVLQGNRPLVTQGCGSGGSGHNLGMNHVLQGNRPLVTQGCGSGGSGHNLGMNHVLQGNRPLVTQGC | SEQ ID NO: 67 |
| CBD-(linker-HTTC-Re)$_4$ | TTNPGVSAWQVNTAYTAGQLVTYNGKTYKCLQPHTSLAGWEPSNVPALWQLQGSGGSGHNLGMNHVLQGNRPLVTQGCGSGGSGHNLGMNHVLQGNRPLVTQGCGSGGSGHNLGMNHVLQGNRPLVTQGC | SEQ ID NO: 68 |
| CBD-(linker-HTTC-Re)$_5$ | TTNPGVSAWQVNTAYTAGQLVTYNGKTYKCLQPHTSLAGWEPSNVPALWQLQGSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGC | SEQ ID NO: 69 |
| CBD-(linker-HTTC-Re)$_6$ | TTNPGVSAWQVNTAYTAGQLVTYNGKTYKCLQPHTSLAGWEPSNVPALWQLQGSGGSGHNLGMNHVLQGNRPLVTQGCGSGGSGHNLGMNHVLQGNRPLVTQGCGSGGSGHNLGMNHVLQGNRPLVTQGCGSGGSGHNLGMNHVLQGNRPLVTQGC | SEQ ID NO: 70 |

Example 6: Methods

Peptide Synthesis.

Peptides were synthesized by Elim Biopharmaceuticals (Hayward, CA, USA), purified by HPLC with (H)Cl as the counter ion, and provided as a lyophilized powder. Purity was >980% and verified through mass-spectrometry. Peptides were modified to have N-terminal acetylation and C-terminal amidation to avoid having a charged peptide or protein. Peptides were reconstituted in 10 mM 2-(N-morpholino)ethanesulfonic acid (MES) buffer pH 5.5 and concentrations determined through spectrophotometry with the Pierce™ BCA Assay Kit Thermo Scientific).

Fusion Protein Production and Purification.

The DNA sequences encoding the 2×-HHTC-Re protein constructs containing an intein self-cleavage site, hexahistidine and Lumio detection tags, see FIG. 6, were commercially synthesized (Integrated Dna Technologies, gBlocks Gene Fragments) and were assembled into the pSB1C3 iGEM backbone using Gibson Assembly® Protocol (New England Biolabs, NEB). Plasmid PSB1C3 is a high copy number cloning vector carrying chloramphenicol resistance. A map of the plasmid is available from the website snapgene. Transformed high efficiency NEB® 5-alpha competent *E. coli* were used for plasmid construction and transformations were plated on chloramphenicol selective LB plates. The transformations were incubated at 37° C. overnight and DNA constructs were confirmed in selected colonies using verification primers and colony PCR, as is known in the art. Plasmids from sequence-verified clones were then transformed into the T7 Express® *E. coli* (NEB) protein production strain. His-tag purification on crude cell extract from the selected colonies was performed using HisPur® Ni-NTA spin columns (ThermoFisher). The standard protein purification protocol was modified by introducing a buffer containing 50 mM DTT for on-site cleavage, so the desired fusion protein could be eluted. A BCA Assay was then performed to determine total protein concentration in each elution. Following protein de-salting with Amcon® Ultra centrifugal filters, the presence of target protein in the final elution was confirmed using Lumio® Tag Detection Kit (ThermoFisher Scientific), The construction of the fusions is schematically illustrated in FIG. 6.

Mycelium Biomass Production.

To test the peptides, the monokaryon form of *Ganoderma lucidum* from U.S. Department of Agriculture Forest Products Laboratory culture collection was grown in plates containing liquid Potato Dextrose Yeast Agar (PDYA), composed of 2.0% dextrose, 0.10% potato extract, 0.15% yeast extract, and 97.50% water at 30° C. for 14 days. Pure mycelium material was isolated, cut into strips, pressed into thin uniform sheets, dried at 120° C. for three hours to kill the fungus, and then cut into uniform 1 cm2 pieces to be used as filter prototypes. Growth rates on varied substrates were tested to determine which could be used with minimal added growth medium. Noteworthy substrates of environmental relevance were sawdust, lawn clippings, and used coffee grounds and other forms of food waste. The standardized substrate on which different conditions were tested was potato dextrose yeast agar (PDYA) which provides optimal nutrients for the fungus without providing excess nutrients that encourage bacterial growth.

Phen Green SK Assay.

For Cu adsorption estimation, Phen Green SK dye (PGSK, Invitrogen, USA) was prepared in a stock solution of 28 µM in 0.9% PBS (Phosphate buffered saline). PGSK fluorescence is quenched in the presence of Cu and is proportional to the amount of Cu in a solution. This stock solution (200 L) was added to each well in a 96-well plate to which 25 µL of sample was added. All experiments were performed in triplicate and the reported concentrations are the average of n=3 experimental replicates. A standard curve was generated for Cu and PGSK and gave approximations of the amounts of Cu in the tested solutions.

Bulk Adsorption Experiments.

All experiments were conducted in triplicate. One cm2 pieces of mycelium were either treated with purified protein 0.45 mM CBD-2×HHTC in 10 mM MES buffer pH 5.5 or with buffer only in shake flasks for 24 hours. Treated and untreated mycelium were placed in 3 mL of 0.25 mM Cu solution and samples taken at 30 minutes and at 72 hours. The incubation medium was analyzed for the remaining Cu in solution. The amount of Cu adsorbed was calculated by taking the difference between the initial Cu in system and the remaining Cu after incubation with treated or untreated mycelium.

Isothermal Titration Calorimetry.

Isothermal titration calorimetry (ITC) was used to determine the association equilibrium constant (Ka). The instrument used was a MicroCal iTC200 microcalorimeter (Malvern Panalytical) in the Space Biosciences Division at NASA Ames Research Center, Mountain View, CA. Instrument performance was verified by running the standard Ca-EDTA titration kit available from the instrument manufacturer. All binding parameters for the test were within the specifications determined by the manufacturer. The buffer chosen for the ITC experiments was 10 mM MES buffer. It was chosen because it has been shown not to cause metal ion interference as a result of complexation or amine oxidation, is stable through the entire range of pH 3-11, and has a stable pka over a relatively wide temperature range (15° C.-45° C.) (Wang & Lawrence, 1989; Kandegedara & Rorabacher, 1999). Buffer pH for peptides and metal solutions was 5.5 to prevent metal precipitation. Metal chloride salts were used as the source of metal ions, and speciation was verified through thermodynamic modeling using Visual Minteq. 3.040 (Gustafsson J. P. Visual MINTEQ, version 3.0. Available from: the web site vminteq.lwr.kth.se, 2007, KTH Royal Institute of Technology, Stockholm, Sweden). Concentrations of metal stock solutions were determined with an iCAP 7400 Inductively Coupled Plasma Optical Emission Spectrometer (ICP-OES, ThermoFisher Scientific) at the University of California Santa Cruz, Marine Analytical Laboratory. To measure Cu binding to our peptide, the metal solution was prepared from cupric chloride, dihydrate, ($CuCl_2 \cdot H_2O$, crystal, BAKER ANALYZED™ A.C.S. Reagent, J.T. Baker™ Peptides were used without further purification.

Peptide solutions were prepared by dissolving a weighed amount of the lyophilized powder in 10 mM MES prepared from Alfa Aesar™ MES, 0.2 M buffer soln., pH 5.5. Metal solutions were prepared by dissolving a weighed amount of the pure metal chloride salts or hydrates thereof into the same stock MES buffer that was used to prepare the peptide solution to minimize the effect of the heat of dilution/mixing when measuring the samples.

The ITC experiments were run at 25° C. and set to deliver 20, 0.5-1 µL injections at 150 see intervals. Titrate and titrant solutions were de-gassed prior to loading into the calorimeter cell and injection syringe. The procedure involved titrating (Cu, Zn, Ni)—Cl2 in excess by 10-20 times the concentration of the cognate motif. Typically, the peptide solutions were prepared to 0.5 mM, and the metal salts were at 2.4-64 concentrations. In some cases of low affinity, or when no saturation of the metal-binding peptide was observed, up to 100 times the concentration of metal was used. Metal-chloride salts were chosen because they remain as dissolved ions with chloride as the counter ion. This was complementary to the peptide conditions where chloride (HCl) was used as the counter ion during purification. The experiments were run such that the metal solution in the syringe was titrated into the peptide solution in the cell. Raw data were corrected by subtracting the heats of dilution, Integrated heat data were fit with a one-site binding model using the Origin-7™ software provided with the MicroCal iTC200 microcalorimeter. The "best-fit" parameters resulting from the nonlinear regression fit of these data are also shown in the figures.

Controls and heat of injections, heat of dilution. The mixing and dilution effects for the ITC experiments were minimized by using the same buffer for the peptide and metal salt preparations. Heat of dilution was determined by three titration experiments where 1) metal chloride (ligand) solution was titrated into buffer in the sample cell, 2) buffer was injected from the syringe into the peptide-buffer solution in the sample cell, and 3) buffer was titrated into buffer only in the sample cell. Metal-chloride titrations into the sample cell with blank buffer released heats comparable to blank buffer mixing where buffer-buffer titrations released 0.02 µcal/sec per injection, 5 mM $CuCl_2$=0.08 µcal/sec, 2.6 mM $NiCl_2$=0.05 µcal/sec. Heat of dilution/mixing for 6.4 mM $ZnCl_2$ was measured at 1.0 µcal/sec per injection and up to 15 µcal/sec for 64 mM $ZnCl_2$. In cases where heat of dilution/mixing caused a high background, the blank values were subtracted from the raw data prior to model isotherm fits. The heat of ionization of the buffer due to the release or uptake of protons during binding from the buffer conjugate base was determined to be negligible, thus data were not corrected for the heat of ionization of the MES buffer (Freyer & Lewis, 2008).

REFERENCES

Asso M. et al. Calcium and praseodymium complexes in solution. Chemical Biology & Drug Design. 26(1):10-20, (1985).

Baldwin G. S. et al. High Affinity Binding of Indium and Ruthenium Ions by Gastrins. PLOS ONE. 10(10): e0140126. DOI:10.1371/journal.pone.0140126 (2015).

Benson, D. E., Wisz, M. S., Liu, W. & Hellinga, H. W. Construction of a novel redox protein by rational design: Conversion of a disulfide bridge into a mononuclear iron-sulfur center. Biochemistry. 37, 7070-7076 (1998).

Bertini, I., Cavallaroa, G. & McGreevya, K. S. Cellular copper management—a draft user's guide. Coordination Chemistry Reviews. 254, 506-524 (2010).

Black G. W. et al. A modular xylanase containing a novel non-catalytic xylan-specific binding Domain. Biochem J. 307:191-195 (1995).

Borrok, D. M. & Fein, J. B. The impact of ionic strength on the adsorption of protons, Pb, Cd, and Sr onto the surfaces of Gram negative bacteria: testing non-electrostatic, diffuse and triple-later models. Journal of Colloid Interface Science. 286, 110-126 (2005).

Cavka, A. & Jo, L. J. Comparison of the growth of filamentous fungi and yeasts in lignocellulose-derived media. Biocatalysis and Agricultural. Biotechnology 3(4), 197-204 (2014).

Cerimi K. et al. Fungi as source for new bio-based materials: a patent review. Fungal Biology and Biotechnology. 6:17. (2019). DOI: /10.1186/s40694-019-0080-y.

Cetinel S. et al. Biomining of MoS2 with Peptide based Smart Biomaterials. Nat. Scientific Reports. (2018) 8:3374|DOI:10.1038/s41598-018-21692-4 (February 2018).

Chen X. et al. Fusion protein linkers: Property, design and functionality. Adv. Drug Delivery Reviews. 65:1357-1369 (2013).

Chen Y. et al. Characterization of the Organic Component of Low-Molecular-Weight Chromium-Binding Substance and Its Binding of Chromium. J. of Nutrition (American Society for Nutrition). 141(17): 1225-1232. DOI: 10.3945/jn.111.139147.

Chichili V. P. R. et al. Linkers in the structural biology of protein-protein interactions. Protein Science. 22(2), 153-167 (2013).

Chung, K. C. et al. A High-Affinity Metal-Binding Peptide from *Escherichia coli* HypB. J. Amer. Chem. Soc. 130, 14056-14057 (2008).

Cruz, N. et al. Engineering the *Escherichia coli* outer membrane protein OmpC for metal bioadsorption. Biotechnology Letters. 22, 623-629 (2000).

Douglas, C. D., Dias, A. V. & Zamble, D. B. The metal selectivity of a short peptide maquette imitating the high-affinity metal binding site of *E. coli* HypB. Dalton Transactions. 41, 7876-7878 (2012).

Dudev, T. & Lim, C. Competition among metal ions for protein binding sites: Determinants of metal ion selectivity in proteins. Chemical Reviews. 114, 538-556 (2014).

Eckhard, U. et al. Discovery of a proteolytic flagellin family in diverse bacterial phyla that assembles enzymatically active flagella. Nature communications 8(1), 521 (2017).

Freyer, M. W. & Lewis, E. A. Isothermal titration calorimetry: Experimental design, data analysis, and probing macromolecule/ligand binding and kinetic interactions. Methods in Cell Biology. 84, 79-113 (2008).

Gonzalez-Chavez, C., D'haen, J., Vangronsveld, J. & Dodd, J. C. Copper sorption and accumulation by the extraradical mycelium of different *Glomus* spp. (arbuscular mycorrhizal fungi) isolated from the same polluted soil. Plant and Soil. 240(2), 287-297 (2002).

Gutten, O. & Rulisek, L. How simple is too simple? Computational perspective on importance of second-shell environment for metal-ion selectivity. Physical Chemistry Chemical Physics 17(22), 14393-14404 (2015).

Gutten, O. & Rulisek, L. Predicting the stability constants of metal-ion complexes from first principles. Inorganic Chemistry. 52, 10347-10355 (2013).

Hatanaka T. et al. Rationally designed mineralization for selective recovery of the rare earth elements. Nature Communications. 8:15670. 10 pp. DOI: 10.1038/ncomms15670 (May 2017).

Heymann D. et al. Structure of a Consensus Chitin-Binding Domain Revealed by Solution NMR. Preprint posted Jan. 9, 2020. Available at the web site bioRxiv.org. DOI: 10.1101/2020.01.08.899344.

Horaru M. et al. Probing Metal Ion Discrimination in a Protein Designed to Bind Uranyl Cation with Femtomolar Affinity. Frontiers Molecular Biosciences. 6 Article 73. (August 2019).

Ilyas, S., Lee, J. & Chi, R. Bioleaching of metals from electronic scrap and its potential for commercial exploitation. Hydrometallurgy. 131, 138-143 (2013).

Irving, H. & Williams, R. J. P. Order of stability of metal complexes. Nature. 162, 746 (1948).

Kandegedara, A. & Rorabacher, D. B. Noncomplexing tertiary amines as "better" buffers covering the range of pH 3-11. Temperature dependence of their acid dissociation Constants. Analytical Chemistry. 71, 3140-3144 (1999).

Kozisek, M. et al. Molecular Design of Specific Metal Binding Peptide Sequences from Protein Fragments: Theory and Experiment. Chemistry-A European Journal. 14(26), 7836-7846 (2008).

Kuroda, K. & Ueda, M. Molecular design of the microbial cell surface toward the recovery of metal ions. Current Opinion in Biotechnology. 22, 427-433 (2011).

Lederer F. L. et al. Identification of peptides as alternative recycling tools via phage surface display—How biology supports Geosciences. Minerals Engineering. 132:245-250 (March 2019) published on line (December 2018).

Li H. et al. Enhanced Biosorption of Nickel Ions on Immobilized Surface-Engineered Yeast Using Nickel-Binding Peptides. Frontiers in Microbiology. 10 article 1254, 7 pp. (June, 2019) DOI: 10.3389/fmicb.2019.01254.

Maruthamuthu M. et al. Manganese and cobalt recovery by surface display of metal binding peptide on various loops of OmpC in *Escherichia coli*. J. Industrial Microbiology & Biotechnology. 45:31-41(2018) published November 2017.

Maruyama, T. et al. Proteins and protein-rich biomass as environmentally friendly adsorbents selective for precious metal ions. Environmental science & technology 41(4), 1359-1364 (2007).

Nanda, V. & Koder, R. L. Designing artificial enzymes by intuition and computation. Nature Chemistry. 2(1), 15-24 (2010).

Navarrete, J. U., Borrok, D. M., Viveros, M. & Ellzey, J. T. Copper isotope fractionation during surface adsorption and intracellular incorporation by bacteria. Geochimica et Cosmochimica acta. 75(3), 784-799 (2011).

Nguyen, T. T. et al. Selective lead adsorption by recombinant Escherichia coli displaying a lead-binding peptide. Applied biochemistry and biotechnology 169(4), 1188-1196 (2013).

Oshiro S. et al. Binding behaviour of a 12-mer peptide and its tandem dimer to gymnospermae and angiospermae lignins. RSC Adv. 7:31338 (2017)

Park D. M. Bioadsorption of Rare Earth Elements through Cell Surface Display of Lanthanide Binding Tags. Environ. Sci. Technol. 50, 5, 2735-2742 (2016)

Peana M. et al. Manganese binding to antioxidant peptides involved in extreme radiation resistance in Deinococcus radiodurans. J Inorg Biochem. 164: 49-58 (2016).

Prabhukumar, G., Matsumoto, M., Mulchandani, A. & Chen, W. Cadmium removal from contaminated soil by tunable biopolymers. Environmental Science & Technology. 38(11), 3148-3152 (2004).

Rosmalen M. et al. Tuning the Flexibility of Glycine-Serine Linkers to Allow Rational Design of Multidomain Proteins. Biochemistry. 56, 50, 6565-6574 (2017).

Rulisek, L. & Havlas, Z. Theoretical studies of metal ion selectivity. 1. DFT Calculations of interaction energies of amino acid side chains with selected transition metal ions (Co2+, Ni2+, Cu2+, Zn2+, Cd2+, and Hg2+). J. Amer. Chem. Soc. 122, 10428-10439 (2000).

Sawada T et al. Selective Rare Earth Recovery Employing Filamentous Viruses with Chemically Conjugated Peptides. ChemistrySelect (Chemistry Europe). 1(11): 2712-2716 (2016).

Schonberger N. et al. Directed Evolution and Engineering of Gallium-Binding Phage Clones—A Preliminary Stud. Biomimetics 4(2) 35. DOI:10.3390/biomimetics4020035 (May 2019).

Shipovskaya, A. B., Evseeva, N. V. & Timofeeva, G. N. Physicochemical modification of cellulose acetate for manufacturing films, membranes, and biofilters. Russian Journal of Applied Chemistry 76(9), 1514-1518 (2003).

Stair, J. L. & Holcombe, J. A. Metal remediation and preconcentration using immobilized short-chain peptides composed of aspartic acid and cysteine. Microchemical journal. 81(1), 69-80 (2005).

Suzuki Y. et al. Structure and Dynamic Properties of a Ti-Binding Peptide Bound to TiO2 Nanoparticles As Accessed by (1)H NMR Spectroscopy. J. Phys Chem B. 120(20):4600-7 (2016).

Tejada Vaprio R. E. Peptide-directed Nanoparticle Synthesis with a Denovo Pd-binding Sequence Fused to a Reporter Protein. Theses and Dissertations. 2393 (2017).

Thakur, V. K. & Voicu, S. I. Recent advances in cellulose and chitosan based membranes for water purification: a concise review. Carbohydrate polymers. 146, 148-165 (2016).

Urbina J. et al. A New Approach to Biomining: Bioengineering Surfaces for Metal Recovery From Aqueous Solution. Nature Scientific Reports. 9:16422 (November 2019) DOI: 10.1038/S41598-019-52778-2.

Wang, F. & Lawrence, M. Oxidation of tertiary amine buffers by copper(II). Inorganic Chemistry. 28, 169-170 (1989).

Watt, R. K. & Ludden, P. W. Nickel-binding proteins. Cellular and Molecular Life Sciences. 56(7-8), 604-625 (1999).

Xu, D. & Zhang, Y. Ab initio protein structure assembly using continuous structure fragments and optimized knowledge-based force field. Proteins. 80, 1715-1735 (2012).

Yamaguchi A. et al. Discovery of 12-mer peptides that bind to wood lignin. Nat. Scientific Reports. 6:21833 (2016).

Yang, W. et al. Rational design of a calcium-binding protein. J. Amer. Chem. Soc. 125, 6165-6171 (2003).

Yunus, I. S. & Tsai, S. L. Designed biomolecule-cellulose complexes for palladium recovery and detoxification. RSC Advances. 5(26), 20276-20282 (2015).

Zhang H. et al. Systematic identification of arsenic-binding proteins reveals that hexokinase-2 is inhibited by arsenic. Pro. Natl. Acad Sci. (PNAS). 112(49): 15084-15089.

Zhang Y. et al. Tuning the autophagy-inducing activity of lanthanide-based nanocrystals through specific surface-coating peptides. Nature Materials. 11:817-826 (2012).

Zhou L. et al. A protein engineered to bind uranyl selectively and with femtomolar affinity. Nature Chemistry. 6: 236-241 (2014).

The invention claimed is:

1. A method for isolating a target chemical substance from solution which comprises:
   contacting a solution containing the target chemical species with a substrate which contains a carbohydrate functionalized with:
   a fusion peptide or protein comprising an amino acid sequence which binds to the target chemical substance, and
   an amino acid sequence which is a substrate-binding domain which binds to the carbohydrate, such that at least a portion of the target chemical substance in the solution binds to the fusion peptide and is isolated from the solution.

2. The method of claim 1, wherein the target chemical species contains a metal.

3. The method of claim 2, wherein the metal is a transition metal, a rare earth metal, or a platinum group metal.

4. The method of claim 1, wherein the solution is an aqueous solution.

5. The method of claim 1, wherein the carbohydrate is chitin and the substrate-binding domain is a chitin-binding domain.

6. The method of claim 5, wherein the chitin-containing substrate is fungal mycelium.

7. The method of claim 6, wherein the fungal mycelium is that of a unicellular or multicellular fungus.

8. The method of claim 6, wherein the fungal mycelium is that of a mushroom.

9. The method of claim 6, wherein the fungal mycelium is selected from the group of any one of the following: those that are alive, those that are dead, those that are dried, those that are dried and powdered, those that are molded into a desired shape by having been grown in a selected mold, those that are formed into a mat, and those that are formed into a porous substrate layer or mat.

10. The method of claim 6, wherein the fungal mycelium is grown in the presence of growth substrate in a mold to assume a desired shape.

11. The method of claim 5, wherein the fusion peptide or protein comprises at least one metal-binding domain and at least one chitin-binding domain.

12. The method of claim 11, wherein the fusion peptide or protein comprises at least two metal-binding domains.

13. The method of claim 11, wherein the fusion peptide comprises at least two metal binding domains and at least one flexible peptide spacer sequence positioned between the sequences of the at least two metal binding domains.

14. The method of claim 5, wherein the fusion peptide or protein comprises a metal-binding domain of an amino acid sequence of any one of SEQ ID NOs: 10-20.

15. The method of claim 1, wherein the substrate is functionalized by expression of a nucleic acid construct encoding the fusion peptide or protein.

16. The method of claim 1, wherein the substrate is fungal mycelium and the substrate is functionalized by expression of a nucleic acid construct encoding a fusion peptide or protein which comprises at least one metal-binding domain and at least one chitin-binding domain.

17. The method of claim 1, wherein the fusion peptide or protein comprises a tandem repeat of a carbohydrate-binding domain.

18. The method of claim 17, wherein the fusion peptide or protein further comprises at least two metal binding domains and at least one flexible peptide spacer sequence positioned between the sequences of the at least two metal binding domains.

19. The method of claim 5, wherein the substrate is fungal mycelium and the fusion peptide or protein further comprises a tandem repeat of a chitin-binding domain.

20. The method of claim 19, wherein the fusion peptide or protein further comprises at least two metal binding domains and at least one flexible peptide spacer sequence positioned between the sequences of the at least two metal binding domains.

* * * * *